(12) United States Patent
Irwin

(10) Patent No.: US 8,454,669 B2
(45) Date of Patent: *Jun. 4, 2013

(54) DEVICE FOR UV PHOTO-THERAPY

(75) Inventor: Dean S. Irwin, Del Mar, CA (US)

(73) Assignee: Photomedex, Montgomeryville, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/030,647

(22) Filed: Feb. 18, 2011

(65) Prior Publication Data

US 2011/0196457 A1 Aug. 11, 2011

Related U.S. Application Data

(63) Continuation of application No. 11/429,695, filed on May 8, 2006, now Pat. No. 7,891,361, which is a continuation of application No. 10/462,375, filed on Jun. 16, 2003, now Pat. No. 7,144,248, which is a continuation of application No. 10/274,838, filed on Oct. 18, 2002, now abandoned.

(60) Provisional application No. 60/336,337, filed on Oct. 18, 2001.

(51) Int. Cl.
*A61N 5/06* (2006.01)

(52) U.S. Cl.
USPC .......... 607/88; 607/89; 606/13; 606/16; 433/29; 362/572

(58) Field of Classification Search
USPC .......... 607/88–91; 606/3, 9, 13–18; 433/29; 362/572
See application file for complete search history.

(56) References Cited

U.S. PATENT DOCUMENTS

| | | |
|---|---|---|
| 3,986,513 A | 10/1976 | Stuhl |
| 4,095,113 A | 6/1978 | Wolff |
| 4,103,175 A | 7/1978 | Levin |
| 4,558,700 A | 12/1985 | Mutzhas |
| 4,560,883 A | 12/1985 | Kerschgens |
| 4,686,979 A | 8/1987 | Gruen et al. |

(Continued)

FOREIGN PATENT DOCUMENTS

WO   WO 2012/149110 A1   11/2012

OTHER PUBLICATIONS

Asawanonda et al., "308-nm Excimer Laser for the Treatement of Psoriasis," Archives of Dermatology, vol. 136, May 2000, pp. 619-624.

(Continued)

*Primary Examiner* — Ahmed Farah

(74) *Attorney, Agent, or Firm* — Gottlieb, Rackman & Reisman, P.C.

(57) ABSTRACT

Skin disorders such as, for example, atopic dermatitis, dyshidrosis, eczema, lichen planus, psoriasis, and vitiligo, are treated by applying high doses of ultraviolet light to diseased regions of a patient's skin. The dosage exceeds 1 MED as determined for the particular patient and may range from about 1 MED to about 20 MED or higher. The ultraviolet light has a wavelength within the range of about 295 nanometers to about 320 nanometers. High doses of ultraviolet light are preferably restricted to diseased tissue areas. A specialized handpiece provides a beam profile especially suitable for application of controlled doses. A specialized delivery device is useful for UV treatment of tissue within the mouth.

20 Claims, 29 Drawing Sheets

U.S. PATENT DOCUMENTS

| | | | |
|---|---|---|---|
| 4,891,818 A | 1/1990 | Levatter | |
| 4,927,231 A | 5/1990 | Levatter | |
| 4,930,504 A | 6/1990 | Diamantopoulos et al. | |
| 5,015,067 A | 5/1991 | Levatter | |
| 5,044,717 A | 9/1991 | Levatter | |
| 5,109,465 A | 4/1992 | Klopotek | |
| 5,300,097 A | 4/1994 | Lerner et al. | |
| 5,380,316 A | 1/1995 | Aita et al. | |
| 5,389,096 A | 2/1995 | Aita et al. | |
| 5,392,608 A | 2/1995 | Lee | |
| 5,514,168 A | 5/1996 | Friedman | |
| 5,595,568 A | 1/1997 | Anderson et al. | |
| 5,620,478 A | 4/1997 | Eckhouse | |
| 5,636,637 A | 6/1997 | Guiolet et al. | |
| 5,658,323 A | 8/1997 | Miller | |
| 5,772,656 A | 6/1998 | Klopetek | |
| 5,820,626 A | 10/1998 | Baumgardner | |
| 5,830,208 A | 11/1998 | Muller | |
| 5,836,999 A | 11/1998 | Eckhouse et al. | |
| 5,868,731 A | 2/1999 | Budnik et al. | |
| 5,944,748 A | 8/1999 | Mager et al. | |
| 5,955,840 A | 9/1999 | Arnold et al. | |
| 5,964,749 A | 10/1999 | Eckhouse et al. | |
| 5,979,454 A | 11/1999 | Anvari et al. | |
| 5,989,283 A | 11/1999 | Wilkens | |
| 5,997,530 A | 12/1999 | Nelson et al. | |
| 6,017,360 A | 1/2000 | Chubb et al. | |
| RE36,634 E | 3/2000 | Ghaffari | |
| 6,083,218 A | 7/2000 | Chou | |
| 6,171,301 B1 | 1/2001 | Nelson et al. | |
| 6,208,788 B1 | 3/2001 | Nosov | |
| 6,402,511 B1 | 6/2002 | Calderwood | |
| 6,413,268 B1 * | 7/2002 | Hartman | 607/94 |
| 6,436,127 B1 | 8/2002 | Anderson et al. | |
| 6,468,077 B1 | 10/2002 | Melikechi et al. | |
| 6,508,813 B1 | 1/2003 | Altschuler | |
| 6,663,620 B2 | 12/2003 | Altshuler et al. | |
| 6,663,658 B1 | 12/2003 | Kollias et al. | |
| 6,709,269 B1 | 3/2004 | Altshuler | |
| 6,736,832 B2 | 5/2004 | Lenderink et al. | |
| 6,918,905 B2 | 7/2005 | Neuberger | |
| 6,979,327 B2 | 12/2005 | Spencer | |
| 6,984,228 B2 | 1/2006 | Anderson et al. | |
| 7,114,248 B2 | 10/2006 | Weyerman | |
| 7,125,404 B2 | 10/2006 | Levatter | |
| 7,144,248 B2 * | 12/2006 | Irwin | 433/29 |
| 7,257,144 B2 | 8/2007 | Levatter | |
| 7,276,059 B2 | 10/2007 | Irwin | |
| 7,848,378 B2 | 12/2010 | Levatter | |
| 7,886,749 B2 | 2/2011 | Irwin | |
| 7,891,361 B2 | 2/2011 | Irwin | |
| 2001/0046247 A1 | 11/2001 | Hartman | |
| 2002/0002370 A1 | 1/2002 | Levatter | |
| 2002/0183811 A1 | 12/2002 | Irwin | |
| 2004/0015156 A1 | 1/2004 | Vasily | |
| 2004/0176824 A1 | 9/2004 | Weckwerth et al. | |
| 2006/0085053 A1 | 4/2006 | Anderson et al. | |
| 2006/0268946 A1 | 11/2006 | Levatter et al. | |
| 2007/0030876 A1 | 2/2007 | Levatter | |
| 2007/0032844 A1 | 2/2007 | Levatter | |
| 2007/0282402 A1 | 12/2007 | Irwin | |
| 2008/0240197 A1 | 10/2008 | Levatter et al. | |
| 2010/0195692 A1 | 8/2010 | Levatter | |
| 2010/0232469 A1 | 9/2010 | Levatter et al. | |
| 2011/0002918 A1 | 1/2011 | Levatter | |
| 2011/0004280 A1 | 1/2011 | Irwin | |
| 2012/0109042 A1 | 5/2012 | Koo et al. | |
| 2012/0217418 A1 | 8/2012 | Levatter et al. | |
| 2012/0219030 A1 | 8/2012 | Levatter | |
| 2013/0018442 A1 | 1/2013 | Irwin | |

OTHER PUBLICATIONS

Business Wire, Laser Photonics Inc. to Enter the Dermatology Market to Treat Psoriasis, Company Press Release, Jan. 13, 1998, 2 pages.

Freeman et al., Influence of Temperature on Ultraviolet Injury, Archives of Dermatology, vol. 89, Jun. 1964, pp. 858-864.

Guttman, Vitiligo laser Tx called 'extraordinary': Small group of patients shows some repigmentation after six treatments, Dermatology Times, Dec. 2000, 2 pages.

Letter dated Feb. 10, 2005 from Alan A. Limbach to Mark Gallagher re U.S. Appl. No. 10/462,375, 2 pages.

Njoo, M.D., M.D., et al., The Development of Guidelines for the Treatment of Vitiligo, Archives of Dermatology, vol. 135, No. 12, Dec. 1999, pp. 1514-1521.

Parrish et al., Action Spectrum for Phototherapy of Psoriasis, Journal of Investigative Dermatology, vol. 76, No. 5, 1981, pp. 359-362.

Questek Excimer Laser, Series 2240 Manual, 1986, 54 pages.

Rodewald et al., The Efficacy of 308nm Laser Treatment of Psoriasis Compared to Historical Controls, Dermatology Online Journal, vol. 7, No. 2, 2001, 16 pages.

Notice of Incomplete Reply of U.S. Appl. No. 10/274,838, dated Aug. 1, 2003.

Notice of Abandonment for U.S. Appl. No. 10/274,838, dated Nov. 14, 2005.

U.S. Appl. No. 09/694,086, filed Oct. 20, 2000 (now Abandoned).

Office Action of U.S. Appl. No. 09/694,086, dated Aug. 8, 2002.

Notice of Abandonment of U.S. Appl. No. 09/694,086, dated Apr. 23, 2003.

Final Office Action issued in U.S. Appl. No. 12/717,039, dated Dec. 11, 2012.

Office Action issued in U.S. Appl. No. 13/619,212, dated Oct. 16, 2012.

Office Action issued in U.S. Appl. No. 13/620,167, dated Dec. 11, 2012.

* cited by examiner

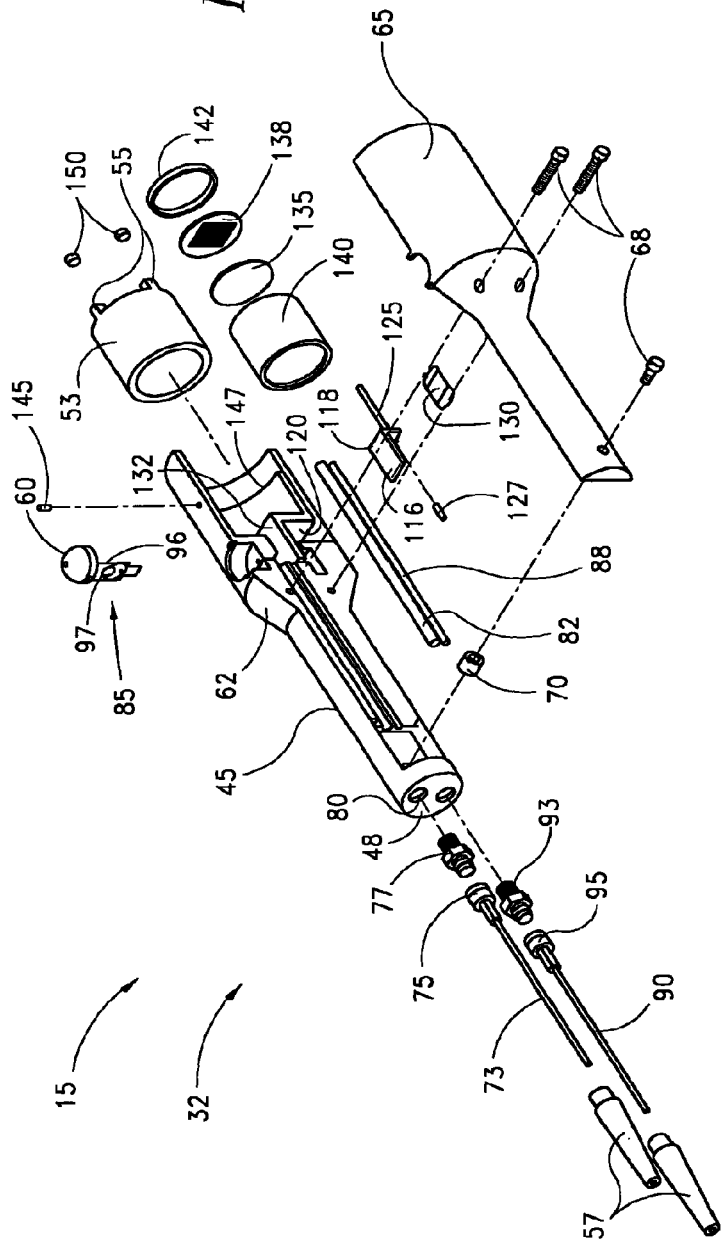

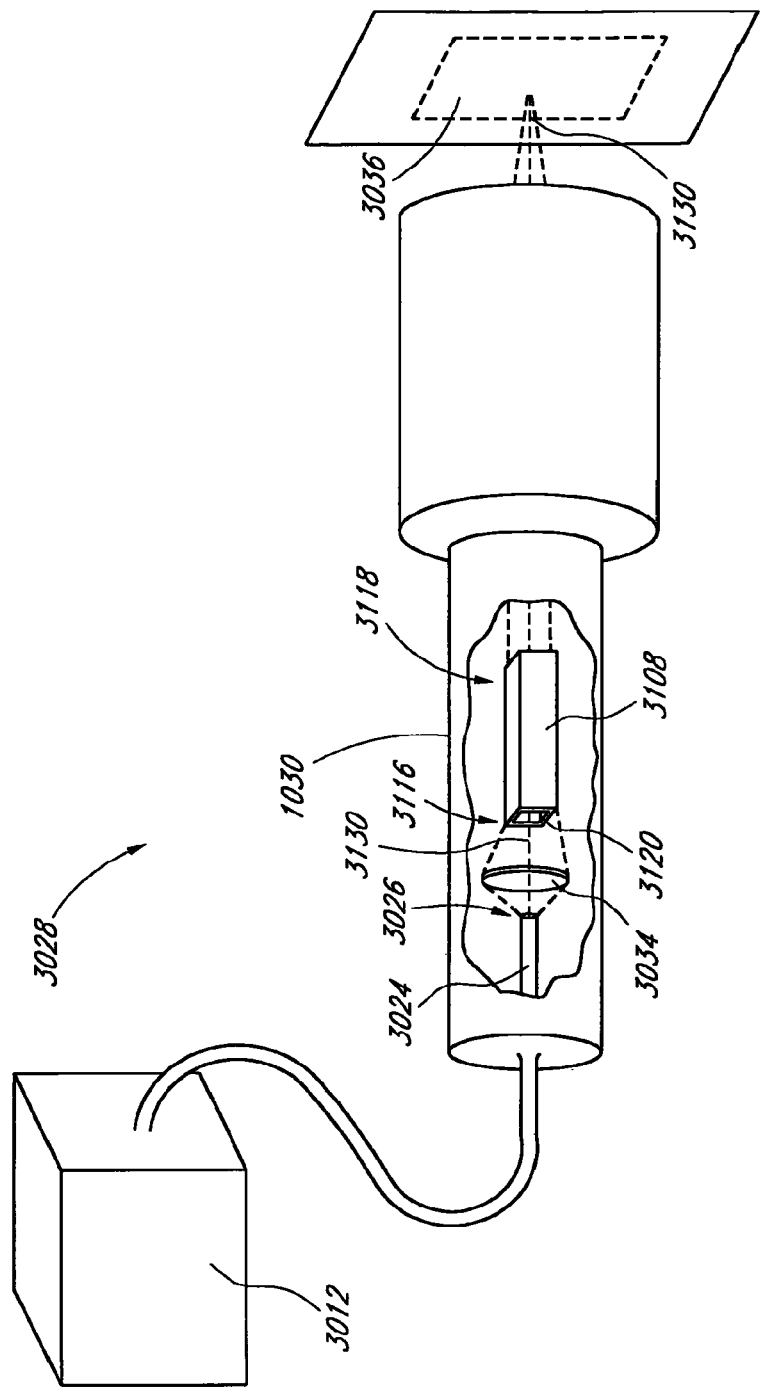

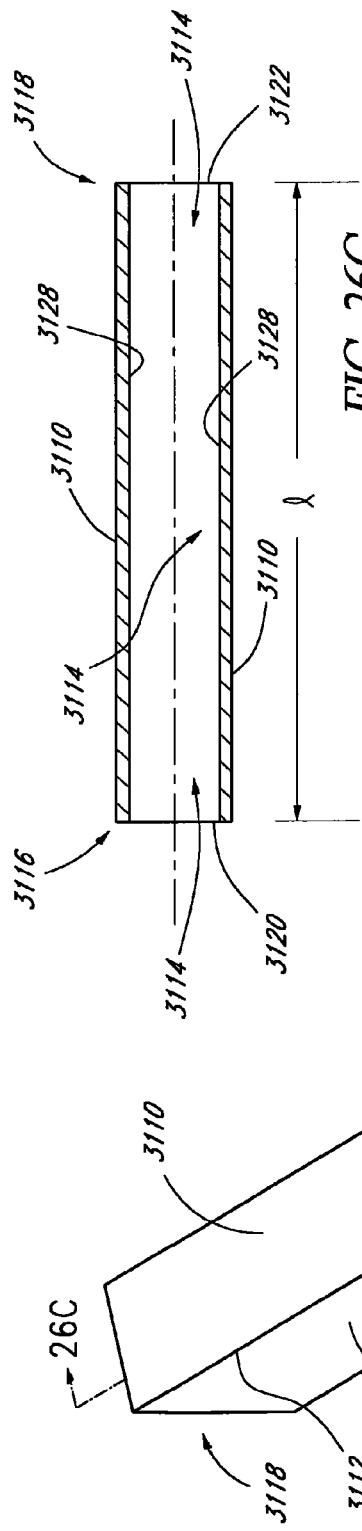
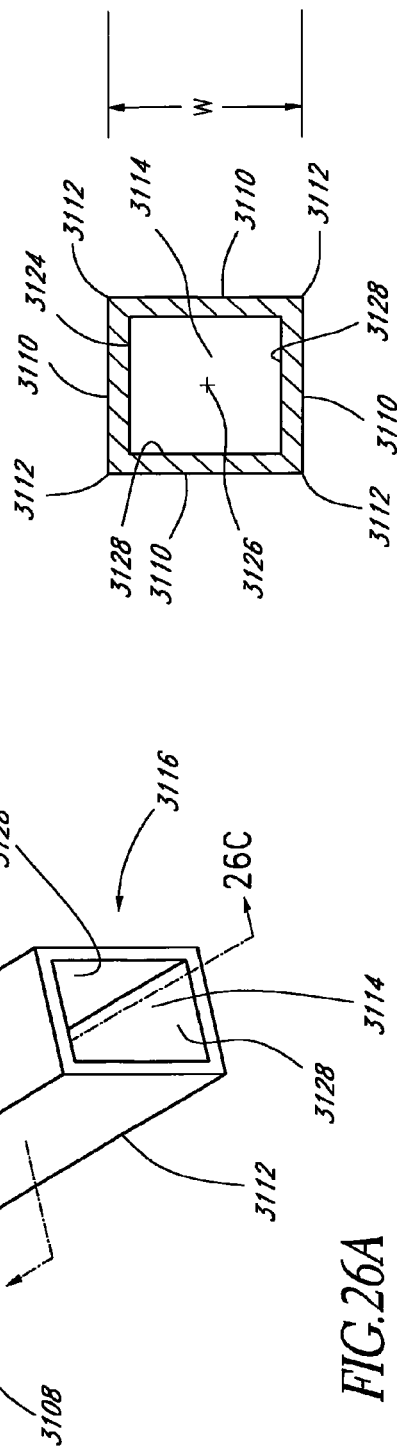
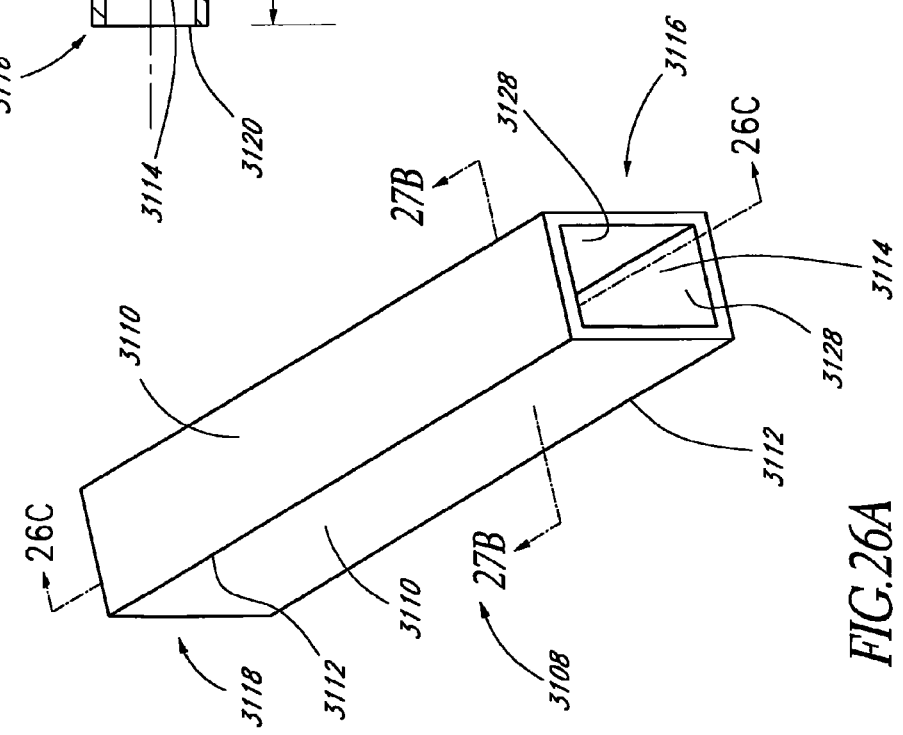
FIG. 26C
FIG. 26B
FIG. 26A

DEVICE FOR UV PHOTO-THERAPY

PRIORITY APPLICATION

This application is a continuation of U.S. patent application Ser. No. 11/429,695, filed May 8, 2006, which is a continuation U.S. patent application Ser. No. 10/462,375, filed Jun. 16, 2003 and issued as U.S. Pat. No. 7,144,248 on Dec. 5, 2006, which is a continuation of U.S. patent application Ser. No. 10/274,838, filed Oct. 18, 2002 and now abandoned, which claims priority under 35 U.S.C. §119(e) from U.S. Provisional Patent Application Ser. No. 60/336,337, filed Oct. 18, 2001. The present application incorporates each of the foregoing disclosures herein by reference in its entirety.

BACKGROUND OF THE INVENTION

1. Field of the Invention

The present invention is directed to apparatus and methods for treating tissue with ultraviolet light.

2. Description of the Related Art

Skin disorders, including atopic dermatitis, dyshidrosis, eczema, lichen planus, psoriasis, and vitiligo, are conditions that commonly affect large populations at some time in their lives. For example, about 2% to 3% of the population of northern Europe is estimated to be afflicted with psoriasis. Although the disease's prevalence in the United States is not as well understood, it appears that between 150,000 and 260,000 new cases are diagnosed each year. This suggests that at least several million people suffer from the disease in the United States.

Psoriasis can range in severity from relatively mild, with some drying and flaking of the affected skin, to severe cases with very severe outbreaks over large areas of the patient's body. Even very mild psoriasis is uncomfortable and unsightly. Severe cases can be physically and psychologically debilitating, presenting a very serious threat to the patient's overall health.

Although the underlying mechanisms of psoriasis are not yet perfectly understood, the disease involves abnormally rapid cell proliferation in the basal layer of the skin. This hyperproliferation can be reduced and the disease ameliorated with what is conventionally known as "phototherapy," i.e., by exposing the affected skin surface to a source of light, in particular, ultraviolet light. Phototherapy can be performed simply by exposing the patient to natural sunlight, or in a more controlled way by applying light from an artificial source to the affected areas.

Commonly, a patient may be exposed over substantially his or her entire body, or at least a very large portion of it, to artificial light from an electric lamp or a similar source generating light having a significant ultraviolet component. While this mode of treatment has been effective, it is less than optimal. In recent times patients and physicians have become increasingly aware of the undesirability of unnecessary exposure to ultraviolet light. Ultraviolet light causes damage to the skin and premature aging; it is also associated with melanoma and skin cancer. Additionally, conventional phototherapy treatment is implemented over an extended time and requires the patient comply to a regimen involving frequent visits to the physician before experiencing even slight improvement in his or her condition. Following such regimen is inconvenient to the patient as well as costly; furthermore treatment often fails due to lack of compliance to this regimen. Thus, what is needed is a treatment for psoriasis and other skin or tissue disorders that reduces side effects such as the risk of melanoma and skin cancer and that effectuates a rehabilitation of disease tissue expeditiously.

SUMMARY OF THE INVENTION

One aspect of the invention comprises an optical apparatus for treating tissue in a mouth of a human being. The apparatus comprises an ultraviolet light source that emits UV light having an intensity of at least about 1 MED, an optical fiber, and an elongate member for insertion into the mouth. The optical fiber has a proximal end that receives the UV light from the ultraviolet light source and a distal end that outputs the UV light to expose the tissue in the mouth to the UV light. The elongate member for insertion in the mouth comprises an outer material substantially non-reactive to saliva. The elongate member has proximal and distal ends and an inner channel for directing the UV light from the proximal end to the distal end and onto a region of the tissue for exposure to the UV light.

Another aspect of the invention comprises a method of treating a region of tissue within a mouth. In this method, ultraviolet light having an intensity of at least about 1 MED is propagated through an optical fiber. The UV light is coupled from the optical fiber into an elongate member having a channel therein. A beam is produced having a substantially uniform intensity profile that is output through an exit aperture of the channel. This beam has an intensity that is substantially constant across the exit aperture. The elongate member is inserted in the mouth and is positioned with respect to the region of tissue in the mouth to direct the substantially uniform intensity beam on the tissue so as to provide substantially uniform ultraviolet illumination over the region of tissue.

BRIEF DESCRIPTION OF THE DRAWINGS

Preferred embodiments of the present invention are described below in connection with the accompanying drawings.

FIG. 8 is an exploded view depicting internal views of the delivery device of FIG. 2;

FIG. 9 is an exploded view showing parts of the delivery device shown in FIG. 3;

FIG. 25 depicts a delivery device that includes an optical fiber, a lens, and a conduit for directing light onto a target area;

FIGS. 26A-26C depict perspective and cross-sectional views of a rectangular conduit for use in a delivery device such as shown in FIG. 25;

DETAILED DESCRIPTION OF THE PREFERRED EMBODIMENT

These and other embodiments of the present invention will also become readily apparent to those skilled in the art from the following detailed description of the preferred embodiments having reference to the attached figures, the invention not being limited to any particular embodiment(s) disclosed. Accordingly, the scope of the present invention is intended to be defined only by reference to the appended claims.

Deleterious effects of various skin or tissue disorders including atopic dermatitis, dyshidrosis, eczema, lichen planus, psoriasis, and vitiligo can be ameliorated by directing high doses of ultraviolet light onto areas of skin/tissue affected by the disorder. The effectiveness of this technique utilizing ultraviolet light depends in part on wavelength, dosage, and what region of skin or tissue is exposed to the ultraviolet light.

Figure 1:
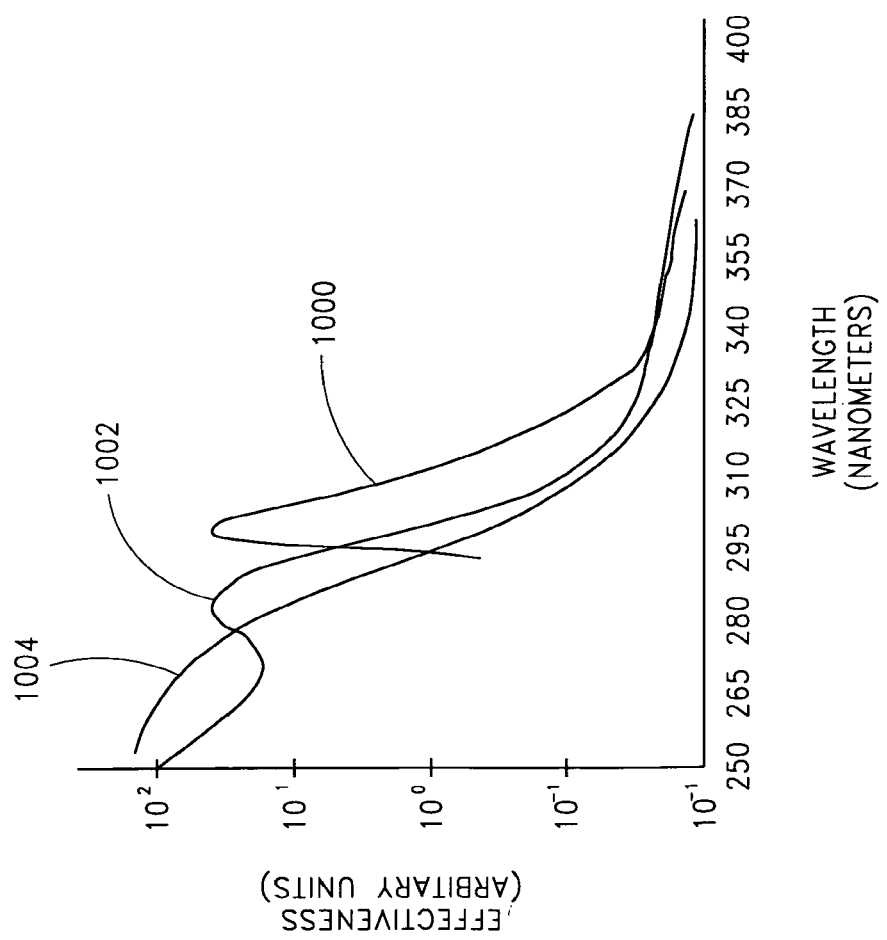
FIG. 1 depicts a plot on axis of wavelength (in nanometers) and effectiveness in arbitrary units of the psoriasis action spectrum, human erythema action spectrum, and the action spectrum for DNA damage (i.e., carcinogeneity)

Light within a specific range of wavelengths has been determined to be both effective in rehabilitating diseased skin and also in avoiding harmful side effects such as cancer and erythema (i.e., sunburn). This wavelength range coincides with a spectrum conventionally known as UV-B, which extends in wavelength from approximately 280 or 290 to approximately 315 or 320 nanometers. The wavelength of light that is most successful at treating affected skin areas without causing harmful side effects is defined with reference to action curves 1000, 1002, 1004 for psoriasis, for erythema and for carcinogeneity, which are shown in FIG. 1. Psoriasis afflicted tissue can be effectively rehabilitated with light having wavelengths between approximately 300 to 310 nanometers. As shown by the psoriasis action spectrum curve 1000, light having a wavelength spectrum between about 295 or 300 and about 320 or 325 nanometers can be effective in healing the tissue as well, but to a lesser extent. Incidence of erythema and skin cancer, as shown by the respective action spectrum curves 1002, 1004, however, increases in general for shorter wavelengths in this range between 295 and 325 nanometers. Risk of skin cancer, for example, is significantly higher for wavelengths at and below about 295 to about 300 nanometers than for wavelengths above this range. Erythema is also more readily produced by light having a wavelength of 290 nanometers than light between about 300 to 310 nanometers in wavelength. Therefore, to provide optimal treatment preferably diseased skin on a patient is exposed to light having wavelength that maximizes a likelihood of healing of diseased tissue yet reduces risk of erythema and DNA damage, i.e., cancer. Accordingly, light ranging, for example, between about 295 to about 315 or 320 nanometers and more specifically, between about 300 to about 310 nanometers is preferred.

High, not low doses of light within these preferred ranges of wavelength have been determined to be most desirable. Diseased skin exposed to high doses of light heals quicker, that is, a fewer number of high dose treatments are required in comparison to conventional, low dose phototherapy treatments. Significant advantages derive from reduction in number of treatments. Since less treatments are necessary for high dose treatments, the total quantity of UV-B light to which skin is exposed to achieve healing is substantially smaller than for low dose treatments. This dosage can be quantified in total number of photons, or in total amount of energy such as in units of Joules. For example, preferably at least about 500 milliwatts (mW) of light having a wavelength of between about 304 and about 310 nanometers is directed onto the diseased tissue. It is well known that the risk of cancer and skin damage depends on the total number of photons or amount of UV-B radiation directed on the skin. Thus, by raising the dosage in a single treatment and thereby reducing the number of treatments, the overall UV light exposure and thus the risk of cancer and other skin damage is lowered. Additionally, lower number of treatments may also provide a higher degree of compliance of a patient to an otherwise difficult regimen involving a significant number of visits to the physician. Such a simplification in treatment is favorable as patients are less willing or able to adhere to a regimen involving multiple treatments per week for months.

In light of the foregoing reasons, doses as high as a patient can tolerate are preferred. More particularly, dosages at least as high as 1 minimum erythema dose (MED) have proven to be extremely advantageous. As defined herein a minimum erythema dose or MED corresponds to the minimal dosage at which a noticeable change in color occurs with distinct edges. The amount of energy necessary to induce redness varies from patient to patient and depends on many factors including race, age, and skin color. Consequently, in treating a particular patient, a level of localized exposure equivalent to 1 MED can be determined for the patient. This level of exposure may be characterized by fluency or the amount of energy delivered to a defined area in, e.g., Joule/cm$^2$. Diseased tissue is thereby exposed to doses at least as high as that dose that creates a change in color bounded by distinct edges on healthy skin is applied. Exposure of 1 MED or higher, i.e., doses of about 2 to about 4 or even to about 6 or 8 MED are effective in remedying the diseased condition. Moreover, a direct correlation has been also observed between occurrence of blisters and particularly successful treatments. For example, levels of exposure to UV radiation as high as 16 to 20 MED, cause UV radiation burns that produce blisters on the skin. However, only a single treatment at this exposure level is necessary to rehabilitate the diseased tissue. Thus, employing dosages that cause UV radiation burns accompanied by blistering appear to yield successful single treatment phototherapy. For these dosage levels, however, the patient should necessarily be able to endure the blistering.

Although the amount of energy that corresponds to 1 MED depends on the skin characteristics of the specific patient, for effective treatment of skin disorders like psoriasis, the recommended fluency of light having wavelengths distributed between about 300 and about 310 nanometers has been determined to range between about 10 milliJoule/square centimeter (mJ/cm$^2$) to about 4.0 Joule/square centimeter (J/cm$^2$). More specifically, the range of fluency preferably ranges between about 100 mJ/cm$^2$ to about 1.8 J/cm$^2$, and more preferably between about 600 mJ/cm$^2$ and about 1.2 J/cm$^2$. Accordingly, doses as high as 500 mJ/cm$^2$, 1 J/cm$^2$, and 1.5 J/cm$^2$ of light having wavelengths at least as large as 300 nanometers but less than or equal to about 310 nanometers may be employed to treat skin disorders. Less doses of shorter wavelength light are required in comparison to longer wavelength of light. For example, fluencies in a range of about 50 mJ/cm$^2$ to about 1 J/cm$^2$ of light with a center wavelength of about 305 nanometer (e.g., between 304.5 and 305.5) may produce similar results as fluencies ranging from about 300 mJ/cm$^2$ to about 4 J/cm$^2$ of light having a wavelength centered about 310 nanometers (e.g., between 309.5 and 310.5). The action spectrum for erythema 1004 dictates in part how the required dose varies with wavelengths. As shown in the action spectrum 1004 depicted in FIG. 1, erythema is more readily induced by shorter wavelengths than longer wavelengths. In particular, the erythema response is about ten times stronger for light having wavelength centered about 305 nanometers (e.g., between 304.5 and 305.5) than for light centered about 310 nanometers (e.g., between 309.5 and 310.5). (Note that effectiveness as plotted in FIG. 1 corresponds to the degree the tissue is affected by one joule of optical energy.)

Since high doses of ultraviolet light enhance the risk of skin cancer and erythema as well as cause other skin damage generally associated with premature aging, the extent of a patient's epidermis to which light is directed are preferably limited. Since the diseased tissue needs to be exposed, light is not delivered to regions of skin other than affected areas, which particularly with psoriasis, are more tolerant to higher doses of light within the preferred wavelength regions than is healthy tissue. In treating psoriasis, for example, the UV light is preferably directed onto the lesional as well as surrounding paralesional tissue, which although appearing normal is diseased tissue. Treatment, however, is preferably restricted only to these affected areas of skin, and areas uninvolved are preferably not exposed to the ultraviolet light. Certainly, the patients entire body is not subjected to the ultraviolet light as is true in some conventional phototherapy treatments. Instead, the ultraviolet light is preferably delivered to each separate affected region of the body. By avoiding treatment of unaffected portions of skin, the dosage can be raised well above conventional dosages as the affected areas will tolerate substantially higher doses without increased risk of side effects. Accordingly, the high doses of UV illumination are directed to an area on the skin that is preferably less than about 3000 cm$^2$, more preferably less than about 1000 cm$^2$, and most preferably less than about 500 cm$^2$.

The temporal extent over which exposure occurs is also important. Exposure of the affected area to the UV light results in heating of the tissue. Unless this heat is sufficiently dissipated, thermal blistering will result. In particular, blisters are formed if the temperature of the skin is raised to about 50° C. Thermal energy absorbed by the exposed portion of skin, which may reach a depth between about 5 and 100 micrometers (μm), is preferably conducted away from that region before it heats up the skin to excess. Specifically, the region preferably does not heat up to the critical temperature of about 50° C. or more which would result in the formation of thermal blisters. Whether the thermal energy is sufficiently dissipated depends in part on the thermal time constant $\tau_{THERMAL}$ of the skin, which governs the rate of heat dissipation. The rate at which thermal energy is introduced into the skin is also a relevant factor. Preferably, therefore, the high dose of energy provided by the UV light is distributed over a length of time greater than one or two times the thermal time constant associated with the removal of heat from the tissue. This duration of exposure may for example range between about 500 milliseconds (msec) and 1500 milliseconds for radiation delivered at 308 nanometers at fluences of less than 1 W/cm$^2$. The illumination is preferably within a short enough time to be practical yet long enough to prevent blistering cause by thermal overload.

An excimer laser can generate short high power pulses of light having a waveglength of about 308 nanometers. These pulses can be high in power, e.g. about a half a million watts, but short in duration, for example, maybe lasting much less than 100 nanoseconds (e.g., 30 nanoseconds). The laser, however, may produce a plurality of such pulses at a repetition rate of about 200 Hz, i.e., one pulse per 5 milliseconds. Tissue exposed to a plurality of these short pulses will increase in temperature slightly with application of each pulse. The cumulative effect of the plurality of pulses being to raise the temperature of the tissue an amount that depends in part on the heat capacity of the tissue. The heat capacity is directly related to the thermal time constant $\tau_{THERMAL}$ of the skin described above, which governs the rate of heat dissipation of heat from the skin after the series of pulses is complete. Preferably, therefore, the energy from the laser is spread over a long enough period of time with respect to the length of the thermal time constant $\tau_{THERMAL}$ so as to permit sufficient dissipation to avoid excessive build-up of heat from the plurality of short pulses. Thermal damage caused by raising the temperature of the skin above, for example, the blister temperature of 50° C., can thereby be prevented. The amount of time required to expose the affected tissue to the therapeutic doses of UV light, however, depends on the particular dose level.

Figure 2:
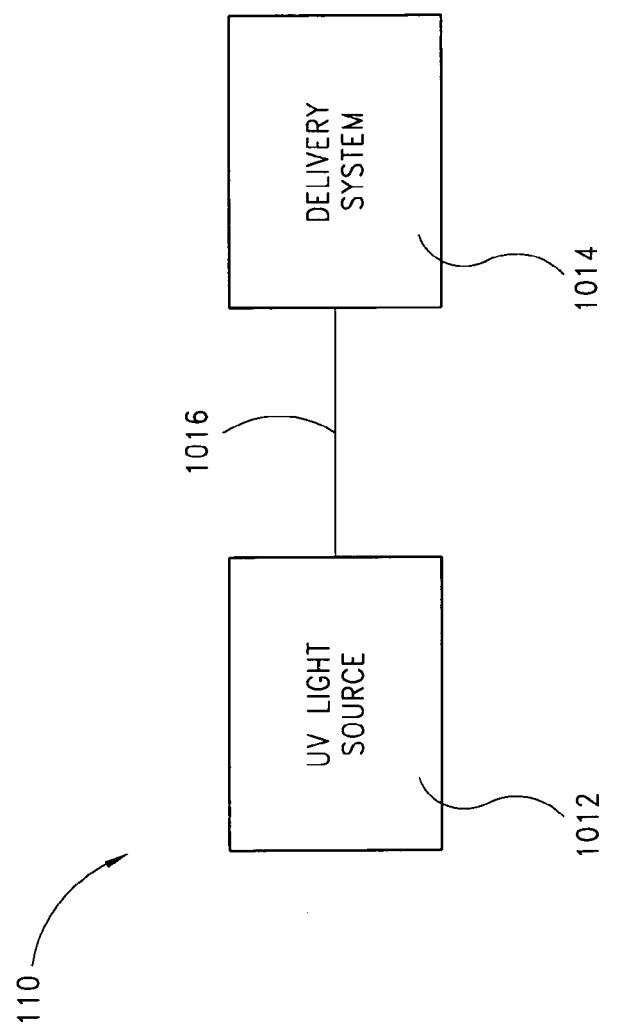
FIG. 2 shows a block diagram of a preferred embodiment for treating skin disorders.

This phototherapy treatment can be accomplished by utilizing an apparatus 1010 comprising an ultraviolet light source 1012 and a delivery system 1014 such as illustrated in block diagram form in FIG. 2. The ultraviolet source 1012 may comprise a laser, a lamp, or a solid-state device such as a light emitting diode. One or more of such light sources 1012 may be used alone or in combination with other similar or different light sources to produce light of sufficient intensity and at the appropriate wavelength to treat the skin disease. An excimer laser, and more specifically, a XeCl gas laser outputting light having a wavelength of about 308 nanometers, or an arc lamp or fluorescent lamp that provides radiation within the UV-B region are particularly suitable light sources for this application. A filter may be included to remove light outside the preferred wavelength ranges. This filter may comprise a dichroic or dielectric filter or a grating.

The delivery system 1014 may comprise a hand device that can be readily handled and moved to direct light onto the affected areas skin. Alternately, the delivery system 1014 may comprise a scanner possibly computer controlled, such as one that utilizes minors or reflective surfaces that move and thereby translate a beam of ultraviolet light extracted from the light source. A spatial light modulator, an optical component having a surface comprising a plurality of smaller regions each of which can independently be set to either transmit or block a portion of light incident on the surface of the modulator, may also be employed to appropriately distribute the ultraviolet light onto the patient's skin. Such spatial light modulators as are currently available, as well as those yet devised, include ones that switch mechanically, and ones that accomplish switching by altering the polarization of light passing therethrough.

The delivery system 1014 is preferably adapted to deliver the high dose to a target region of skin spanning between about 300 to 700 cm$^2$ or more preferably between about 400 and 650 cm$^2$. The delivery system 1014 may include a focusing element such as a lens or mirror for focusing the optical beam down to a small region. Alternatively, the delivery system 1014 may have an aperture for egress of the UV light to limit beam size. For example, this aperture may be a square aperture with sides that restrict the size of the beam.

An optical path 1016 provided for example by an optical waveguide may channel light from the light source 1012 to the delivery system 1014. This optical waveguide may comprise an optical fiber bundle including a plurality of fibers comprising material transparent to UV-B radiation such as quartz or fused silica. The optical fiber line 1016 may include a liquid filled optical guide such as shown in U.S. Pat. No. 4,927,231 issued to Jeffrey I. Levatter on May 22, 1990, which is hereby incorporated herein by reference in its entirety. This liquid filled optical guide is especially suited to transfer large amounts of optical power. The power-handling capability of the optical components within the apparatus 1010 are particularly important given that doses of 1 MED or higher are being applied to the patients skin.

In particular, the ultraviolet light source 1012 and the delivery system 1014 as well as the optical path 1016 preferably are able to handle power levels high enough to provide therapeutic doses of 1 MED or more. The prolonged duration over which the skin is exposed to the UV light, however, mitigates against the necessity for excessively high power requirements for these and other components in the apparatus 1010. As discussed above, the energy density delivered to the patient is preferably in a range of about 205 to about 1200 mJ/cm$^2$. However, to avoid blistering, the dosing with UV light is extended over a sufficiently long period of time so as to permit the thermal energy to be adequately dissipated. The power is optionally transported by a waveguide or with the aid of any other optical element and delivered by the delivery system 1014. Other optical components such as lenses, mirrors, filters, grating etc. in the optical path of the UV light directed onto the patient are preferably also adapted to handle the levels of power sufficient for successful treatment of the patient.

As discussed above, the apparatus 1010 is preferably adapted to provide doses of UV light over short intervals, e.g., between about 0.5 and 1.5 sec in duration. Such periodic dosing can be provided by including a switch, a modulator, or a shutter within the path of the beam of UV light. For example, electro-optical and acousto-optical modulators, electro-optical and magneto-optical switches, as well as other optical devices that deflect, block, or otherwise interrupt the UV light output from the apparatus can be employed to prevent UV light from reaching the epidermis of the patient. Other alternatives include switching the light source on and off. Optical output from a solid state device such as a laser diode or a light emitting diode can be electrically controlled; accordingly such UV light sources 1012 can be intermittently activated so as to expose the patient over brief intervals. As discussed above, some light sources inherently produce pulsed output. Short pulses of light, for example, are emitted from pulsed lasers or pulsed lamps. Pulsed lasers and lamps that produce UV light are particularly suitable UV light sources. Other UV sources as well as other methods that yield short pulses of UV light for dosing a patient may also be appropriate for use in conjunction with the apparatus.

As discussed above and shown in FIG. 3, the UV light source 1012 may comprise a laser 1020 such as an excimer laser. Preferably, the laser 1020 comprises a XeCl laser that emits light having a wavelength centered about 308 nanometers. Like lasers well known in the art, the laser 1020 includes a gain medium (not shown), e.g. gaseous XeCl, surrounded by two mirrors (not shown), one substantially entirely reflective and the other that is partially transmissive. One end 1022 of an optical line 1024 comprising a waveguide in the form of for example a single optical fiber, an optical fiber bundle or a light pipe, is juxtaposed proximal to the partially transmissive mirror, another distal end 1026 of the optical line 1024 being attached to a delivery device 1028 comprising a hand piece 1030. A coupling lens 1032 is inserted between the partially transmissive minor and the optical guide line 1024. The handpiece 1030 also includes a lens 1034.

Light emitted by the laser 1020 is coupled into the optical line 1024 via the coupling lens 1032. This light propagates through the optical line 1024 substantially without absorptive loss and on into the handpiece 1030, which can be manipulated by the user to direct the UV light onto the portion of the patient's epidermis designated for treatment. The lens 1034 within the handpiece 1030 focuses the UV light onto a small region 1036, one, for example, between about 1 and 4 cm$^2$ in size.

In one embodiment, proximal end 1022 of the optical line 1024 may have a circular cross-section 1038 while the distal end 1026 has a square or rectangular cross-section 1039. The lens 1034 in the handpiece 1030, preferably comprising fused silica, images the square or rectangularly shape distal end 1039 of the optical line 1024 onto the skin of the patient. Accordingly, the region of the skin that is illuminated comprises an area having a square or rectangular shape. The irradiance may be uniform over this square or rectangular area 1036 so as to enable the user to provide a uniform dose to a large area of diseased skin (i.e., larger than the image of the distal end 1026 of the optical line 1024) by employing two methods described below that are herein referred to respectively as the paint and tile methods.

Utilizing a fiber bundle comprising a plurality of fibers as the optical line 1024 is preferable in the case where the coupling lens 1032 cannot focus the UV light down to an area small enough for coupling the light into a single fiber having a small cross-section. The cross-section of the single fiber may be smaller than the cross-section of the beam even after focusing via the coupling lens 1032. The light collected from the UV light source 1012 therefore cannot be efficiently transferred into the single fiber and the amount of light that is coupled into the fiber is inadequate to provide an effective and reasonable treatment for skin disorders. The amount of energy that can be injected into the fiber, as well as into a optical fiber bundle, is equal to the product of the radiance from the light source 1012, the cross-section of the fiber or fiber bundle where the light enters and the numerical aperture of the optical fiber or optical fiber bundle. Since conventional fused silica fibers generally have a numerical aperture of about 0.22, the cross-section of the fiber (or the fiber bundle) is the parameter that can be altered. In particular, this cross-section preferably has an area large enough to receive the entire focused beam from the coupling lens 1032.

A fiber bundle is further advantageous, because it can offer a method for converting a beam profile having a circular cross-section, to one having a square or rectangular cross-section. The proximal end 1022 of the fiber bundle can be configured into a circular geometry, i.e., one having a circular cross-section, while the output end can be shaped into a square geometry with a square cross-section. This arrangement eliminates the need for a specialized optical component such as a specialized light pipe in the handpiece 1030 to act as a diffuser and/or beam shaper thereby reducing the weight and cost of manufacture of the handpiece and at the same time increasing its resistance to damage when dropped.

As discussed above, preferably, the laser 1020 is a pulsed laser. More preferably, the laser 1020 is an excimer laser such as a XeCl excimer laser and outputs light having a wavelength of about 308 nm. Alternatively the laser 1020 may comprise a solid state laser or a dye laser and may be supplemented with wavelength selective device such as one or more filters, gratings, or prisms. These filters may include dichroic or interference filters and may comprise dielectric or metal layers. The wavelength may also be controlled using optical components exploiting non-linear optical properties.

Additionally, UV light source 1020 as employed for the above-described dermatological applications preferably meets certain performance requirements. In particular, to be commercially successful, the apparatus 1010 preferably can operate for at least about one to three months without requiring servicing, a period during which, on average, a physician may treat between about 100 to about 300 patients. Treatment of a single patient may often involve dosing affected tissue, which altogether spans a large portion (e.g., 20 percent) of the patient's entire body, each individual dose, however, being administered over a localized region 1036 of skin, e.g., 1 cm$^2$ for a period in excess of the thermal time constant. Since UV light is preferably separately applied to potentially a large number of different sites on the epidermis, the laser is preferably able to be activated for extended periods of time, e.g., between about 1 to 2 hours total for a single patient, and for between about 100 to about 600 hours for 200 patients over the three month period. Thus, the laser being employed for dermatological applications such as the treatment of psoriasis, atopic dermatitis, dyshidrosis, eczema, lichen planus, and vitiligo preferably has a sufficiently long lifetime so to offer a practical cost effective solution for handling such medical conditions.

In the case when the light source 1020 for these dermatological applications is an excimer laser, selecting the proper materials to be employed in constructing of the laser are critical. A suitable gas excimer laser such as an XeCl laser, for example, may comprise pressure vessel that contains a halogen gas, first and second electrodes for creating a laser discharge between the electrodes and generating a laser beam between first and second optical components, a fan for circulating the gases, and a heat exchanger for cooling the gas. By utilizing specific materials in fabricating the pressure vessel, the electrodes, the heat exchanger and the fan of the laser, its lifetime can be extended beyond 3600 hours. The criteria for selecting the appropriate materials for the laser can be found in U.S. Pat. No. 4,891,818 issued to Jeffrey I. Levatter on Jan. 2, 1990, which is hereby incorporated herein by reference in its entirety. In particular, portions of the pressure vessel, first and second electrodes, fan and heat exchanger that are in contact with the halogen gas are fabricated entirely of a material that reacts with the halogen gas to form stable reaction products having a vapor pressure of less than $10^{-6}$ ton at normal operating temperatures. According, the contamination of the gas by the pressure vessel, first and second electrodes, heat exchange, and fan is reduced and the lifetime of the excimer laser is increased. Electrically-conductive portions of the pressure vessel, first and second electrodes, fan and that exchanger that are exposed to the halogen gas may be formed of alumina, e.g. high purity alumina, while non-electrically-conductive portions of the pressure vessel, first and second electrodes, fan and that exchanger that are exposed to the halogen gas are formed of nickel, e.g., high purity nickel, stainless steel or aluminum, e.g., polished aluminum or polished stainless steel. By utilizing these types of materials that react with the halogen gas to form stable reaction products having a vapor pressure of less than $10^{-6}$ torr at normal operating temperatures, an excimer laser light source can be realized that is suitable for dermatological applications, i.e., that can withstand extensive usage over an extended period of time of from about one to three months.

As discussed above and shown in FIG. 4, the light source 1012 may comprise a lamp 1040, in particular an arc lamp, such as a mercury arc lamp, like Model No. 69175 made by Osram Sylvania Products Inc., 275 West Main Street, Hillsboro, N.H. 03244. Other lamps 1040 that produce ultraviolet radiation in the range of between about 302 to 310 nanometers include germicidal lamps available from Philips Lighting Co., 200 Franklin Square Drive, Somerset, N.J. 08875, deuterium arc lamps, which emit much of their energy below 300 nanometers and require additional filtering, and metal halide lamps, e.g., those available from Fusion UV Systems Inc., 910 Clapper Road, Gaithersburg, Md. 20878. Another alternative includes zirconium arc lamps available from Osram Sylvania Products Inc., which emit substantial amounts of energy in the 302 to 310 region of the electromagnetic spectrum from a small volume.

In the apparatus 1010 shown, a reflector 1042 having a reflective surface 1044 is located on one side of the arc lamp 1040. The reflector 1042 may have a spherically, parabolically, or ellipsoidally curved surface 1044 that is reflective for UV wavelengths of light preferably between about 300 to about 315 nanometers and that has an optical axis which passes through the arc lamp 1040.

On another side of the lamp 1040 is a UV filter 1046 such as an interference or dichroic filter followed by a focusing lens 1048 and delivery device 1014 that includes an optical fiber bundle 1050. Preferably, the filter 1046, focusing lens 1048, and fiber bundle 1050 are located on the optic axis of the reflector 1042. Note that in place of the reflector 1042, a lens (not shown) comprising e.g., fused silica, can be employed to collect light from the arc lamp 1040 and instead of the filter 1046, a prism or grating may be utilized for wavelength selection. For example, two passes through a diffraction grating in series can be used to select a narrow bandpass at any location on the lamp emission spectrum with the advantage of being wavelength-stable over broad operating temperature ranges and over production numerous runs. Alternatively, two identical 302 nanometer dielectric filters stacked consecutively may narrow the spectrum; however dielectric filters operating near their cut-on edge are sensitive to changes in temperature and also vary from one production run to another.

The delivery device 1014 may comprise a handpiece 1052 which has an output tip 1054 and that contains the optical fiber bundle 1050. A disposable or steralizable tip 1056 may prevent the output tip 1054 from contacting the patient. The fiber bundle 1050 may comprise silica, quartz, or a liquid filled fiber optic. The fiber bundle 1050 has one end 1058 which may serve as the output tip 1054 of the handpiece 1052 or may be imaged and/or focused onto the patient with another lens (not shown) in the handpiece. This end 1058 of the fiber bundle 1050 may be square or rectangular so as to produce a square or rectangular beam profile that is directed onto the patient in order to facilitate administration by the physician or health care provided a uniform coverage over the affected tissue.

Light from the arc lamp 1040 is collected by the reflector 1042 whose curved reflective surface 1044 is preferably dichroic and reflects predominantly light having wavelengths between about 300 to about 315 nanometers or 300 and 310 nanometers. Light from the arc lamp 1040 radiates toward the reflective surface 1044, reflects therefrom and through the dichroic filter 1046. A portion of the light is also radiated from the arc lamp 1040 and toward the filter 1046 directly. This radiation also passes through and is filtered by the dichroic filter 1046. Radiation from the arc lamp 1040 that is transmitted through the filter 1046 reaches the focusing lens 1048 which couples it into the optical fiber bundle 1050 where it exits therefrom at the output tip 1054 of the handpiece 1052. This light is directed onto the patient. Preferably, the lamp 1040 outputs sufficient power such that after losses within the apparatus 1010, approximately 0.5 to 2.0 W of power exits from the handpiece 1052 and is directed onto the patient.

The optical filter 1046 or filters are used to restrict treatment to a band between about 300 and 315 nanometers. Lamp energy below 300 nanometers is strongly rejected by the optical filter(s) 1046 to prevent erythemal burning and/or carcinogenic effects. Lamp energy above 315 nanometers induces a sensation of heating and is also removed by filtering to ensure patient comfort. Employing broadband light, such as for example that includes wavelengths between about 300 and 315 nanometers, as opposed to using a single intense spectral line, e.g. the 312 nanometer line, captures a substantial percentage of the UV energy emitted by the arc lamp. Limiting treatment to only a single narrow line such as the 312 nanometer line has the disadvantage that the phototherapy response to this line is nearly twenty times less than the response for light having a wavelength of 302 nanometers. Advantageously, a spectral band of between about 302 to 315 nanometers exploits the higher phototherapy response of the shorter wavelengths such as between about 302 and 305 nanometers as well as the higher spectral emittance obtained for wavelengths ranging between about 305 and 315 nanometers. The apparatus 1010 with a mercury arc lamp, for example, therefore has the potential of treating a much larger area of skin in the same amount of time as an XeCl laser if large lamps or efficient optical collectors are employed.

Figure 5:
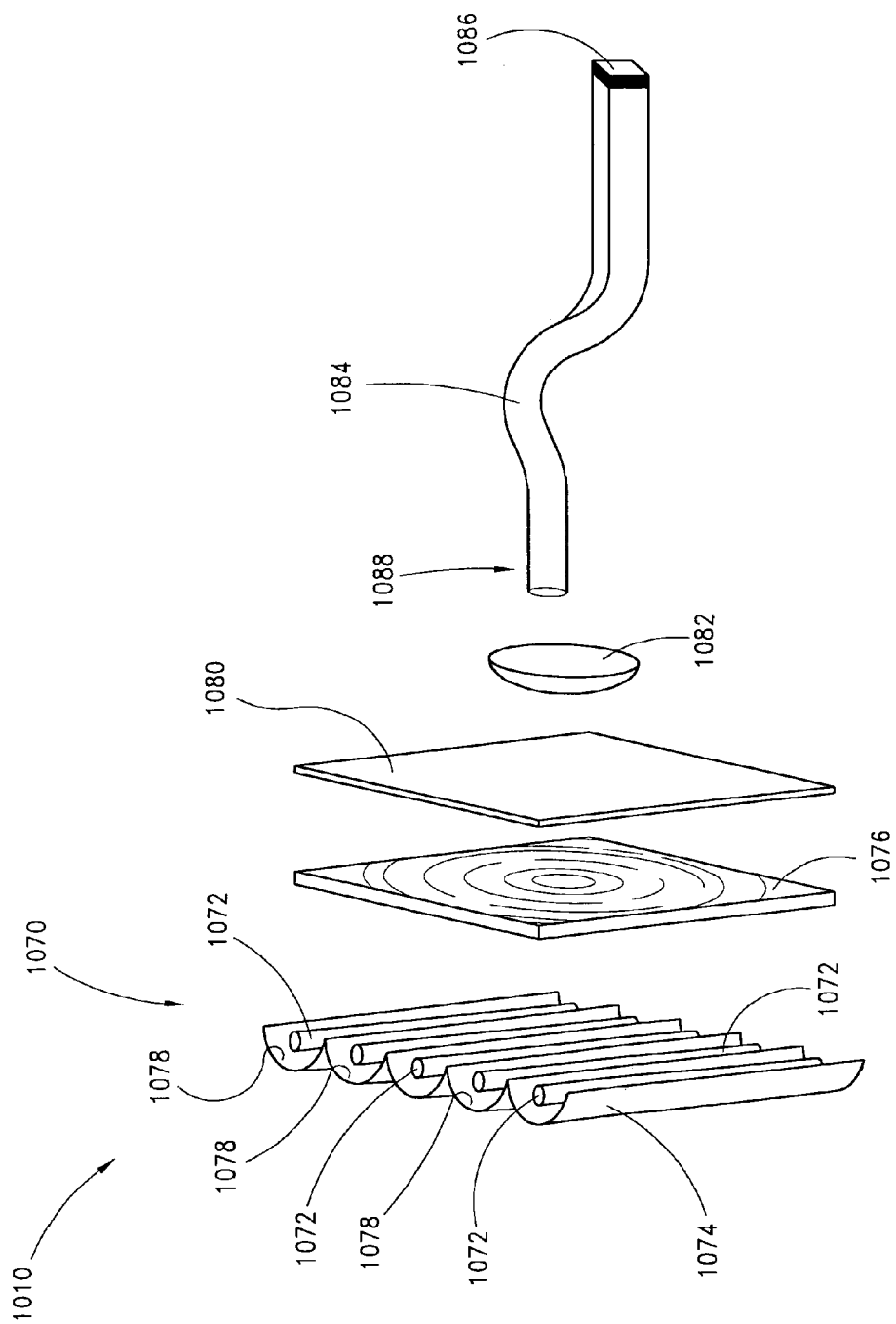
FIG. 5 depicts a schematic view of one embodiment of the present invention comprising a plurality of fluorescent lamps, a reflector, and a filter for directing UV-B wavelength light to the diseased skin.

As depicted in FIG. 5, the light source 1012 may comprise a bank or group 1070 of small fluorescent lamps 1072 such as the Philips CLEO compact lamp or the Phillips TL 40W/10R, which emits a moderate amount of energy in the range of between 300 and 310 nanometers; both lamps are available from Philips. The bank 1070 of fluorescent lamps 1072 is sandwiched between a reflector 1074 located on one side and a lens 1076, here, a fresnel lens located on an opposite side of the lamps. The reflector 1074 comprises a plurality of curved reflective surfaces 1078, one associated with each of the fluorescent lamps 1072 in the bank 1070. These curved reflective surface 1078 may for example have cross-sections that form a segment of a circle, a parabola or an ellipse. Adjacent the fresnel lens 1076 is a wavelength selective filter 1080 followed by another lens 1082, here a small refractive lens having sufficient power and being properly positioned so as to provide focusing. An optical fiber bundle 1084 with an output tip 1086 is also included in the apparatus 1010.

Ultraviolet radiation from the lamps 1072 is collected by the reflector 1074 and the fresnel lens 1076 and passes through a wavelength selective filter 1080. The filtered light is focused onto one end 1088 of the optical fiber bundle 1084 by the focusing lens 1082 and is transmitted through the length of the fiber bundle and exits from the output tip 1086 of the fiber. The apparatus 1010 may be made quite small by employing small fluorescent bulbs 1072. If the apparatus 1010 is sufficiently small and lightweight, the fiber optic bundle 1084 can be eliminated and the apparatus 1010 can be aimed or scanned by the user over the patient's affective areas of skin.

Moreover, although each of the systems 1010 described above and depicted in FIGS. 3-5 may include optical fiber bundles, as indicated, the systems are not so limited. For example, single or plural optical fibers or light pipes and/or other waveguide devices can be employed. Alternatively, the UV light may propagate in free space over a path which may or may not be manipulated by optical elements located in that path.

EXAMPLE

Figure 6:
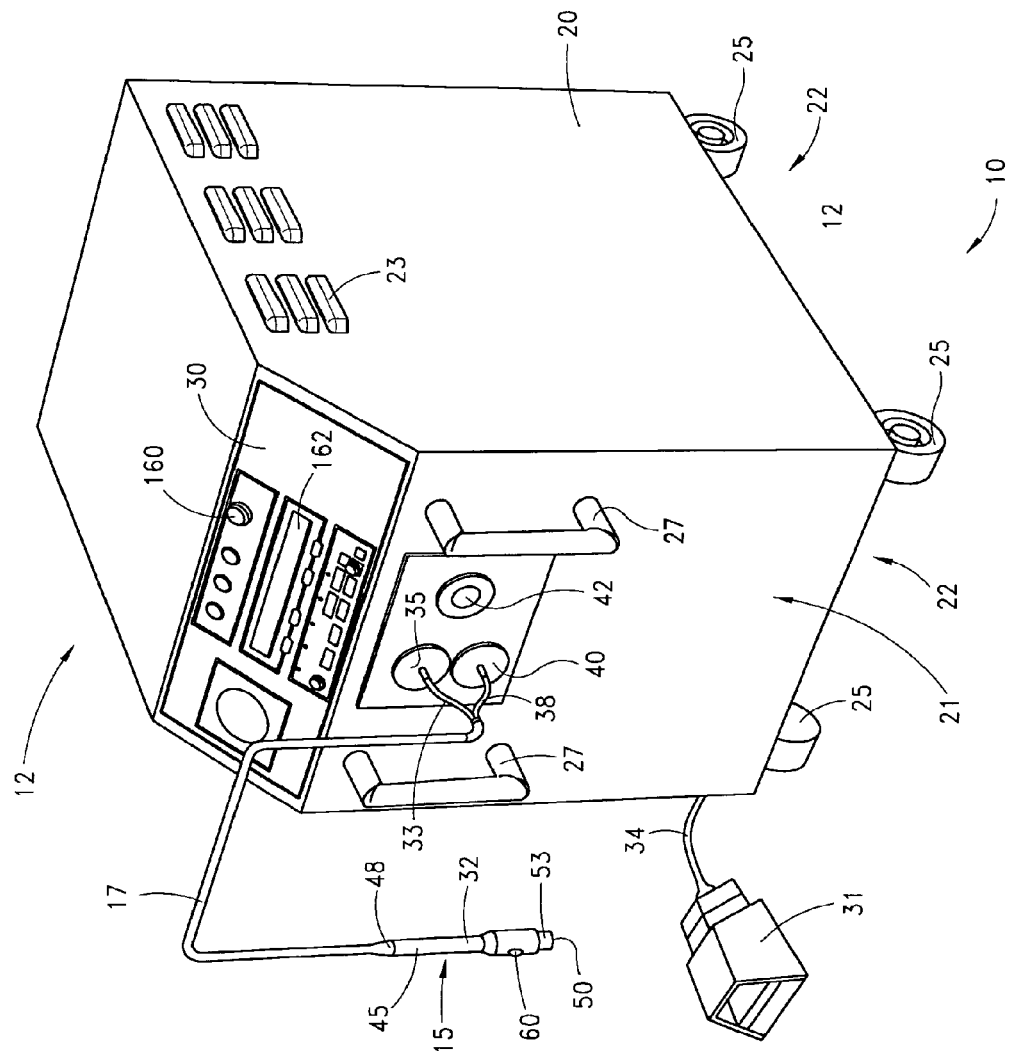
FIG. 6 shows one example of a laser system employed to direct UV-B wavelength light of sufficient energy to effectively treat skin disorders like psoriasis.

Another example of an apparatus 10 suitable for delivering electromagnetic energy to treat a skin condition in a medical patient is depicted in FIG. 6. The apparatus 10 comprises an ultraviolet light source 12 and a delivery device 15. A cable 17 connects the delivery device 15 to the UV light source 12 so that energy from the UV light source can be delivered through the delivery device to the skin of a medical patient. The apparatus 10 is powered from an external electrical power source through a suitable electrical cable (not shown), which plugs into a typical, grounded wall socket.

In a preferred embodiment, the UV light source 12 is a 308 nanometer XeCl excimer laser. The 308 nanometer energy output is within the UVB range (i.e., about 290 to 320 nanometers) of ultraviolet light which, as described above, is therapeutically useful in the treatment of psoriasis. This generator 12 produces ultraviolet light pulses with an energy content of about 15 millijoules per pulse. Individual pulses have a duration of about 30 nanoseconds (full width at half maximum intensity) and the pulses are repeatable at frequencies between about 100 and 150 Hertz.

The UV light source 12 is contained inside a housing 20 with a front 21 and bottom 22. One or more fans (not shown) assist in cooling the excimer laser by forcing air through air vents 23 on the exterior of the housing 20. The UV light source 12 is movable on wheels or casters 25 on the bottom 22 of the housing 20. Handles 27 on the front 21 of the housing assist in moving the UV light source 12. A control panel 30 on the front 21 of the housing 20 allows a user of the system 10 to set and adjusts the operating parameters of the UV light source 12. Operation of the system 10 is controlled by a user by means of a foot pedal 31, which can be placed on the floor adjacent the UV light source 12 and which is electrically coupled to the light source 12 by means of a foot pedal cable 34. Operation of the system 12 to deliver therapy to a patient is described more fully below.

The delivery device 15 comprises a hand-held wand 32. This wand 32 is optically coupled to the UV light source 12 by means of the cable 17, which includes a fiber optic delivery cable 33 configured to conduct ultraviolet light emitted by the excimer laser down the cable to the wand. The optical fiber cable 33 in the cable 17 connect to the UV light source 12 at an output connection 35 on the face 21 of the housing 20. A second return fiber optic cable 38 connects to a return connection 40 on the housing 20 in the vicinity of the output connection 35. A calibration port 42 is also disposed on the front face 36 of the housing 20 and is sized to receive the wand 32 therein.

Figure 7:
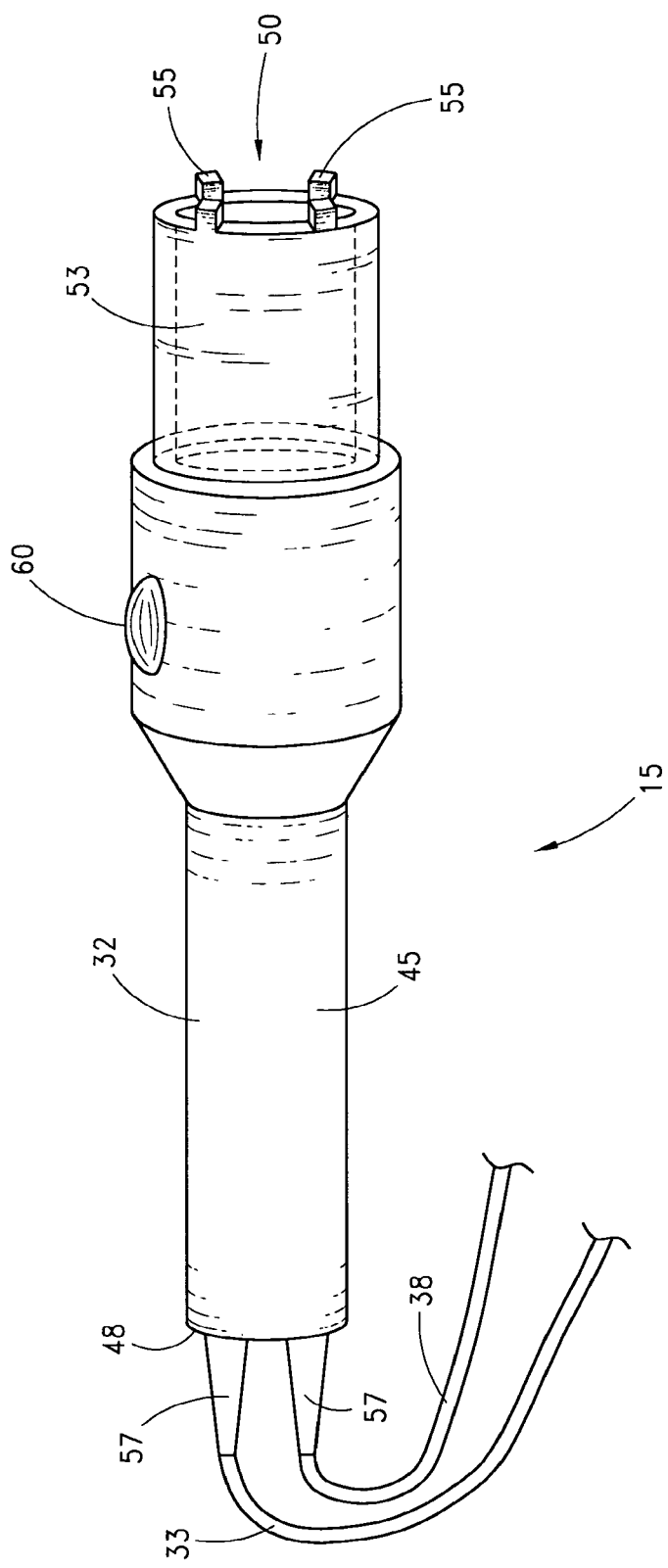
FIG. 7 shows a delivery device that forms a part of the apparatus depicted in FIG. 1.

Exterior details of the hand-held wand 32 are shown in FIG. 7. The wand 32 comprises an elongate, generally cylindrical body member 45 that includes a connecting end 48 and a delivery end 50. A clear plastic cylindrical shield 53 is insertable into the delivery end 50 of the wand. The end of the shield 53 opposite the body 45 of the wand 32 includes positioning nubs 55, which are intended to bear against the patient's skin as energy is being delivered to the patient. The use and function of the positioning nubs 55 are described in more detail below. Preferably, the shield 53 is removable from the wand 32 and disposable, or at least conveniently sterilizable, so that the wand itself is reusable indefinitely between multiple patients.

Still referring to FIG. 7, the delivery cable 33 and return cable 38 connect to the connecting end 48 of the wand 32. The cables 33, 38 connect to the wand 32 through a pair of elastomeric connection boots 57, which provide strain relief and guard against kinking of the delivery and return cables. A switch in the form of a pushbutton 60 selectively allows or prevents the emission of ultraviolet energy from the delivery end 50 of the wand 32. The structure, function, and operation of the pushbutton 60 are described in more detail below in connection with FIG. 8.

FIG. 8 is an exploded view showing the constituent parts of the preferred embodiment of the wand 32 through which ultraviolet energy may be delivered to the skin of the medical patient. The wand 32 comprises a main body member 62 and a secondary body member 65. The two body members 62, 65 are held together by screws 68. A spacer 70 maintains an appropriate separation between the main and secondary body members 62, 65 near the connecting end 48 of the wand 32.

A fiber optic delivery line 73 connects to the connecting end 48 of the wand 32 through one of the connection boots 57. The fiber optic delivery line 73 is coupled to a fiber optic delivery connector 75, which connects to a fiber optic delivery adaptor 77, which is in turn screwed into a fiber optic delivery port 80 at the connecting end 48 of the wand 32. These components direct ultraviolet energy from the UV light source 12 (see FIG. 6) and into the wand 32. The ultraviolet energy travels through the wand 32 through a first light pipe or fiber bundle 82 to a shutter assembly 85, the construction and functioning of which will be described in more detail below.

A second light pipe or waveguide 88 runs inside the wand 32 parallel and adjacent to the first light pipe or waveguide 82. The second light pipe or waveguide 88 is optically aligned with a fiber optic return line 90, which connects to the connecting end 48 of the wand 32 through fiber optic return adaptor 93 and a fiber optic return connector 95. The fiber optic return line 90 is routed through a connection boot 57 and returns back to connect to the return connection 40 on the face of the UV light source 12 (see FIG. 6).

The second pipe or waveguide 88 may be narrower than the first light pipe or waveguide 82 because, while the first light pipe or waveguide is preferably of sufficient diameter to transmit ultraviolet energy of considerable power for effective treatment, the second light pipe or waveguide only transmits a very small amount of energy reflected from the patient's skin back to a detector (not shown) inside the UV light source 12 (see FIG. 6). While energy is being transmitted, energy will be reflected from the patient's skin and detected by the detector. Failure of the detector to detect energy reflected from the patient's skin during energy delivery will most likely indicate a blockage along the light path or some other problem with the delivery or generation system. In that case, the equipment will cease energy delivery and an error message will be delivered to the operator.

During energy transmission, ultraviolet energy from the generator 12 travels through the wand 32 to a shutter assembly 85 inside the wand. Details of the shutter assembly 85 are shown in FIG. 9. The assembly comprises a shutter plate 96, which includes structure defining a relatively large delivery aperture 97, and a relatively smaller return aperture 100. An upper tab 103 at the top of the shutter plate 96 fits into a slot (not shown) in the underside 105 of the pushbutton 60. A shutter plate pin 107 holds the upper tab of the shutter plate 96 in place in the slot of the pushbutton. A compression spring 110 is fitted onto a spring post 112 on the underside of the pushbutton.

The operation of the shutter assembly 85 can best be appreciated by referring once again to FIG. 8, in which the shutter assembly is shown in relation to the other components of the wand 32. A lower tab 115 at the bottom of the shutter plate 96 fits into a slot 116 in a shutter plate retainer 118, which fits into a receiving space 120 within the main body member 62 of the wand 32. The shutter plate retainer 118 is held within the receiving space 120 by a retaining rod 125 and a retaining sleeve 127, or by other suitable means. A tactile feedback member 130 fits within the receiving space 120 just below the shutter plate retainer 118.

When the user wants to deliver ultraviolet energy to a patient's skin, the user presses down on the pushbutton 60, thereby compressing the compression spring 110 against a shelf 132, which partially overlies the receiving space 120 inside the main body member 62 of the wand 32. As the pushbutton is pressed further, the lower tab 115 on the bottom of the shutter plate 96 extends through the slot 116 in the shutter place retainer and presses down against the tactile feedback member 130. The tactile feedback member is made of spring steel or similar suitable material and is configured to produce a "snap" or "click" that is readily noticeable by the user when the pushbutton is fully depressed.

When the pushbutton 60 is fully depressed, the delivery aperture 97 and the return aperture 100 of the shutter plate 96 will be aligned with the first light pipe or waveguide 82 and the second light pipe or waveguide 88, respectively. A pathway is thereby created for ultraviolet energy in a therapeutic amount to travel down the first light pipe or waveguide 82 and through the delivery aperture 97 towards the delivery end 50 of the wand 32. A second pathway is formed simultaneous for the return of reflected energy from the patient, through the return aperture 100, back along the second light pipe or waveguide 88, and ultimately back to the UV light source 12 (see FIG. 6), where the reflected energy will be detected as a return signal by a detector (not shown) inside the UV light source.

When the user releases the pushbutton 60, force from the compression spring 110 returns the shutter plate 96 to a position in which the shutter plate prevents energy from the first light pipe or waveguide 82 from exiting the wand 32. A second pathway is formed simultaneously for the return of reflected energy from the patient, through the return aperture 100, back along the second light pipe or waveguide 88, and ultimately back to the UV light source 12 (see FIG. 6), where the reflected energy will be detected as a return signal by a detector (not shown) inside the UV light source.

When the user releases the pushbutton 60, force from the compression spring 110 returns the shutter plate 96 to a position in which the shutter plate prevents energy from the first light pipe or waveguide 82 from exiting the wand 32. This is a safeguard against accidental release of ultraviolet energy in the event of unintentional activation of the UV light source 12. Should energy be generated inadvertently, the energy will be blocked from exiting the device 15 unless the user has depressed the pushbutton.

When the UV light source 12 is activated with the pushbutton 60 depressed, ultraviolet energy emerges as a beam from the first light pipe or waveguide 82 and travels towards the delivery end 50 of the wand 32. After the beam crosses the shutter plate 96, it enters a lens 135 in the wand 32. From the lens 135, the beam travels through an aperture plate 138, which gives the beam a square cross-section with well-defined edges suited for delivering uniform and well-controlled therapy to the patient. The lens 135 and aperture plate 138 are housed within an optics shell 140 and held inside the optics shell by a retaining ring 142, with the optics shell retained inside the wand 32 by a set screw 145.

Although the pushbutton 60 with aperture plate 138 connected thereto enables the user to further control the application of UV light from the UV light source 12, this feature is not necessary. The apparatus 10 may rely on other arrangements for regulating the short bursts of UV light output therefrom. Many types of light sources, including lasers and flash lamps, can be adapted to output optical pulses of varying duration. Alternatively, electro-optical, magneto-optical, acousto-optical, and even all optical switches and modulators, as well as electrically or magnetically activated mechanical modulators or shutters may be suitably employed to switch the UV output from the apparatus 10 on and off.

Referring still to FIG. 8, the cylindrical clear plastic shield 53 is inserted into the delivery end 50 of the wand 32. The shield 53 bears against an edge 147, which ensures that the positioning nubs 55 on the end of the shield are at proper distance from the lens 135 inside the wand 32. Additionally, the shield 53 is keyed so that the nubs 55 are aligned with the corners of the aperture plate 138, so that the corners of the beam impact the patient's skin substantially at the inner corners of the nubs when the therapy is delivered to the patient. The shield 53 may be keyed for proper insertion into the wand 32, e.g., by the provision of a ridge and a corresponding slot on the wand and the shield.

Soft pads 150 are affixed to the positioning nubs 55 on the end of the plastic shield 53. The shield 53 is sized and positioned so that the corners of the beam are positioned substantially at the nubs 55 on the clear plastic shield. To ensure that the nubs 55 are positioned accurately, the material of the shield 53 is preferably a substantially rigid material. The soft pads 150, which in the preferred embodiment are a relatively soft biocompatible silicone, are affixed to the nubs 55 of the shield 53 to enhance the patient's comfort and avoid injury where the shield contacts the patient's skin. The soft pads 150 also serve to pick up and transfer to the patient's skin small quantities of a suitable biocompatible ink. This assists the caregiver in uniformly applying the ultraviolet energy in a technique that will be described in more detail below. The soft pads 150 may be affixed to the nubs 55 with a suitable adhesive or by any other appropriate means.

Figure 10:
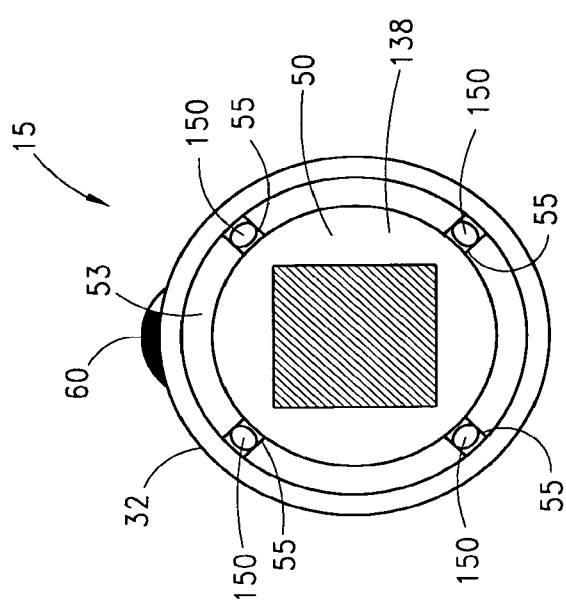
FIG. 10 is an end view showing a delivery end of the delivery device of FIG. 2.

FIG. 10 is a view, end-on, of the disposable shield 53 in place on the delivery end 50 (see FIG. 8 of the wand 32). FIG. 10 also shows the shield nubs 55 that carry the soft pads 150, as well as the aperture plate 138 that forms part of the wand optics. As noted above, the optics of the device 15, and in particular the lens 135, are designed so that the energy beam emerging from the wand 32 has a square-cross section whose corners coincide with the positions of the soft pads 150 on the nubs 55.

Figure 11:
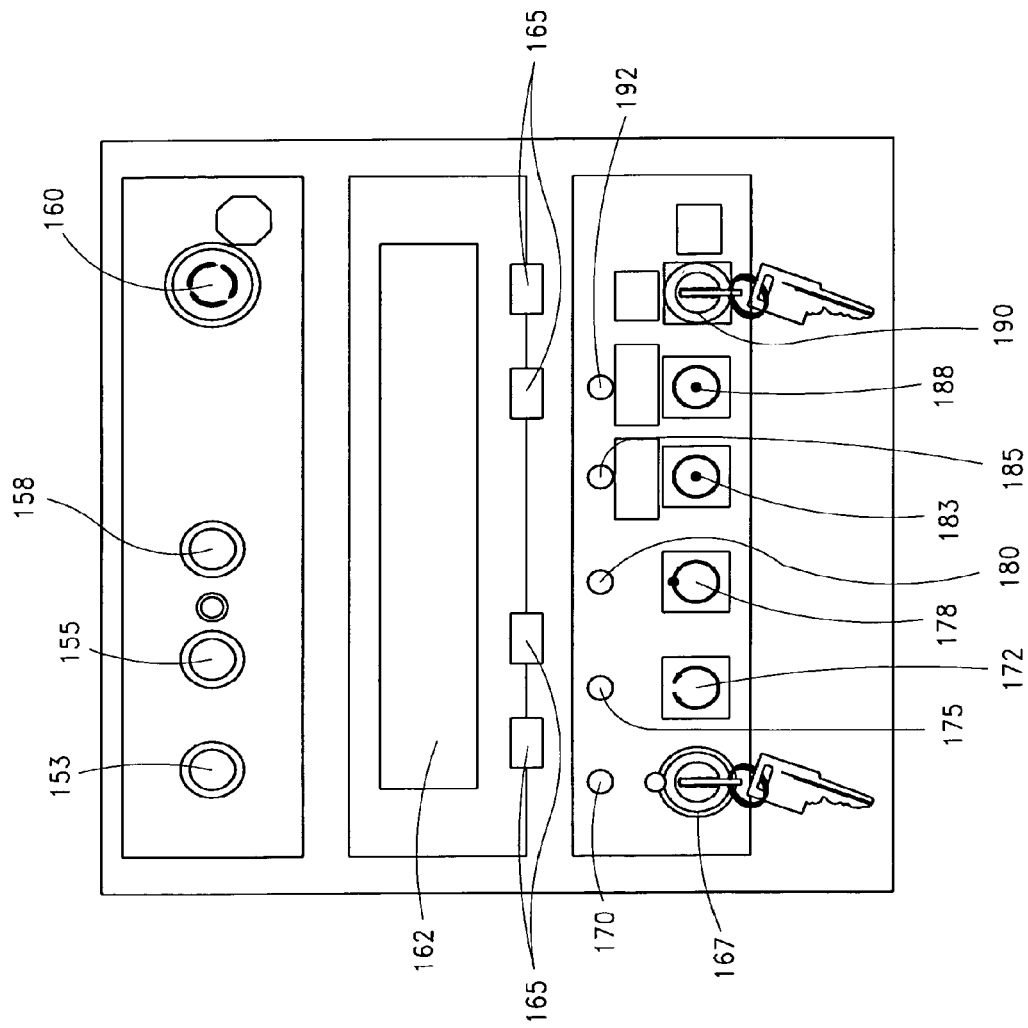
FIG. 11 depicts a control panel used to control the apparatus of FIG. 1.

FIG. 11 is a frontal view showing details of the control panel 30 on the front 21 of the UV light source 12 (see FIG. 3) and through which the operator interacts with the apparatus 10. The control panel 30 includes a power indicator 153 in the form of a green lamp that is lit whenever power is supplied to the generator unit 12. Adjacent the power indicator 153 is another green lamp that serves as a ready indicator 155, and which is lit when the unit is ready to deliver laser energy through the wand 32. A lasing indicator 158 in the form of an amber light illuminates while laser energy is being generated and delivered through the wand 32. A large, red pushbutton serves as an emergency stop button 160, which, when pressed, cuts power to the laser generator 12 thereby halting energy delivery through the wand 32.

A display window 162 is provided with an LED or LCD display or similar means for communicating information to the operator of the system 10. Four entry keys 165 are provided below the display window 162. By operating these keys the operator can input data into the system 10, e.g., through the use of menus and choices displayed to the operator through the display window 162.

A master key switch 167 is located at the lower left corner of the control panel 30. When the master key switch is off, no power is supplied to the system 10 and energy generation is disabled. Provision of a key to control this switch 167 is a security measure to limit use of the system 10 to authorized personnel. A master key switch indicator 170 is provided in the form of a green LED just above the master key switch 167. The master key switch indicator 170 lights whenever the master key switch 167 is in the "ON" position.

A reset button 172 is operable to switch the system 10 into a "power-on/self-test/warm-up" ("POST") mode. The POST mode is entered automatically when the system 10 is first switched on, after a power interruption, or when the rest button 172 is pressed. In POST mode, the system 10 performs diagnostic tests to assure that its components are operating properly and warms up the laser, a process that takes approximately three minutes. A POST mode indicator in the form of a yellow LED above the rest button 172 lights when the system 10 is in POST mode.

A standby button 178 is located to the right of the rest button 172 on the control panel 30. The system 10 enters a standby mode after the POST mode is completed and the unit warmed up, when the operator presses the standby button 178, or if two minutes elapses without energy delivery while the system is in any "treatment" mode, details of which are described below. The standby mode is a condition in which the system 10 is warmed up, operable, and ready to be switched into one of the treatment modes. Standby mode is indicated by a standby mode indicator 180 in the form of a green LED above the standby button 178.

A MED ready mode button 183 is operable to switch the system 10 in the first of three treatment modes, the MED mode. The MED mode is a diagnostic mode in which the system 10 is operated to determine a patient's minimal erythema dose (MED). The MED mode is indicated by an MED mode indicator 185 in the form of a green LED located directly over the MED ready mode button 183. Operation of the system 10 in MED mode is described in more detail below.

A treatment ready mode button 188 is located to the right of the MED ready mode button 183. When the treatment ready mode button 188 is depressed, the system is usable in either of two therapeutic treatment modes: tile mode or paint mode. Selection of tile mode or paint mode is made by the operator with a treatment mode key switch 190 disposed just to the right of the MED ready mode button 183. When the unit is in treatment ready mode, and hence in either tile mode or paint mode, a green LED 192 above the treatment ready mode button 188, which serves as a treatment ready mode indicator, lights to indicate this condition Like the master key switch 167, the treatment mode key switch 190 requires a key for operation to guard against unauthorized or unintentional changes between the two therapeutic treatment modes. Operation of the system in tile and paint mode is described in more detail below.

The system 10 described above can be used advantageously to teat psoriasis in a medical patient by first using the system to determine that patient's minimal erythema does (MED) and then by delivering therapeutic treatment to the patient based on that MED. Use and operation of the system 10 in such a way is described below for purposes of illustration.

The system 10 is first positioned and plugged into a suitable source of electrical power. The master key switch 167 (see FIG. 11) is switched on, the unit enters the POST mode, and the system 10 begins its self-test routine as the unit warms up. When the self-tests are completed and the unit is fully warmed up, the system 10 enters standby mode, in which it is ready for calibration, if needed.

If calibration is needed, the operator inserts the delivery end 50 (FIG. 6) of the wand 32 without any shield 52 (see FIG. 7) into the calibration port 42 (FIG. 6) on the front side of the UV light source 12. The operator then depresses the pushbutton 60 on the wand 32 to open the path for laser energy to emerge from the wand. The operator then depresses the foot pedal 31 and the unit begins lasing. Laser pulses are delivered into the calibration port where the intensity of the pulses is measured to determine their power output. The laser's power is calibrated and adjusted automatically by the system 10 to ensure that the wand 32 delivers about fifteen millijoules of ultraviolet energy into the calibration port with each laser pulse. When calibration is complete, this will be indicated in the display window 162 on the control panel 30 (see FIG. 11), and the system 10 will return to standby mode.

Figure 12:
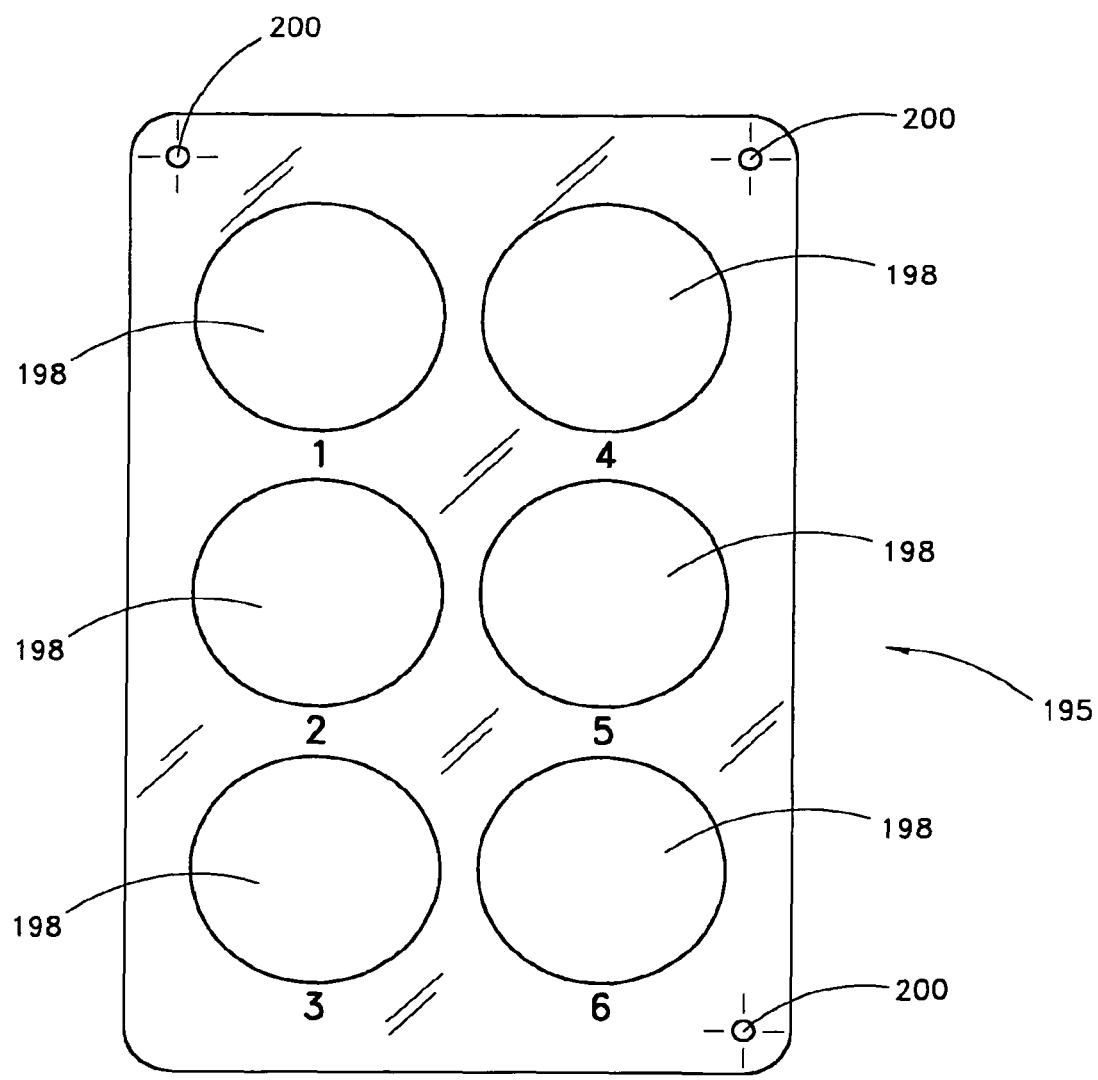
FIG. 12 shows a minimum erythema dose (MED) template usable with the apparatus of FIG. 1.

The system is used in MED mode to determine the patient's individual MED. FIG. 12 depicts a MED template 195, which is a thin, flexible plastic sheet with six individually numbered MED template apertures 198 sized to receive the shield 53 at the delivery end 50 of the wand 32. The MED template 195 further includes marking holes 200 with cross-hairs for positioning the template on the patient's skin in a suitable location. The MED template 195 will be used to determine the patient's MED and can be taped in place on the patient's skin in an untagged region that is not normally exposed to sunlight, e.g., the back, stomach, or buttocks. The location preferably is one that is not affected by the patient's skin disorder. To facilitate later repositioning of the MED template 195 in the same location, the patient's skin can be marked with a marker through the marking holes 200.

With the MED template 195 taped in an appropriate location on the patient's skin, the operator presses the MED ready mode button 183 to put the system 10 into MED mode. The operator aligns the shield 53 on the end of the wand 32 with the first MED template aperture 198 of the MED template 195. The soft pads 150 on the nubs 55 at the end of the shield 53 can rest lightly against the patient's skin to ensure that the wand 32 is the proper distance from the patient's skin. With the wand 32 properly positioned, the operator depresses the pushbutton 60 on the wand, and then operators the foot pedal 31 to initiate lasing. The system 10 operates automatically to deliver energy to the patient's skin in an amount equal to 100 millijoules per square centimeter.

The operator then moves the wand 32 to the second MED template aperture 198 and, again with the pushbutton 60 held down, operates the foot pedal 31. The system 10 adjusts itself automatically in MED mode to deliver a number of pulses sufficient to deliver 150 millijoules per square centimeter to the skin under the second cutout. The operator repeats the process with the system automatically adjusting to deliver standard MED determination doses as follows:

| MED TEMPLATE APERTURE NUMBER | MED DETERMINATION DOSE ENERGY (mJ/cm$^2$) |
| --- | --- |
| 1 | 100 |
| 2 | 150 |
| 3 | 200 |
| 4 | 250 |
| 5 | 300 |
| 6 | 350 |

Note that the system 10 increments the MED determination doses automatically without further input from the operator. Each MED determination is incremented and delivered in turn. The user need only ensure that the wand 32 is aligned properly with the appropriate MED template aperture 198. After the MED determination doses are delivered, the template 195 is removed, and the patient is then asked to return the next day for observation and determination of that patient's MED.

When the patient returns, preferably, about 24 hours after delivery of the MED determination doses, an identical MED template 195 is again placed over the patient's skin with the help of the marks made previously. A patient's MED is defined as the minimal dosage at which a noticeable change in color occurs with distinct edges. The practitioner notes and specifies the patient's MED in terms of the number (1-6) of the MED template aperture 198 that corresponds to the lowest MED determination dose for which this distinct color change occurs.

After the patient's MED has been determined the patient's physician selects a "treatment multiplier." The system 10 is programmed to accept treatment multipliers in the form of integer numbers between e.g., two and eight or two and sixteen or twenty. The inventors have found that a treatment multiplier of two provides mild but nevertheless effective therapy, while a treatment multiple of eight provides more aggressive and generally more effective therapy while still remaining within acceptable safety limits. Intermediate treatment multipliers produce intermediate effects.

After the patient's MED has been determined and a treatment multiplier chosen, the user may begin delivering therapeutic treatment. The user can also adjust treatment mode key switch 190 to select between tile mode and paint mode. When the user place the system 10 in treatment ready mode by depressing the treatment ready mode button 188, the system 10 will prompt the user to enter the patient's MED and the preselected treatment multiplier.

In tile mode, the system 10 will operate automatically to deliver a number of energy pulses equal to one therapeutic dose each time the foot pedal 31 is pressed by the user. The therapeutic dose is equal to the patient's MED, as determined previously, multiplied by the preselected treatment multiplier. Thus, for example, if the first color change with distinct edges was noted corresponding to the third MED template aperture number, the patient's MED will have been found to be 200 millijoules per square centimeter. If a treatment multiplier of six is selected, the system 10 will operator to deliver a number of pulses corresponding to 1200 millijoules per square centimeter each time the foot pedal 31 is pressed.

The user will then move the wand 32 stepwise over the patient's psoriasis, stopping at multiple locations to press the soft pads 150 of the shield 53 lightly against the patient's skin. At each location, the user will operate the foot peal 31 and pushbutton 60 to deliver one therapeutic dose before moving on to the next location. The user will repeat this process until substantially the entire area of the patient's psoriasis has been treated.

Figure 13:
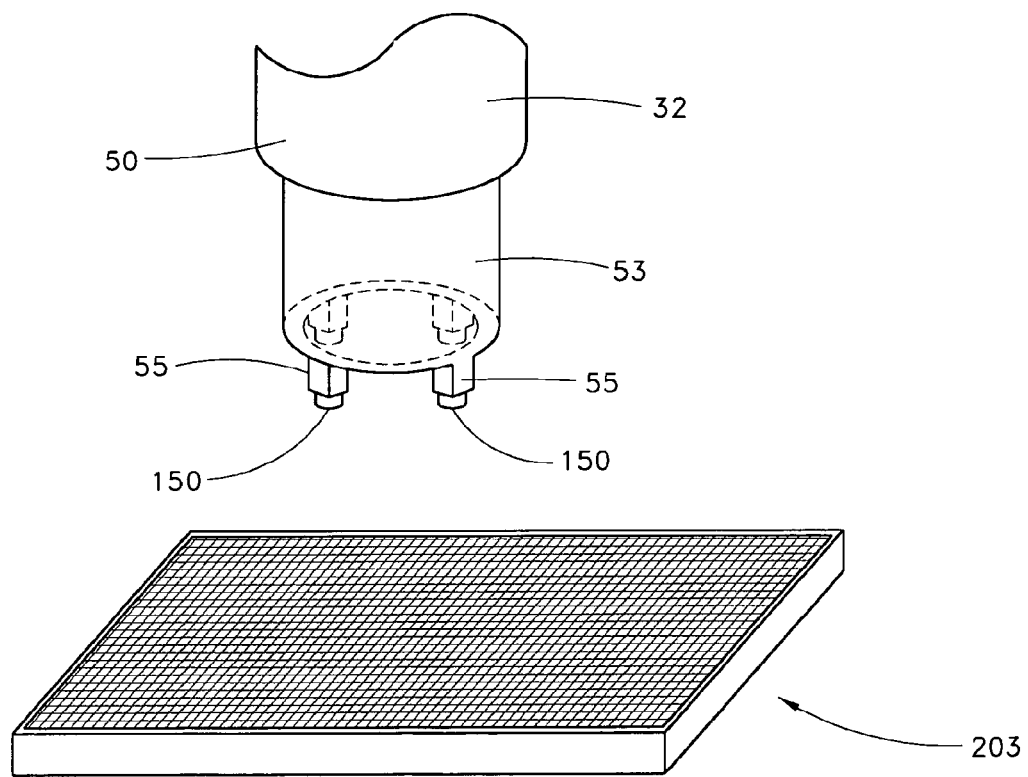
FIG. 13 depicts ink being applied to the delivery device of FIG. 2 by an ink pad.

An ink pad 203 bearing a quantity of an appropriate non-toxic ink may be provided to assist the user in covering the entire treatment surface uniformly in tile mode. As depicted in FIG. 13, the shield 53 at the end of the wand 32 may be pressed lightly onto the ink pad so that the soft pads 150 at the ends of the shield numbs 55 pick up a small quantity of the ink.

Figure 14:
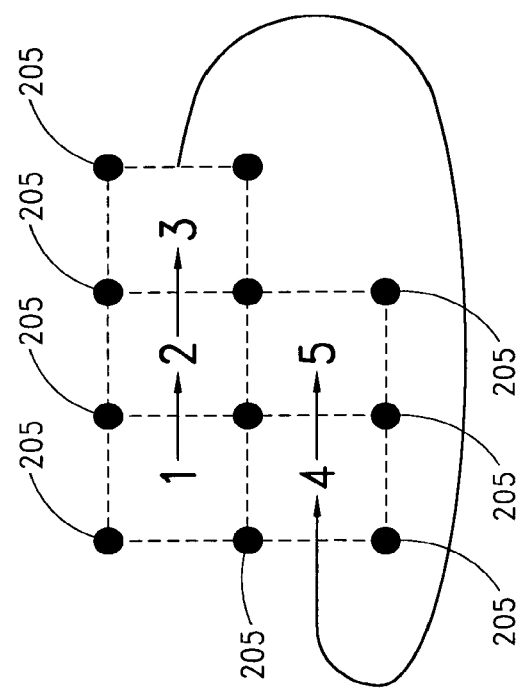
FIG. 14 illustrates how the delivery may be used to deliver therapy in a "tile mode"

As suggested by FIG. 14, when the soft pads 150 are pressed against the patient's skin, the ink on the soft pads (see, e.g., FIG. 10) will mark the patient's skin at the location of the nubs 55. As described above, the optics of the system 10 are such that the nubs 55 correspond to the corners of the treated area. The user may the move the wand 32 step-wise, aligning the soft pads 150 at a treatment location with corner marks of a previous location and delivering therapy at each location until substantially the entire area of the patient's affected skin is treated. FIG. 14 shows corner marks 205 formed by ink from the soft pads arrayed in a "tile" pattern across the patient's skin over an area of diseased tissue. When treatment is completed, the user can switch the system 10 to standby mode by pressing the standby button 178 on control panel 30.

Paint mode differs from tile mode in that therapy is delivered as the wand 32 is swept more or less continuously over the treated surface rather than at multiple discrete locations as is the case in tile mode. Paint mode is similar to tile mode in that before initiating treatment, the user will first enter the patient's MED and the preselected treatment multiplier as described above.

Figure 15:
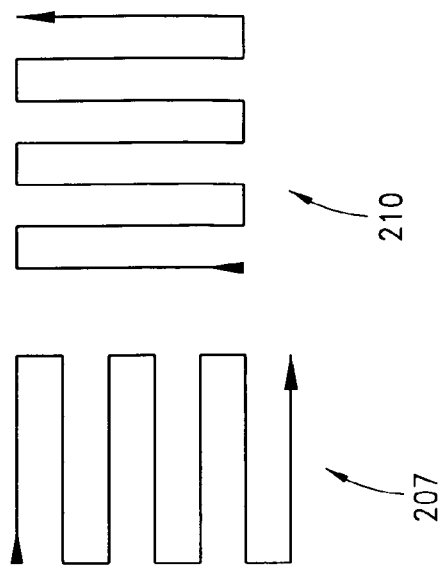
FIG. 15 shows how the delivery device may be used to deliver therapy in a "paint mode."

In paint mode, the user moves the wand 32 over the entire treated area in patterns suggested by FIG. 15. To ensure complete coverage, the user first moves the wand 32 in the horizontal pattern 207, the user then repeats the motion using the vertical pattern 210. In each pattern, the user may move the wand 32, for example, at a rate of two square centimeters per second. The unit will automatically generate laser pulses at a rate appropriate to deliver the desired therapeutic dose over the course of the two treatment passes.

Test Results

Efficacy of a system 10 and method similar to the one described above in treating psoriasis was evaluated in an investigative clinical trial. Thirteen patients were enrolled in the clinical trail. Each of the trial subjects had psoriasis manifesting itself in the form of multiple stable plaques. Stable plaques were defined as plaques that had been present and essentially unchanged for at least eight weeks prior to the patient's enrollment in the study. Patient's enrolling in the study were required to cease all topical therapy for at least two weeks prior to treatment in the study, systemic therapy for at least eight weeks, and phototherapy and photochemotherapy for at least four weeks.

The clinical study was conducted with apparatus 10 substantially the same as that described above. Each patient's individual minimal erythema dose (MED) was determined by exposing the patient's skin to a set of controlled response calibration doses. The response calibration doses were applied to unexposed gluetal skin not affected by psoriasis. The UV light source 20 comprising a laser and the delivery device 15 used in the study generated a beam of ultraviolet light having a circular cross-section with an area of 4.91 cm$^2$ (2.5 cm in diameter). Each patient received eight different calibrations doses—100, 140, 280, 400, 560, 800, 1120, and 1600 millijoules delivered over the 4.91 cm$^2$ area of the beam.

The patient's response to the response calibration doses was observed 24 hours after the calibration doses were delivered. Each patient's individual MED was defined as the minimum calibration dose at which a color change with well defined edges was observed. Individual MEDs were determined by observing each patient's unique response to the response calibration dose.

After an MED was determined for each patient, a tightly controlled and closely observed regimen of therapeutic treatments was conducted on the subjects. Four similarly appearing plaques of adequate size were selected for each patient. Originally, it was intended that ultraviolet light would be delivered to six different locations on each of the four plaques in doses equal to 0.5, 1, 2, 4, 8, and 16 times the patient's individually determined MED. Thus, it was intended that each patient would receive therapy at 24 different locations, six locations in each of four plaques.

All of the plaques were intended to receive identical therapeutic doses. Each plaque, however, was intended to receive therapy according to a different treatment schedule. The first plaque would receive a single treatment, the second plaque two treatments, and the third plaque four. The fourth plaque was to receive 20 treatments. Treatments to the fourth plaque were administered twice weekly with a 72-hour interval between each administration. The 20 twice-weekly treatments were thus given over a 10-week period.

The patient's skin was marked at the time of therapy with indelible ink at each treatment site for subsequent identification. The patients were observed and evaluated at 2-week intervals during the 10-week treatment period, and at two, four, and six months after the treatment ended.

When the study began, response calibration doses in the amounts noted above were administered first to each of the thirteen patients. The patients' responses to the calibration doses were observed, and individual MEDs were determined for each patient. Ultraviolet light delivery then began for purposes of therapy.

When the first three subjects were treated, it was observed that dosages of 8 and 16 times the patient's MED caused blistering at the treatment site within twenty-four hours of administration. It was therefore decided that the treatment regimen should be modified to include delivery doses of 0.5, 1, 2, 3, 4, and 6 times the patients' MEDs. These doses were well-tolerated by all the subjects, with some slight erythema observed in some subjects at 4 and 6 MEDs. This erythema was occasionally accompanied by a moderate burning sensation, in which case treatment at these doses was temporarily omitted.

Repeated doses at 0.5 and 1 MED did not significantly alleviate the psoriasis. However, repeated exposures at between 2 and 6 MEDs did result in significant improvement by approximately 8 weeks following 2 treatments, 6 weeks following 4 treatments, and 3-4 weeks with 20 treatments. It was noted that after the blistering had healed in the three patients who received doses of 8 and 16 MEDs, the patient's psoriasis had cleared at those sites as well.

This method for treating skin disorders including but not limited to psoriasis and vitiligo can be improved by cooling the skin to be treated prior to and/or during application of high doses of narrow band UV light to the affected area of the skin. Cooling can be accomplished, e.g., by spraying the skin with a cool liquid, gas, or air or by applying a cool object to the affected area of skin. Cooling may reduce the degree of injury to the patient that would ordinarily result from exposure to such elevated levels of UV light and thus permits higher doses of UV light to be administered. For example, when a pulsed source such as a pulsed laser is employed, cooling counters the build up of thermal energy with a series of pulse so that high temperatures associated with injury to the epidermis are not reached. Cooling may also remove heat, slowing the accumulation and the rise in temperature with application of the plurality of pulses. Heat can then be dissipated under normal thermal dissipation processes that occur over times exceeding the thermal dissipation time constant $\tau_{thermal}$. Cooling may also establish a low temperature as the starting point from which the skin begins to heat up as thermal energy accumulates with each additional pulse. By preventing tissue damage and thereby enabling higher fluences of UV light, the total number of treatments can be reduced and remission can be improved. Cooling can also permit more frequent treatments if necessary. The affect of cooling on the skins response to UV light is more fully described in "Influence of Temperature on Ultraviolet Injury" R. Freeman, J. Knox, Arch. of Derm., Vol. 89, June 1964, which is hereby incorporated herein by reference in its entirety.

To reduce UV damage, the surface of the tissue to be treated is preferably cooled to about 5° C. or below, and more preferably to about 0° C. just prior to and/or during application of the UV radiation. The greater the degree of cooling, the higher the tolerance to the dose without injury; thus temperatures of about −5° C. or less may improve results of UV treatment. The low temperature limit is set by the amount of cooling that will damage healthy skin in the proximity of the disease tissue. Preferably, the diseased skin is cooled to a temperature substantially lower than the normal temperature of skin, the normal temperature of skin being about 34° C.

Figure 16:
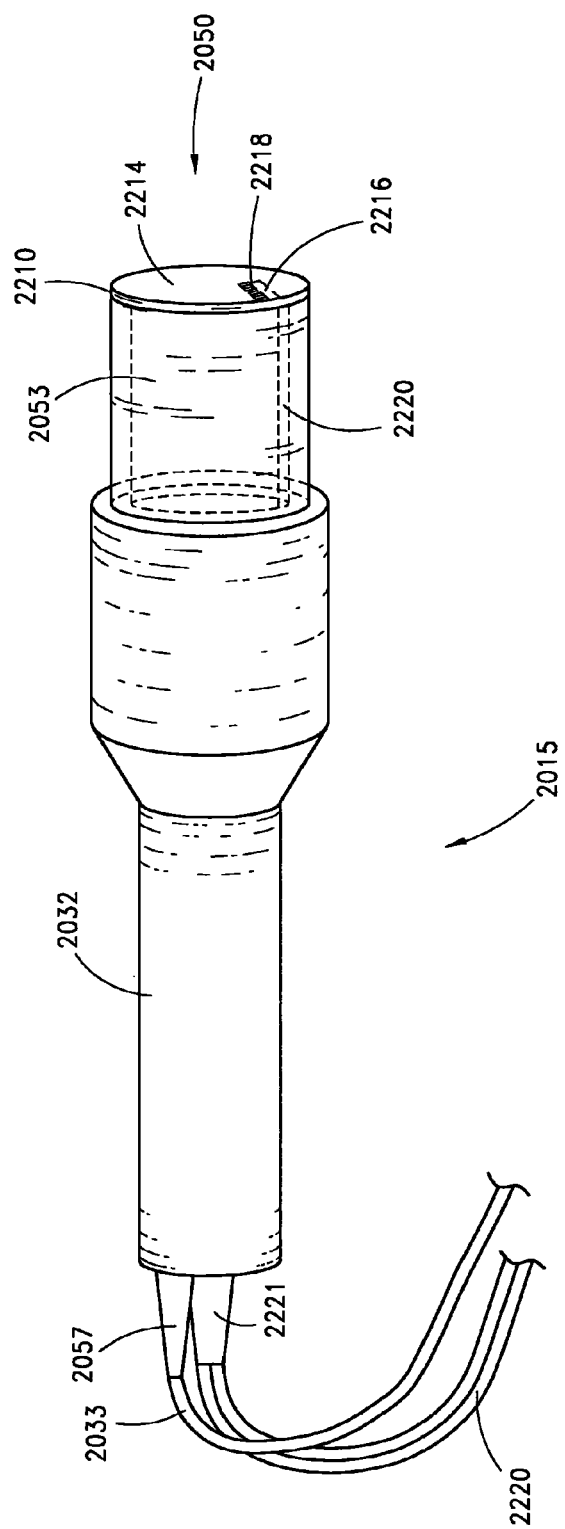
FIG. 16 shows a delivery device that additionally includes a plate and a thermoelectric cooler attached to the plate to provide cooling thereto.
Figure 18:
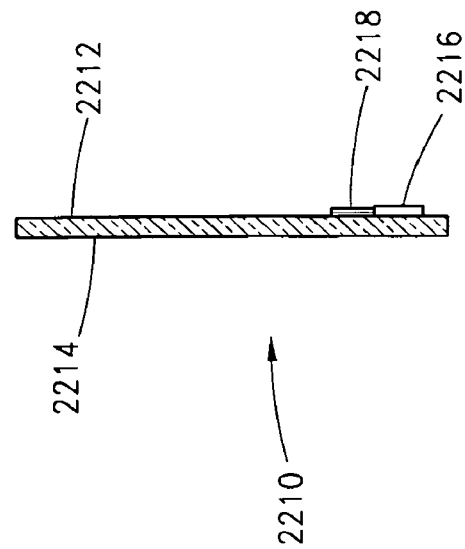
FIGS. 17 and 18 are front and cross-sectional views of the chilled plate of FIG. 16.
Figure 17:
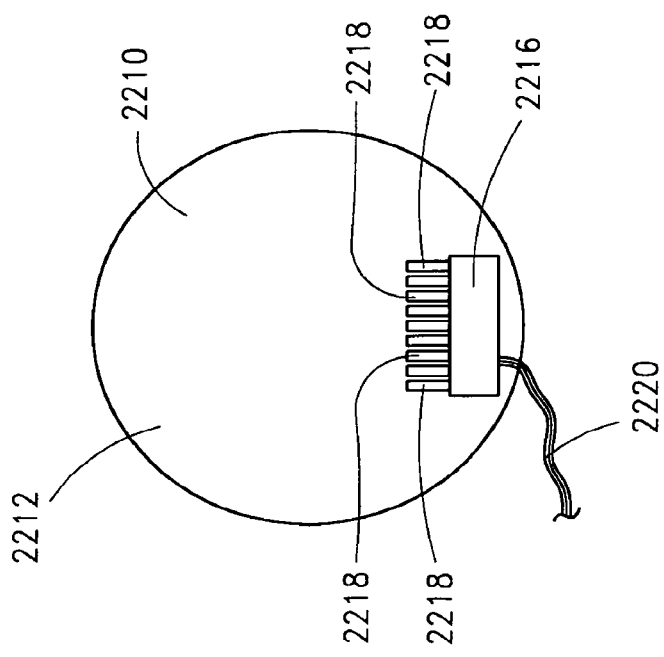

Cooling can be accomplished by applying a chilled UV transparent substrate 2210 such as shown in FIGS. 16-18 to the area of skin to be treated. This cooled substrate or plate 2210 may comprise, e.g., sapphire, quartz, fused silica, borosilicate glass, or any glass or other material that is transparent to UV light in the preferred wavelength range for treatment and that can withstand the cooling. To simplify the treatment procedure for the heathcare provider, this cooled substrate 2210 may be incorporated in and connected to a device 2015 used to deliver UV radiation from a UV source to a localized region of skin that includes the diseased tissue. This substrate 2210, for example, may be attached to a wand 2032 similar to the one depicted in FIGS. 6-10 and having a rectangular output aperture 138 shown in FIGS. 8 and 10 at the end 2050 where UV light is emitted for delivery to the patient. As most clearly shown in FIGS. 17 and 18, the plate 2210 is circular and has oppositely facing circularly shaped surfaces 2212, 2214, one proximal and one distal to the output aperture 138 of the wand 2032. The plate 2210, and more particularly, the opposing circularly shaped surfaces 2212, 2214, have a spatial extent greater in size than the rectangular output aperture 138 of the wand 2032 so that light forming a beam and exiting the output aperture will be fully contained within the circular surfaces of the plate as it passes through them. The plate 2210 is mounted on the shield 2053 such that the distal surface 2214 forms an exterior surface of the delivery device 2015 for unrestricted access to the epidermis of the patient; that is, no other surface on the wand 2032 or device prevents the distal surface from fully contacting the patient's skin.

A thermoelectric cooler 2216 having a plurality of cooling leads 2218 is mounted on the plate 2210 such that the cooling leads are firmly connected to and form good thermal contact with the proximal surface 2212 of the plate. Adhering the thermoelectric cooler 2216 to the plate 2210, and more particularly to one of the circular surfaces 2212, 2214 of the plate, is convenient as both circular surfaces on the plate provide large areas for accommodating the cooler and its cooling leads 2218. Mounting the cooler 2216 on the distal surface 2214 of the plate 2210 is less desirable as the distal surface is preferably freed of any obstructions that would limit good thermal contact between the cooling plate 2210 the patient's skin. Such irregular features on the distal surface 2214 of the plate 2210 would, in addition, likely inhibit smoothly scanning this chilled plate across a patient's skin. However, to the extent that such limitations could be avoided, the cooler can be located on the distal surface 2214 or on other surfaces of the cooling plate and/or of the wand 2032 e.g., on the shield 2053. However, by selecting a location for the cooler 2216 such that a substantial portion of the cooling leads 2218 touch the cooling plate 2210, the cooling plate can be efficiently cooled.

Electrical wires 2220 run through the wand 2032 and to the thermoelectric cooler 2216 to provide electrical power for cooling the leads 2218. These electrical wires 2220 connect to the wand 2032 through an elastomeric connection boot 2021, which offers strain relief and guards against kinking and which is mounted on the wand 2032 adjacent one other elastomeric connection boot 2057 that receives an optical cable 2033 for delivery of UV light. A return optical cable is not included in this embodiment. The thermoelectric cooler 2216, including the cooling leads 2218, and the electrical wires 2220 to the wand 2032 can be affixed to the wand 2032 in a conventional manner such as for example with the aid of an adhesive.

Figure 3:
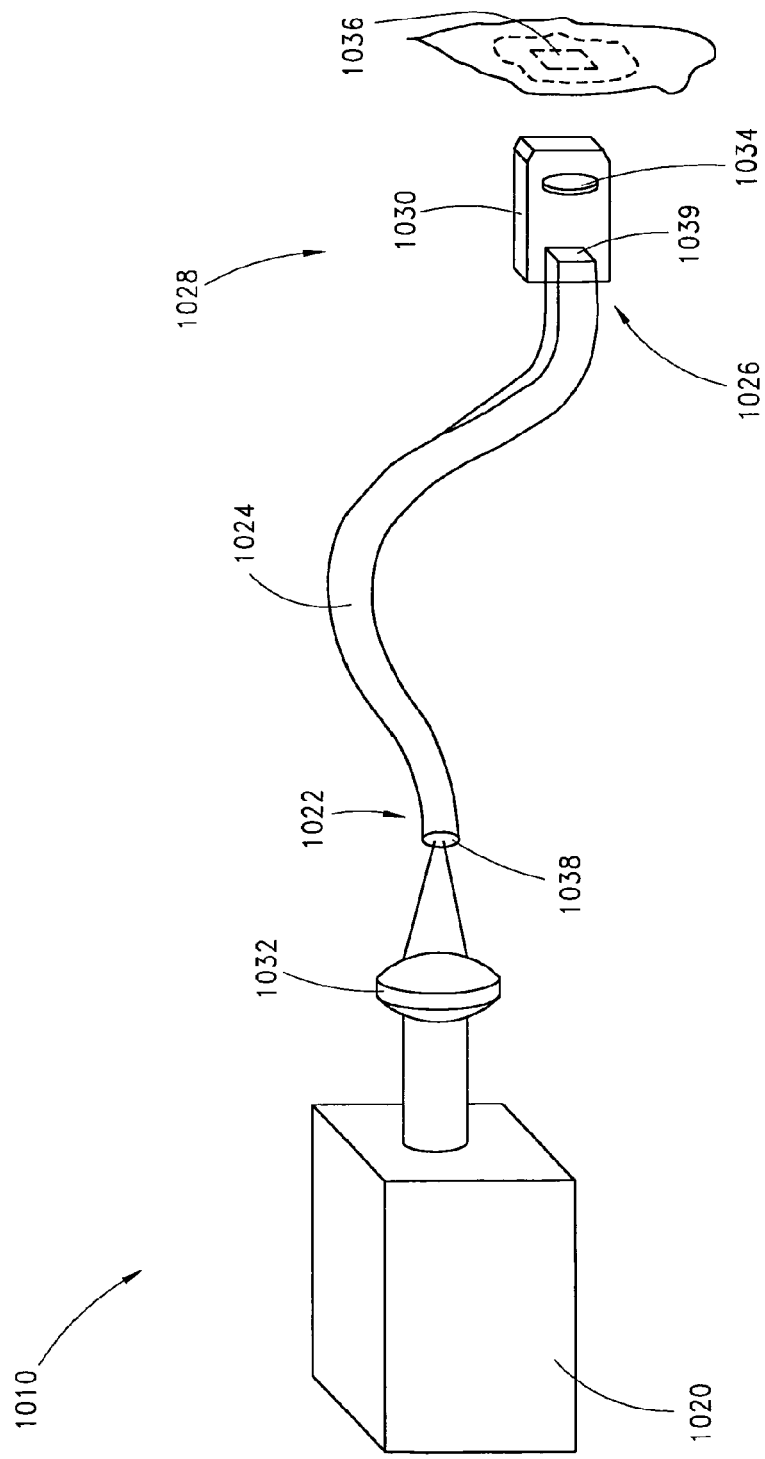
FIG. 3 depicts a schematic view of one embodiment of the present invention comprising a laser source, a coupling lens, and an optical fiber for exposing diseased skin to doses of UV-B wavelength (between about 290 to 320 nanometers) light sufficient to effectively treat skin disorders like psoriasis.

The chilled substrate 2210 is to be employed with the apparatus 1010 described above which offers significant advantages in treating skin disorders and which comprises a source 1012 of UV radiation and a delivery system 1014. The chilled substrate 2210, for example, may be used in connection with a laser-based system 1010 such as depicted in FIG. 3 that contains a laser 1020, possible computer controlled, that is optically coupled to a hand piece 1030 via a flexible guide 1024. The laser 1020 may comprise an excimer laser outputting light having a wavelength of about 308 nanometers while the hand piece 1030 might resemble the wand 2032 shown in FIG. 16. In one specific embodiment, the laser 1020 can be energized for up to 300 pulses in about a second and the wand 2032 distributes about 10 millijoules per pulse (mJ/pulse) output from the 308 nanometer excimer laser over an area of approximately 3 cm$^2$ at a target region of the epidermis. The UV beam applied to the diseased skin is not, however, limited to these specific fluency and size specifications but rather may range widely as describe above. In particular, an area of skin greater than 3 cm$^2$ of skin may be cooled to about 0° C. when placed on the skin.

To treat a patient afflicted with a skin disorder responsive to UV light, the healthcare provider may position the wand 1032 over a diseased region of skin such that a substantial portion of the distal surface 2214 of the cooled plate 2210 is in physical contact with the diseased region. With the thermoelectric cooler 2216 activated, the area of skin touching the plate is cooled, preferably to a temperature below about 5° C., and more preferably to about 0° C. or less. Light emitted from the laser 1020 is coupled via the input cable 2033 into the wand 2032 and exits from the wand after passing through the rectangular aperture 138. This light propagates forward within a beam that is transmitted through the chilled plate 2220 and projected onto the skin pressed against the distal end 2214 of the plate. A therapeutic dose of UV light is thereby directed onto the skin in accordance with the discussions above with regard to FIGS. 1-15, but while the skin is cooled to a temperature lower than the normal temperature of skin. Substantially all of this dose of ultraviolet light is applied to the skin before the chilled plate warms up, that is, within a period of time shorter than the thermal time constant associated with the plate 2210. In addition, the dose is preferably, although not necessarily, applied to only a fraction of the area of skin that is cooled. Likewise, the beam of light that exits the wand 2032 will likely illuminate only a portion of the chilled plate 2210. For example, in the case of treating psoriasis, the beam may encompass both the psoriatic plaque and surrounding paralesional tissue as well as some adjacent healthy tissue, with both the plaque, the paralesional tissue, and preferably an additional peripheral region of healthy skin all being cooled.

Other arrangements for cooling the plate or substrate 2210 are included within the scope of the invention. In lieu of mounting a thermoelectric cooler 2216 on the surface 2212 of the plate, the plate 2210 may be cooled with fluid by providing a pathway for flowing a liquid or gas chilled to a desirably cool temperature across or through the plate. For example, hollow metal lines can be place in thermal contact with the substrate 2210 and chilled water can be circulated through these lines to sufficiently lower the temperature of the plate. In addition, the plate 2210 need not be attached to the delivery device 2015 but may be separate and independent from the delivery device. For example, the UV transparent plate or substrate 2210 may be cooled in a refrigerator, or by immersing it in or contacting to or otherwise exposing it to a chilled liquid, solid, or gas prior to or while being placed on the patient's skin. The light can then be passed through the chilled plate 2210 in a manner described above. Similarly, an object formed into a shape other than a plate but having a temperature less than the temperature of the diseased skin, and preferably below about 5° C. or 0° C. can be employed to cool the skin and provide therapeutic results. The cool object need only be transparent to UV light of the wavelength employed for treatment and preferably comprise a material suitable for maintaining a cool temperature for a sufficiently long period and that is thermally conductive so as to readily absorb heat from the skin.

Figure 19:
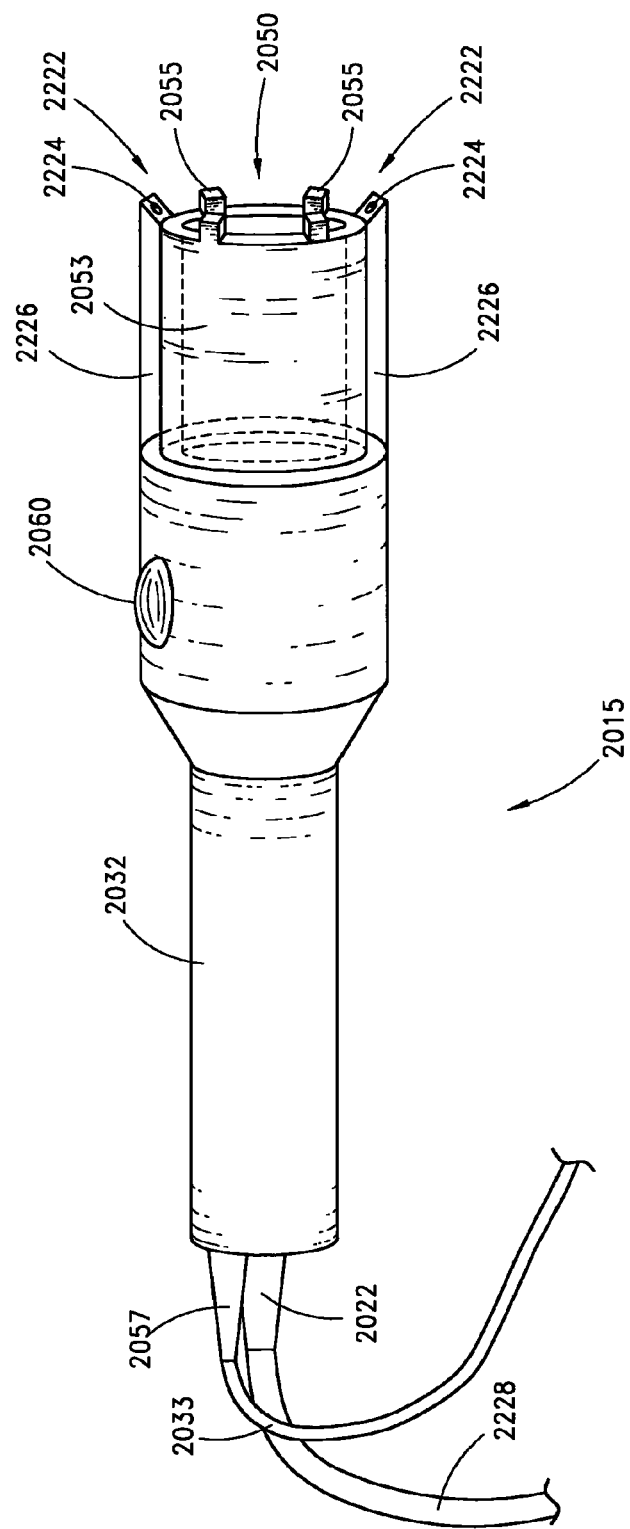
FIG. 19 depicts a delivery device that includes a jet that provides cooling.

Alternatively, cooling can be accomplished by exposing the skin directly to chilled liquid or gas or cooled air, possibly in the form of a spray or stream ejected from jets 2222 incorporated in the wand 2032 depicted in FIG. 19. These jets 2222 are formed by providing openings 2224 in channels 2226 for flowing liquid or gas coolant or cool air through the wand. In the wand 2032 depicted in FIG. 19, portions of the channels 2224 for transporting the coolant are visible adjacent to and in contact with the UV shield 2053. Other portions of the channels are in interior regions of the wand 2032 and are thus not visible from the perspective shown in FIG. 19. A supply tube 2228 feeds the channels 2226 located within the wand 2032. This supply tube 2228 is connected to the wand 2032 through the elastomeric connection boot 2022 mounted on the wand 2032 adjacent another elastomeric connection boot 2057 that receives the optical cable 2033 for delivery of UV light. As discussed above, these elastomeric connection boots 2022, 2057 offer strain relief and guard against kinking.

The supply tube 2228 is connected at one end to a source of coolant (not shown) comprising, e.g., a supply of chilled coolant or cyrogens, and at another end to the channels 2224 traversing through the wand 2032. These channels 2224, which may be insulated, provide a pathway for the liquid or gaseous coolant from the supply tube 2228 to the openings 2224 in the portion of the channels located at the delivery end 2050 of the wand 2032. These openings 2224 are oriented to direct the spray toward a region where light output from the wand 2032 is also incident. The jets 2222, however, are preferably designed to spread the coolant over an area of the patient's skin that is larger than that portion illuminated by the beam of UV light. The coolant employed may comprise chilled water, chemical solutions sufficiently cooled, liquid or gas cryogens such as freon, liquid $CO_2$ or liquid $N_2$, or combinations thereof. Other possible coolants that are suitable for spraying on the patient's skin prior and/or during exposure to UV light include but are not limited to cool air.

Figure 4:
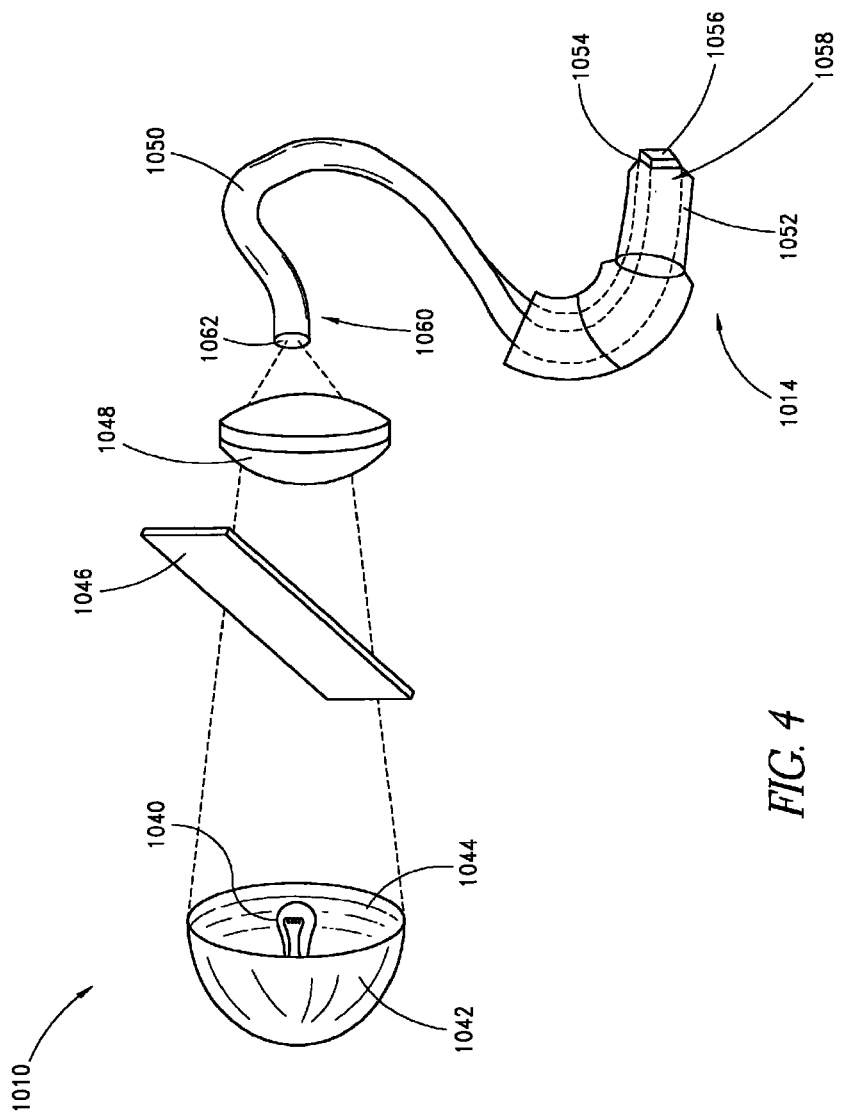
FIG. 4 is a schematic view of one embodiment of the present invention comprising an arc lamp, a reflector, a wavelength selection filter, and an optical fiber for treating skin disorders.

Like the chilled substrate 2210, the jet spray is to be employed with the apparatus 1010 for treating skin disorders described above comprising a source of UV radiation 1012 and a delivery system 1014. The jet spray, for example, may be used in connection with an arc lamp-based system 1010 such as depicted in FIG. 4 and that contains an arc lamp 1040 optically coupled to a hand piece 1052 via a flexible guide 1050. The system 1010 additionally includes a filter 1046 for limiting the wavelengths of light to a narrow band of UV preferably somewhere between about 300 and 315 nanometers and a reflector 1042 for collecting light emitted from the lamp. In one specific embodiment, the lamp-based system 1010 produces at least 1 watt (W) of UV radiation that is directed onto the patient's skin. The lamp 1040 is optically coupled by a lens 1048 to the UV light guide 1050, which is connected to the handpiece 1052 or wand 2032. A mechanical shutter 97 in the wand 2032 controls the flow the light output therefrom. This mechanical shutter 97 is connected to a multifunction trigger 2060 which is conveniently located on the wand 2032 depicted in FIG. 19 and which, when depressed, opens the shutter. One or more valves (not shown) situated in the channels 2226 may also be electrically or mechanically connected to the multifunction trigger 2060 such that the trigger, when depressed, also opens the valve.

To treat a patient afflicted with a skin disorder responsive to UV light, the healthcare provider positions the delivery end 2050 of the wand 1032 over a diseased area of skin such that the openings 2224 of the jets 2222 are in position to direct coolant onto a portion of skin including but not necessarily limited to the diseased area. The operator then depresses the trigger 2060 to allow the UV radiation from the lamp 1040 to pass through the wand 2032 and onto the patient's skin. The jets 2222 are also activated by the trigger 2060 on the wand 2032. The coolant flows from reservoir through the supply tube 2228 into the channels 2226 in the wand 2032 and out the opening 2224 of the jets 2222. Preferably, the coolant is pumped through the jets 2222 or the reservoir is a pressurized source of coolant such that the coolant is sprayed out of the opening of the jets and spreads onto the skin. The coolant spray cools on contact with the skin. Preferably, the spray cools the skin to a temperature below about 5° C., and more preferably to about 0° C. or less prior to and/or during exposure of the skin to UV light delivered by the wand 2032. In the case where the coolant comprises chilled liquid or gas, the low temperature of the coolant cools the skin, however, the coolant may provide additional cooling if the coolant evaporates upon or soon after contacting the skin.

In addition, the wand 2032 directs a therapeutic dose of UV light onto the skin in accordance with the discussions above with regard to FIGS. 1-15, however this dose is delivered while the skin is cooled to a temperature lower than the normal temperature of skin, i.e. about 34° C. As described above, the skin is preferably cooled prior to and/or during UV exposure and substantially all of the dose of UV light is applied to the skin before the skin warms up. Also, the jet spray preferably cools the skin faster than the skin receives the total integrated sum of UV radiation directed to one location. The skin is therefore sufficiently cooled prior to application of injurious doses of radiation to the skin, and thus, tissue damage is avoided or reduced. In addition, as previously mentioned, the dose is preferably, although not necessarily, applied to only a fraction of the area of skin that is cooled.

The technique of providing cooling is not limited to any one particular way of cooling the skin prior to and/or during exposure to suitable dosages of UV light having the appropriate wavelength. Rather, other methods and apparatus for cooling the plate or substrate 2210 are included within the scope of the invention. For example, cool air can be ejected from the jets 2222 or supplied by a circulating fan or blower. In addition, in cases, where jets 2222 are employed, the Venturii affect may be exploited to create a chilled zone. Alternatively, a UV transparent gel may be applied to the skin; the gel may be cooled before or after it is applied to the epidermis to achieve appropriate cooling. This gel may also aid in coupling the UV energy from the source 1012 to the skin by providing index-matching. In addition, many skin disorders such as psoriasis are accompanied by scaling and flaking of the skin. The cooling gel or fluid may also serve to wet this dead skin to allow more UV light to penetrate instead of being scattered by the scaling, flaking areas of skin.

Selection of the appropriate method of cooling may be influenced by the intended use and the anticipated frequency of use. Systems designed to treat small areas of diseased tissue such as psoriasis plaque modest in size, may suitably employ a cryogen spray, which is consumable. In contrast, a liquid cooled window with a re-circulating chiller may be more appropriate for treating larger areas of skin afflicted by, e.g., vitiligo or psoriasis, as fast and effective cooling can be provided without requiring a large supply of a consumable coolant.

As described above, cooling the skin may increase the skin's tolerance to high doses of UV light. Higher doses of UV light can be applied to the skin without inducing tissue damage. With higher doses of UV light, the total number of treatments can be reduced, thereby lowering the cost of treating the skin disorder. Requiring less doctor visits also promotes patient compliance to an otherwise difficult regimen and improves the likelihood of success of the overall treatment.

Cooling also permits a higher frequency of individual treatment sessions. A typical treatment regimen may include three or more visits to the physician or healthcare provider to completely clear the disease. In an effort to avoid injury, a subsequent session is not scheduled too soon as time is necessary to permit healing. Consecutive sessions, for example, may be separated by at least about 90 hours when suitable doses of 308 nanometer light are employed to treat the disease. The time between sessions, however, can be shortened by cooling the skin prior to and/or during the application of UV light as discussed above, i.e., if the skin is cooled during exposure to ultraviolet light, a subsequent treatment session can follow sooner. For these and other reasons, the UV treatment preferably includes cooling.

Thus, is has been demonstrated that psoriasis can be treated effectively by local administration of ultraviolet light in high doses. Since the patient's tolerance of and response to ultraviolet therapy varies significantly according to their individual skin types, it is highly advantageous to administer the therapy based on observed individual MEDs determined for each patient.

The therapy may be delivered at approximately one times the patient's MED per treatment or greater. More preferably, the therapy is delivered in doses of between about 2 and 6 MEDs per treatment. Therapy may be delivered in a single treatment, but multiple treatments may be preferred. Treatment may be delivered once, twice or four times, etc. Treatment may also be delivered twice per week for ten weeks in succession. Cooling the skin prior to and/or while exposing the skin to the UV light can permit higher doses to be used thereby reducing the total number of individual treatment sessions. Cooling can also shorten the time between successive treatment sessions.

Exemplary systems 10 and methods for delivering phototherapy according to the invention have been described herein. Modifications and additions to these preferred apparatus and methods will no doubt occur to those skilled in the art. For example, although the method has been described as suitable for treatment of psoriasis, the method is not so limited, but rather may be effective in treating skin or tissue for various other purposes, for example to provide relief or a remedy for other diseases and disorders. Further applications, additions, and modifications may occur to those skilled in the art and the scope of the invention is not to be limited to the preferred embodiment described herein. Rather, the scope of the invention should be determined by reference to the claims, along with the full scope of equivalents to which those claims are legally entitled.

As indicated above, successful treatment of skin disorders like psoriasis is dose-dependent. More specifically, the preferred dosage for successful treatment is within a broad range; dosages below this range are less effective while doses above this range may cause harmful side effects. By contrast, certain treatments, such as ablation and skin resurfacing, merely require that the dosage exceed a minimum energy threshold to be successful. Higher dosages that exceed the minimum threshold do little harm to the patient. In treating skin disorders like psoriasis, the method and apparatus for treatment is preferably capable of delivering a dosage within the preferred range, while reducing exposure to unaffected areas of the skin.

The tiling or painting methods described above with reference to FIGS. 14 and 15 offer the healthcare provider a convenient technique for applying the photo-therapeutic doses to the affected tissue. The healthcare provider, however, preferably uses these methods in a manner so as to deliver a substantially uniform dose of light to the diseased area of tissue and one that is within the preferred range of doses.

Figure 20:
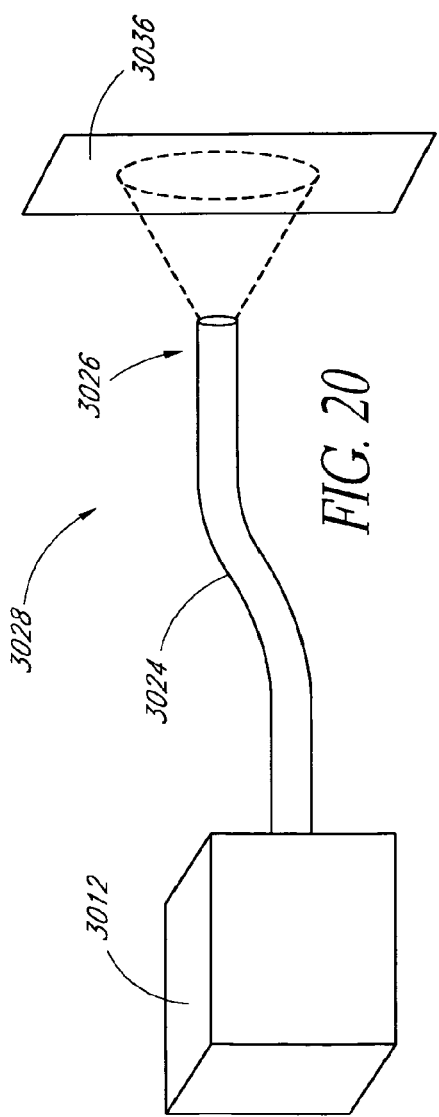
FIGS. 20 and 21 depict a delivery device that includes an optical fiber with a distal end that outputs light directed onto a target area and the resultant gaussian intensity distribution at the target area.

One possible delivery device 3028 for treating skin disorders with UV light may simply include an optical fiber 3024 with a distal end 3026 that outputs light of suitable wavelength and intensity; see FIG. 20. The light will diverge from the end 3026 of the optical fiber 3024 at an angle determined by the numerical aperture of the fiber. This light will have a two-dimensional gaussian intensity profile a distance away from the end 3026 of the fiber 3024 and in particular, on an area 3036 of the skin designated for treatment. To apply therapeutic doses to a diseased area 3036 of skin, the healthcare provider could scan the distal end 3026 of the fiber 3024 over the diseased tissue. The distance separating the end 3026 of the fiber from the skin will determine how large a region of the skin is illuminated as well as the intensity at any given point within that region. With farther separations, a larger the spot is illuminated but with less dosage being delivered to a fixed area of skin.

Figure 21:
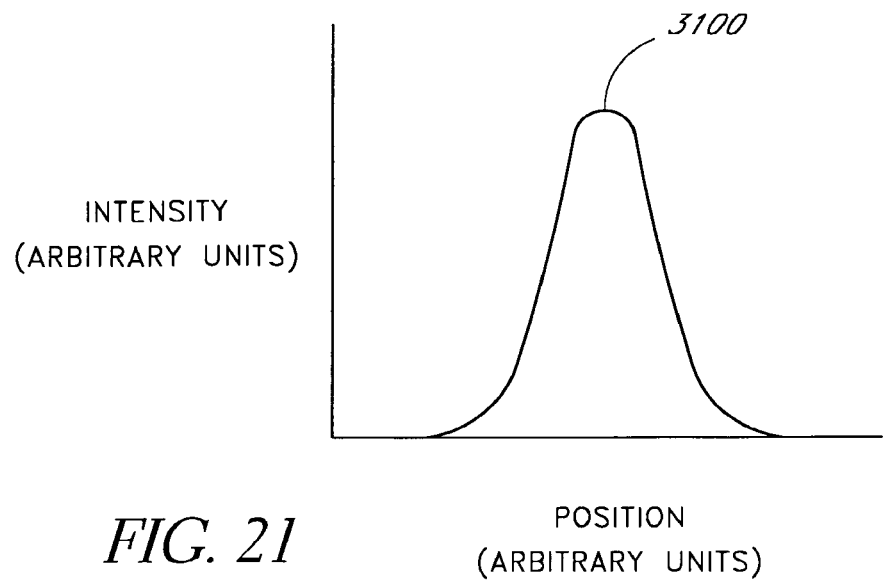

The gaussian intensity profile is well-known in the art. As shown in FIG. 21, which depicts a cross-section of a two-dimensional gaussian distribution, the intensity across of a gaussian beam has a central peak 3100, the beam intensity falling off rapidly with distance away from this center of the beam profile. The gaussian intensity profile, however, has the disadvantage of having a center portion of the target area 3036 that receives a substantially larger amount of energy than peripheral areas of the target. The uneven distribution of the gaussian profile results in the skin in the center portion of the target area 3036 being overexposed and/or the outer areas not receiving enough energy for effective treatment.

Figure 22:
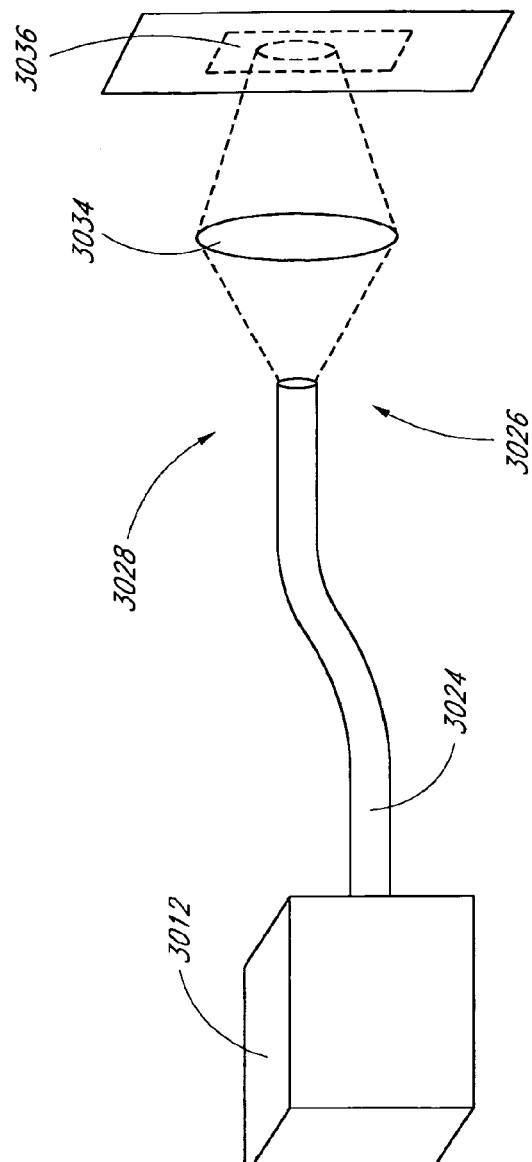
FIGS. 22 and 23 depict a delivery device that includes an optical fiber and a lens that outputs light directed onto a target area and the resultant substantially flat intensity distribution at the target area.

In another possible design depicted in FIG. 22, the delivery device 3028 may comprise an optical fiber 3024 and a lens 3034. Preferably, the lens 3034 has a numerical aperture that matches that of the fiber 3024. In addition, the lens 3034 has a suitable focal length and may be positioned, for example, to image the end 3026 of the optical fiber 3024 onto the target area of the skin 3036. This delivery system 3028 functions to transmit energy emitted from a source 3012, through the optical fiber 3024 and direct the optical energy onto the target area 3036. The illuminated area of skin is covered with a substantially uniform dosage of UV radiation as a consequence of the distal end 3026 of the fiber 3024 being imaged onto the skin. In the case where the end 3026 of the fiber 3024 has a circular cross-section, the resultant output on the target area is circularly shaped with a substantially flat intensity profile as illustrated in FIG. 23.

Figure 24:
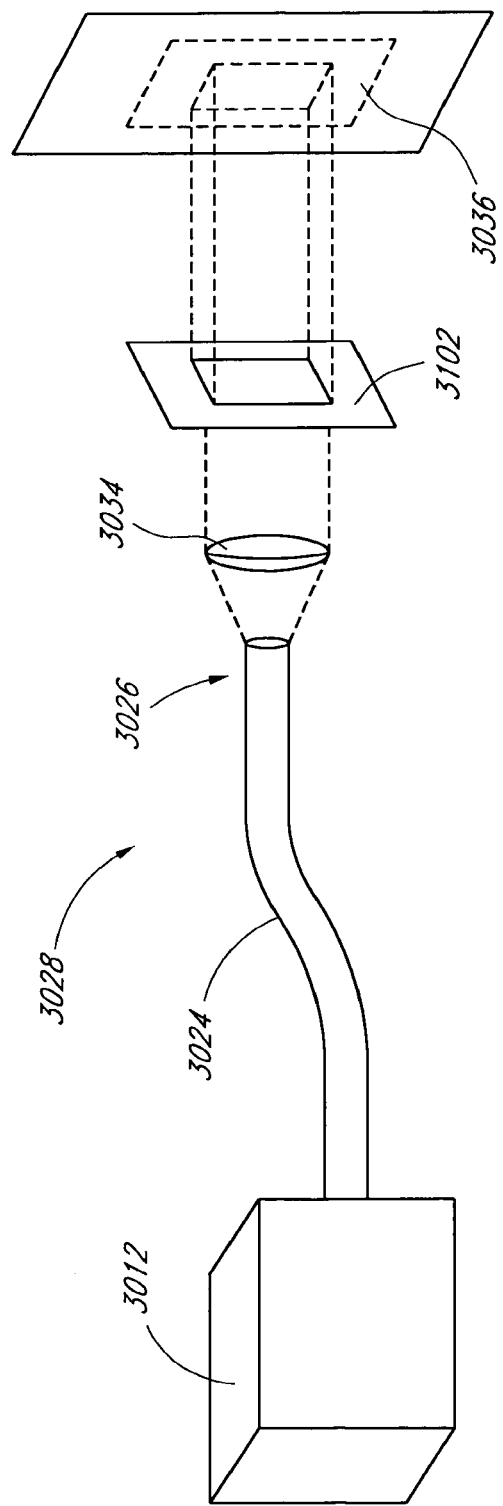
FIG. 24 depicts a delivery device that includes an optical fiber, a lens, and a rectangular aperture for directing light onto a target area.

As shown in FIG. 24, another possible delivery system 3028 may comprise an optical fiber 3024, a lens 3034, and a rectangular aperture 3102 contained within a handpiece 1030 (not shown) for delivery of the therapeutic doses of UV light. Here, the lens 3034 is positioned between the distal end 3026 of the fiber 3024 and the rectangular aperture 3102. The rectangular aperture 3102 is positioned in between the lens 3034 and the target area 3036. So arranged, a beam of light exits the distal end 3026 of the fiber 3024, is refracted by the lens 3034 and passes through the aperture 3102. The rectangular aperture 3102 is smaller than the diameter of the beam entering the aperture. The lens 3034 is preferably selected to have a numerical aperture that matches that of the optical fiber 3024 and a focal length and position with respect to the distal end 3026 so as to collimate the beam exiting the fiber.

This delivery system 3028 functions to produce a rectangular shaped intensity profile on the target 3036 of the skin. The fiber 3024 emits a diverging beam with circular cross-section and a two-dimensional gaussian intensity profile. The beam then travels through the lens 3034, which substantially collimates it. Thereafter, the beam passes through the rectangular aperture 3102, which truncates the edges of the circular shaped beam. The resultant output on the target area 3036 is a substantially rectangular shaped beam on the target area.

Figure 23:
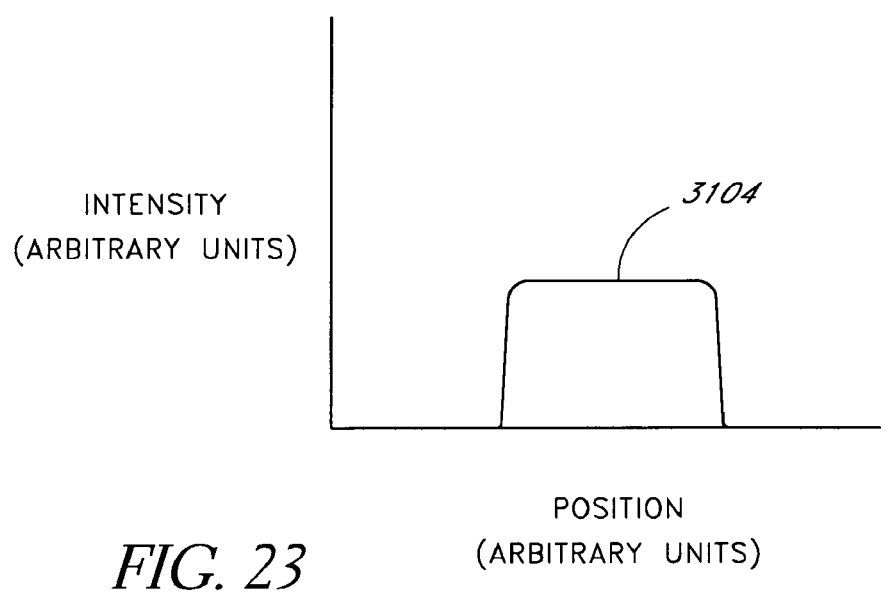

Compared to the gaussian intensity profile, the uniform intensity profile, a plot of which is shown in FIG. 23, has a substantially large flat center area 3104 with a sharp drop-off at the edges of the profile. The uniform intensity profile has the advantage over the gaussian energy profile of distributing the energy evenly over the target area 3036. The uniform energy profile, however, disadvantageously requires precise positioning of the handpiece 1030 and the beam when applying the UV light to the tissue. In particular, because the flat energy profile is substantially constant across the target area 3036, any overlap in treatment causes a doubling of the intended dose received by the patient's skin. Thus, the ultraviolet energy would have to be applied with a substantial amount of precision to ensure that no overlap in application occurs. Such strict alignment tolerances are not compatible with application by a healthcare provider manually scanning the handpiece 1030 over the patient's skin by hand.

To overcome this difficulty and enable the healthcare provider to more uniformly apply the therapeutic doses of UV, another preferred delivery device 3028 shown in FIG. 25 can be employed. This delivery device 3028 comprises an optical fiber 3024, a lens 3034, and a conduit 3108. In one embodiment, the fiber end 3026 has a circular cross-section, is approximately between about 600 micrometers (μm) and 5 millimeters (mm) in diameter, and has numerical aperture between about 0.22 and 0.39. The size and numerical aperture of the fiber may, however, differ in other embodiments. The lens 1034 preferably has a numerical aperture sufficiently large to collect a substantial portion of the light emanating from the fiber 3024. The lens 3034 may for example range in diameter between about 5 and 50 millimeters and may have a focal length of between about 5 and 25 mm. Other values outside these ranges are also considered possible. As shown in FIG. 25, the lens 3034 is positioned between the distal end 3026 of the fiber 3024 and the conduit 3108. In some preferred embodiments, the lens 3034 has a focal length of between about 5 and 50 millimeters and is positioned between about 5 to 50 millimeters from the distal end 3026 of the optical fiber 3024.

The conduit 3108 is a pipe or tube comprising four planar rectangular sidewalls 3110; see FIGS. 26A-26C. The rectangular sidewalls 3110 are joined together at a total of four edges 3112, each sidewall adjoined by two adjacent orthogonally disposed sidewalls at two edges. The conduit 3108 may be hollow or may be filled with a material that is preferably optically transmissive to the UV light. The four planar rectangular sidewalls 3110 create a passageway 3114 through the conduit 3108 for the UV light to follow. The conduit 3108 has proximal and distal ends 3116, 3118; the passageway 3114 through the conduit extends longitudinally from an opening 3120 at the proximal end of the conduit straight through the distal end which also has an opening 3122 therein. A direct longitudinal pathway continues through the conduit 3108, from the opening 3120 at the proximal end 3116 of the conduit to the opening 3122 at the distal end 3118 of the conduit.

The openings 3120, 3122 and the passageway 3114, being defined by the four sidewalls 3110, have rectangular, i.e., square, cross-sections 3124 with a center 3126 shown in FIG. 26B. Accordingly, the conduit 3108 may be referred to as a square or rectangular conduit, meaning that the conduit has a square or rectangular cross-section 3124 perpendicular to the longitudinal direction such as shown in FIG. 26B.

Each of the sidewalls 3110 has an inner surface 3128 that is reflective. These surfaces 3128 may be diffusely or specularly reflective. Each of the sidewalls 3110 preferably have a width, w, of between about 6 to 20 mm, and a length, l, extending in the longitudinal direction of about 30 to 200 mm. Accordingly, the conduit 3108 preferably has a length, l, extending in the longitudinal direction of between about 30 to 200 mm and a square cross-section 3124, having a width, w, of about 6 to 20 mm on a side. Dimensions outside these ranges are also considered possible.

Although a square cross-section 3124 is shown, the cross-section can otherwise be rectangular if the width, w, of the sidewalls 3110 are not identical. Other conduits 3108 can also be employed having different cross-section, such as for example, triangular, pentagonal, hexagonal, octagonal shapes. Square and rectangular cross-sections 3124 are preferred, however, to accommodate tiling and painting application modes. The number, size, and arrangement (i.e., angular disposition) of sidewalls 3110 may be selected to create the desired cross-section.

The conduit 3108 may comprise aluminum, as aluminum is sufficiently reflective. Alternatively, the conduit 3108 may be formed from other materials as well. Non-reflective material can be employed and the inner surfaces 3128 of the sidewalls 3110 coated with a sufficiently reflective layer. The hollow conduit 3108 may be substituted with a solid rectangular prism of material that transmits the appropriate wavelength UV light. For example, quartz or fused silica can be employed. The solid rectangular prism would have a rectangular, maybe square cross-section 3124, similarly formed by four planar rectangular sidewalls 3110. The inner surface 3128 of the sidewalls 3110 would be reflective as a result of total internal reflection. Aluminum conduits 3108 such as shown in FIG. 26A-26C are preferred, however, since they are inexpensive, rugged, and easy to fabricate. The conduit 3108 may be so inexpensive that it together with the handpiece 1030 which houses it, can be disposed of and completely replaced more often than a more expensive handpiece.

Preferably, the lens 3034 has a focal length and position such that the distal end 3026 of the optical fiber 3024 is imaged onto the target area 3036 of the skin or tissue. Specifically, a magnified image of the distal end 3026 of the optical fiber 3024 is preferably formed on the skin or tissue. Since the focal length of the lens 3034 may range, for example, between about 5 to 50 millimeters, the lens may be positioned a distance of between about 5 to 50 millimeters from the distal end 3026 of the fiber 3024 so as to produce a magnified image on the skin or tissue at location of about 10 to 40 millimeters from the lens. Although a single lens is shown in FIG. 25 for imaging the distal end 3024 of the fiber 3024 on the skin or tissue, other focusing systems such as for example a plurality of refractive optical elements can be suitably employed.

Together the distal end 3026 of the optical fiber 3024, the lens 3034, and the target area 3036 define an optical axis 3130 that extends from the distal end, through the lens and to the target area. The rectangular conduit 3108 is positioned such that the optical axis 3130 passes through the conduit, preferably through a centerline that runs through the conduit. This centerline would intersect a point located at the center 3126 of the rectangular or square cross-section 3124 depicted in FIG. 26B. To align the optical axis 3130 with the centerline that passes through the conduit 3108, the conduit is oriented therefore so that its length, l, is parallel to the optical axis.

Figure 27:
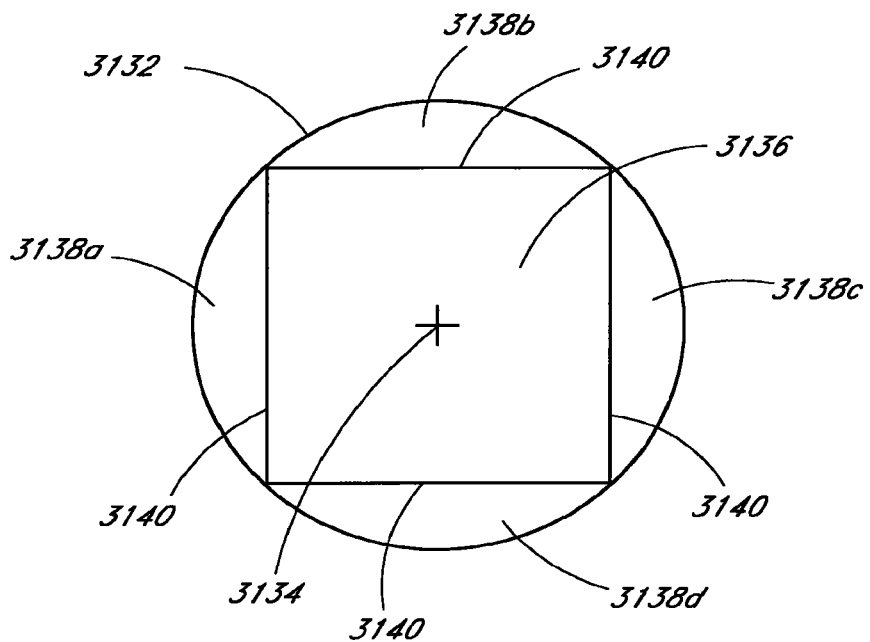
FIGS. 27 and 28 show cross-sectional views of the light beam before and after propagating through the rectangular conduit.

The optical beam follows a path through the delivery system 3028 as follows. First, the beam of UV light propagating through the optical fiber 3024 exits through the distal end 3026. The beam emanating from the end 3026 of the optical fiber 3024 has a circular cross-section and a gaussian energy profile. This beam is diverging with a maximum divergence angle defined by the numerical aperture of the optical fiber 3024. The beam, centered about the optical axis 3130, is directed through the lens 3034. The lens 3034 refracts the beam so as to form an image of the distal end 3026 of the optical fiber 3024 on the target region 3036. The beam exiting the lens 3034 has a circular cross-section 3132 with a center 3134 and a central portion 3136 which is depicted in FIG. 27. This beam is directed down the optical axis 3130, the optical axis coinciding with the center 3134 of the beams cross-section 3132.

The beam after passing through the lens 3034, enters the conduit 3108 through the opening 3120 in the proximal end 3116. The size of the diverging beam, i.e., the circular cross-section 3132, preferably will exceed the size of the cross-section 3124 of the rectangular conduit 3108, at least toward the distal end 3118 of the conduit. Accordingly, as the beam propagates through the conduit 3108, peripheral sections 3138a, 3138b, 3138c, 3138d of the beam are reflected off of the inner surface 3128 of the sidewalls 3110. Preferably, rays of light experience only one reflection. So designed, the conduit 3108 functions to fold in the peripheral sections 3138a, 3138b, 3138c, 3138d of the circular-shaped beam entering the conduit inward toward the center 3134 of the beam as defined by its cross-section 3132. The beam then exits the conduit 3108 through the opening 3122 at the distal end 3118 of the conduit and propagates toward the target area 3036.

The circular cross-section 3132 of FIG. 27 depicts the circular beam before the beam reflects off of the sides 3110 of the conduit. The circular beam is shown with four chords 3140 corresponding to the four sidewalls 3110 of the conduit 3108 that together form the rectangular, i.e., square aperture. Each cord 3140 is associated with one peripheral section 3138a, 3138b, 3138c, 3138d of the circularly shaped beam, the respective peripheral section being defined by the chord and the circular perimeter of the beam. Each of these peripheral sections 3138 is reflected and folded in toward the central portion 3136 of the beam. The portion of the beam that fit within the rectangular cross-section 3124 of the conduit 3108 will propagate un-deflected therethrough.

Figure 28:
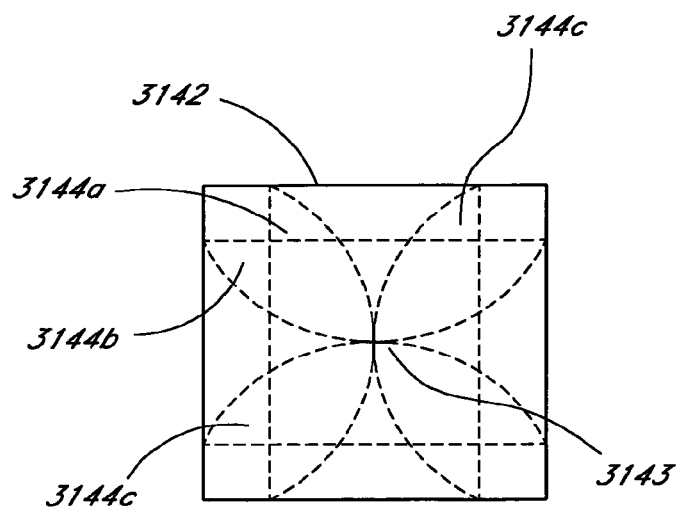

FIG. 28 shows a cross-section 3142 of the resultant beam after it has passed through the conduit 3108. The cross-section 3142 of the beam incident on the target area 3036 is substantially rectangular, i.e., square, with a center 3143 coinciding with the optical axis 3130. The peripheral sections 3138a, 3138b, 3138c, 3138d have been truncated, or more specifically, reflected off the sidewalls 3110 of the conduit 3108 inward toward the central portion 3136 of the beam, thereby converting the circular cross-section 3124 into the square cross-section 3142 shown.

FIG. 28 also illustrates regions 3144a, 3144b, 3144c, 3144d on the target area 3036 where the respective peripheral sections 3138a, 3138b, 3138c, 3138d of the beam are mapped. Such mapping is the result of rays of light associated with, for example, one of the peripheral regions 3138a, being reflected off the respective sidewall 3110 and directed to the respective region 3144a within the square cross-section 3142 of the beam formed on the patient's skin. These four regions 3144a, 3144b, 3144c, 3144d are located within the central portion 3136 of the beam. Each region 3144a, 3144b, 3144c, 3144d overlaps two of the other regions. Overlapping results in even greater intensity. The delivery device 3028, however, can be designed such that all of the regions 3144a, 3144b, 3144c, 3144d overlap if suitable for the intended purpose by positioning the conduit 3108 further from the lens 3034 or increasing its length, l.

Figure 29:
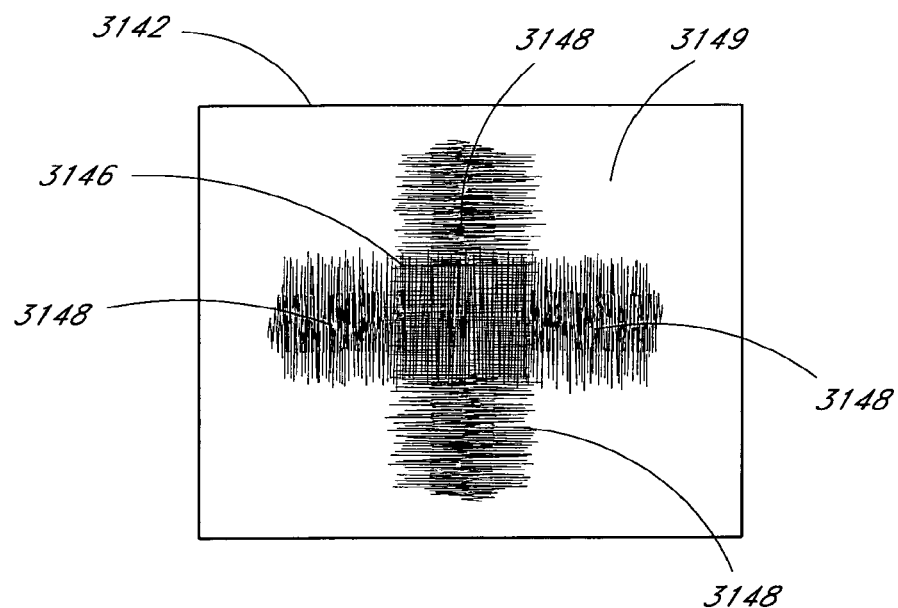
FIG. 29 depicts a cross-section of the light beam output by the delivery device illustrated in FIG. 25 incident on the target area.

Without the conduit 3108 and the reflections it produces, the dosage directed onto the skin would be substantially constant throughout. With the conduit 3108 appropriately positioned, however, light within the peripheral portions 3138a, 3138b, 3138c, 3138d is reflected off the sidewalls 3110 toward the center 3134 of the beam and adds to the intensity of light associated with the rays that pass through the conduit un-reflected. The regions 3144a, 3144b, 3144c, 3144d within the central portion 3136 of the beam will therefore have an intensity that is augmented by the reflected light. FIG. 29, which depicts the cross-section 3142 of the beam incident on the target area 3036, as well as FIG. 30, a plot on three axes of the dosage as a function of position, illustrate the resultant non-circularly symmetric intensity distribution on the skin. A cross-shaped region 3146 having four extensions 3148, with heightened illumination is superimposed on a background 3149 that is formed from un-reflected rays and which is otherwise substantially flat or constant. This cross-shaped region 3146 is centered about the optical axis 3130 which marks the center 3134 of the beam. The cross-shaped region 3146 is formed from contributions of the light within the peripheral portions 3138a, 3138b, 3138c, 3138d of the beam that is reflected by the sidewalls. As shown, the cross-section 3142 of the beam is substantially rectangular or more specifically, substantially square. Light however, fills the entire rectangular cross-section 3142.

Figure 30:
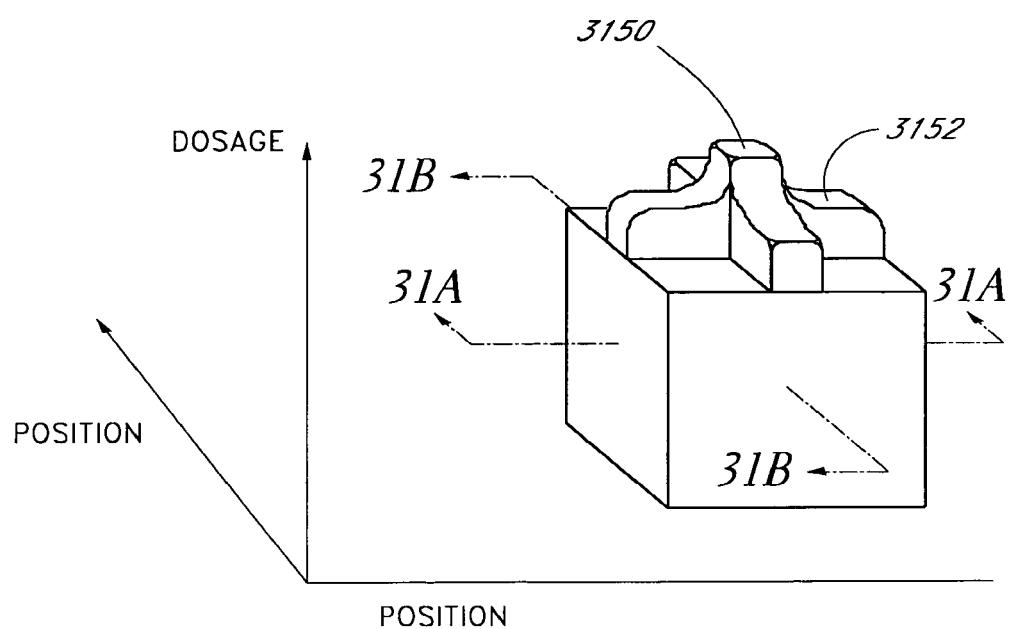
FIG. 30 is a plot of the dosage produced by the delivery device of FIG. 25 as a function of position on the target area.
Figure 31A:
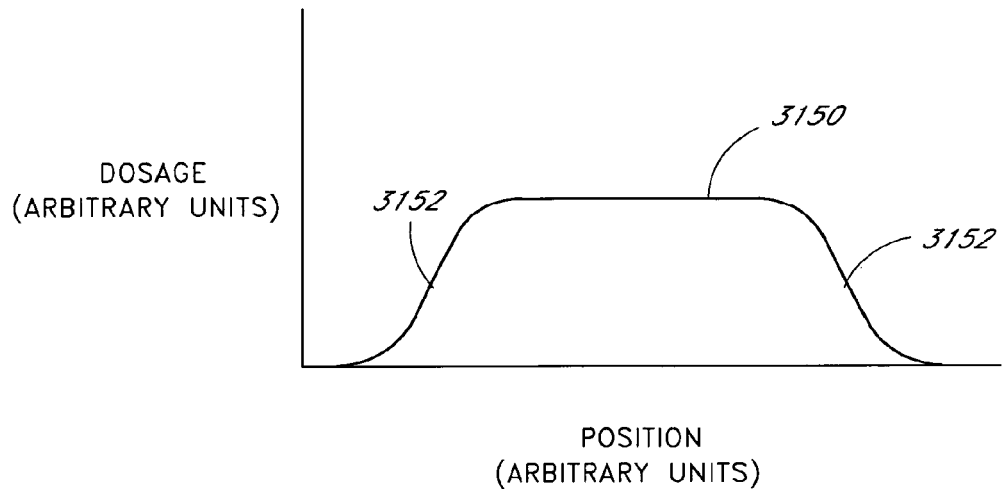
FIGS. 31A and 31B are profiles of the intensity along perpendicular directions of the plot shown in FIG. 30.
Figure 31B:
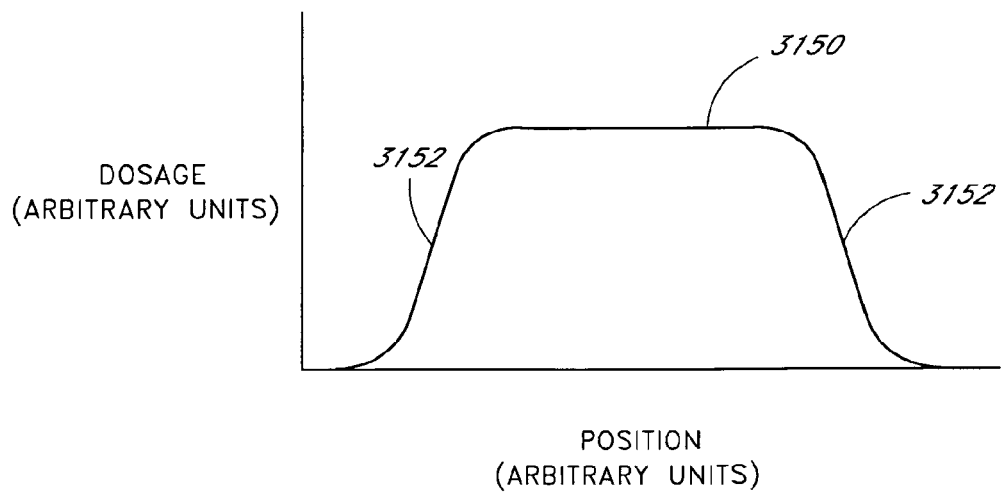

As illustrated by FIGS. 30 and 31A-31B, the rectangular conduit 3108 produces a beam profile that includes both regions of substantially uniform illumination 3150 as well as regions 3152 where the dosage tapers-off. The profile depicted in FIGS. 31A-31B shows the dosage variation along perpendicular lines both which pass through the center 3134 of the rectangular cross-section 3142 of FIG. 29 and are parallel to the two position axes. Each of these lines are also parallel to one pair of sidewalls 3110. Since the conduit 3108 has four-fold symmetry, so to does the resultant illumination pattern as shown by the cross-section 3142 of FIG. 29 and as demonstrated by the similar beam profiles across the lines 31A-31A and 31B-31B.

This plot of the non-uniform illumination profile shown in FIGS. 31A and 31B is substantially flat in the region 3150 in the center 3134 of the beam. The intensity is therefore fairly uniform within the central region 3136. This substantially uniform region 3150 continues out into each of the four extensions 3148 of the cross-shaped region 3146. As illustrated in FIGS. 31A and 31B, this substantially constant intensity region 3150 is bounded on both sides by the two regions 3152 of tapered intensity. The dosage falls-off in these two outer regions 3152.

The resultant illumination pattern is particularly advantageous for delivering a substantially uniform therapeutic dosage over an area of the patient's skin. As indicated above, one preferred mode of application is by the tiling or painting methods. In each of these modes, the healthcare provider manually scans the handpiece 3030 over the affected area 3036 of tissue. A uniform distribution of light is preferably provided over this region 3036 of the epidermis.

The resultant beam profile has the advantage of better enabling the heathcare provider apply a substantially uniform dosage to an area of skin having a lesion formed thereon. The risk of the dosage falling outside the range for successful treatment can therefore be substantially reduced. In particular, the substantially flat central region 3150, devoid of a central peak, has the advantage over a purely gaussian intensity profile in that it does not produce an overexposure at the center 3134. In addition, the outer portions 3152 of the beam having a tapered intensity reduce the risk that the patient will receive an overdose of ultraviolet energy if the healthcare provider partially overlap scans. The cross-shaped region 3146 of increased intensity is also useful for delivering appropriate levels of light to an irregularly shaped feature such as a lesion on the skin. A bright elongated feature with fairly distinct corners located within the rectangular cross-section 3142 of the beam allows the health-care provider to more precisely apply UV light to small irregularly shaped areas. One of the extensions 3148 on the cross-shaped central region 3146 can be suitably employed for this purpose. Exposure to a feature such as a mole that is overly sensitive to UV light can also be reduced with the aid of such a bright elongated feature within the beam.

Thus, the intensity pattern produced by employing the rectangular conduit 3108 can enable the healthcare provider to deliver a dosage to the target area that is sufficient for successful treatment, but that does not result in overexposure of portions of the skin. These devices also allow the healthcare provider to partially overlap scans without injuring the patient.

Other patterns that include at least one bright elongated feature may be used in the alternative to permit the application of therapeutic doses to an irregularly shaped features on the skin. For example, a single elongated region of high intensity, two or more such regions crossed at angles to form an "X" or star shaped central intensity pattern or various other shapes with elongated regions of high intensity, preferably with at least somewhat distinct corners and tapered fall-off may be suitable. These patterns may be created by conduits having cross-sections other than square or rectangular or can be generated by other techniques. Preferably, however, the beam cross-section has two pairs of parallel sides as does a square or rectangle.

One additional advantage of this design is that the beam can be tailored without much loss. About 90% of the light output by the optical fiber 3024 reaches the target area 3036 of the skin. The primary loss is reflection loss at the lens 3034. In contrast, simply truncating the peripheral portions of a beam with a circular cross-section to form a beam with a square cross-section would result in a loss of about 36.3%.

Yet another advantage of this design is that the resultant handpiece 1030 is both robust and inexpensive. The conduit 3108, which can be fabricated from aluminum or other similar metals, is both strong and relatively inexpensive in comparison to, for example, a polished quartz optical element. This metal component 3108 is also not nearly as fragile. As a consequence of its low cost, the handpiece 1030 can be readily disposed of and replaced when it is contaminated without imposing excessive costs onto the heathcare provider and the patient.

Figure 32:
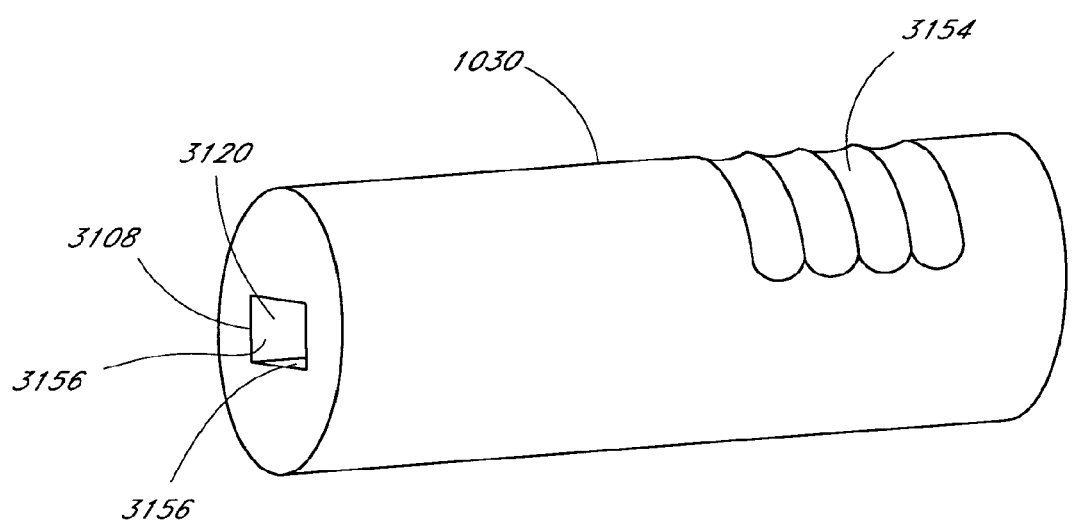
FIG. 32 depicts a delivery device wherein the conduit is formed integral with a handpiece.

In another preferred embodiment, the conduit 3108 is formed integral with the handpiece 1030 as depicted in FIG. 32. The handpiece 1030, which may have an exterior surface 3154 contoured to fit the grip of a hand, has incorporated therein the passageway 3114 extending through it. This passageway 3114 may have the same shape as the passageway in the conduit 3108 shown in FIGS. 26A-26C. This passageway 3114 has a rectangular or square cross-section. The passageway 3114 is defined by planar walls 3156 within the handpiece 1030 that reflect the beam of light emanating from the optical fiber 3024. This handpiece 1030 preferably may comprise aluminum with this rectilinear passageway 3114 machined or formed therein by casting. The sidewalls 3156 may also be plated with a metal such as nickel or gold which reflect light and preferably do not oxide excessively. Light enters the opening 3120, propagates through the passageway 3114 and exits the opening 3122 at the distal end 3118 in a similar manner as described above in connection with the conduit 3108 shown in FIGS. 26A-26C. The resultant illumination pattern is the same as that produced by the conduit 3108 described above, namely, the dosage is distributed as shown in FIGS. 29, 30, 31A, and 31B. The conduit 3108 here is, however, formed as an integral part of the handpiece 1030. This handpiece 1030 is thus relatively inexpensive and can be disposed of and replaced by another handpiece without undue hardship and expense to the healthcare provider and patient. This handpiece 1030 is also particularly rugged and can withstand impact and other forces that may otherwise damage more fragile designs.

Figure 33:
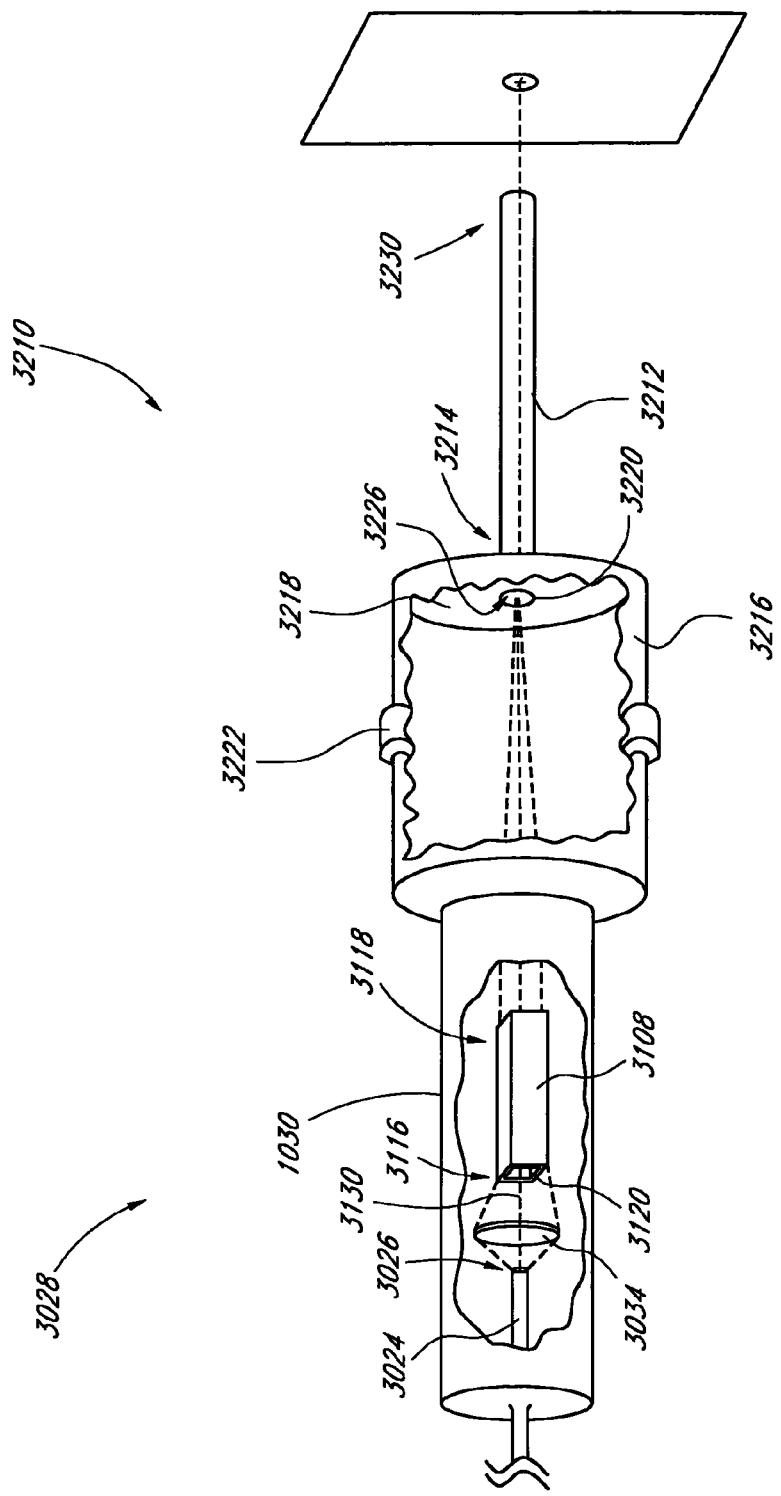
FIG. 33 depicts a delivery device further comprising an attachment for treating tissue within the mouth of a patient.
Figure 34:
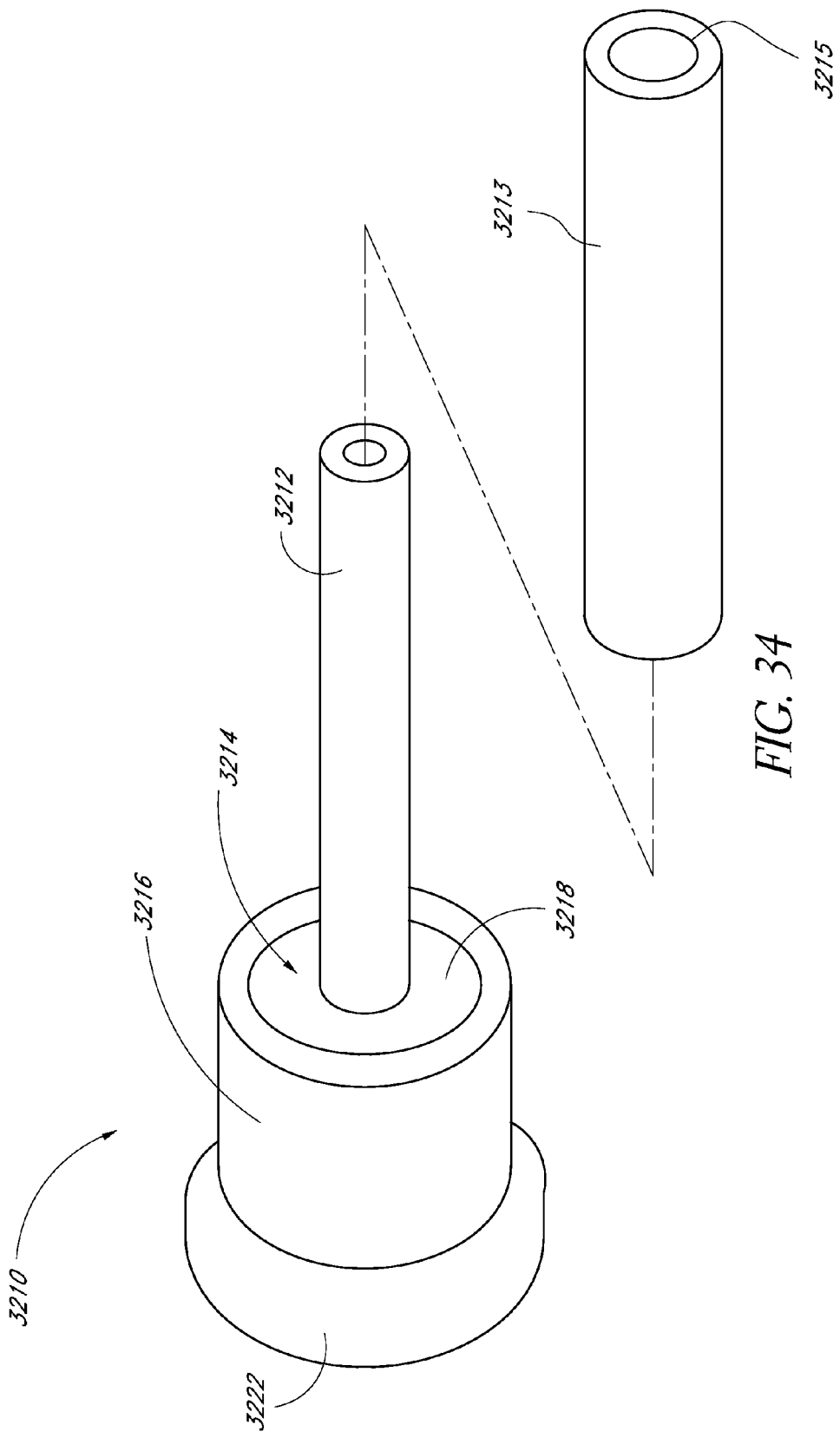
FIG. 34 depicts the attachment shown in FIG. 33 comprising an elongate tubular member having a channel therein.

Application of high dosages of ultraviolet light can also be employed to successfully treat oral lichen planus. Light having a wavelength of about 308 nanometers in high doses, e.g., greater than about 1 MED, can be applied to lesions on the mucous membranes in the mouth to improve the condition of a patient afflicted by a disorder adversely affecting the oral tissue. To facilitate application of such light to tissue within the mouth, an attachment 3210 can be provided to the handpiece 1030 as shown in FIG. 33. This attachment 3210 may comprise a stainless steel tube 3212 having a proximal end 3214 connected to an adapter 3216 that mates to the end of the handpiece 1030. As shown in FIGS. 33 and 34, the adapter 3216 is cylindrical in shape and has a surface 3218 to which the proximal end 3214 of the stainless steel tube 3212 is adjoined. This surface 3218 has an opening 3220, which receives the proximal end 3214 of the tube 3212. The adapter 3216, however, is not restricted to any single particular shape or design but is preferably configured to position the proximal end 3214 of the stainless steel tubing 3212 at the appropriate location that is described more fully below. The adapter 3216 includes a flange 3222 that fits to the end of the handpiece 1030. The size of the handpiece 1030 and the flange 3222 may be appropriately selected such that a snug fit is formed therebetween that prevents inadvertent detachment. Alternatively, the end of the handpiece 1030 and the flange 3222 may be threaded to form an even more secure interconnection. Other fastening techniques as are well known in the art or yet to be devised may be employed to provide for rigid attachment of the adapter 3222 to the handpiece 1030 yet enable subsequent removal thereof such that a healthcare provider can firmly attach the adapter 3216 to the handpiece 1030 and subsequently remove it therefrom.

Figure 35:
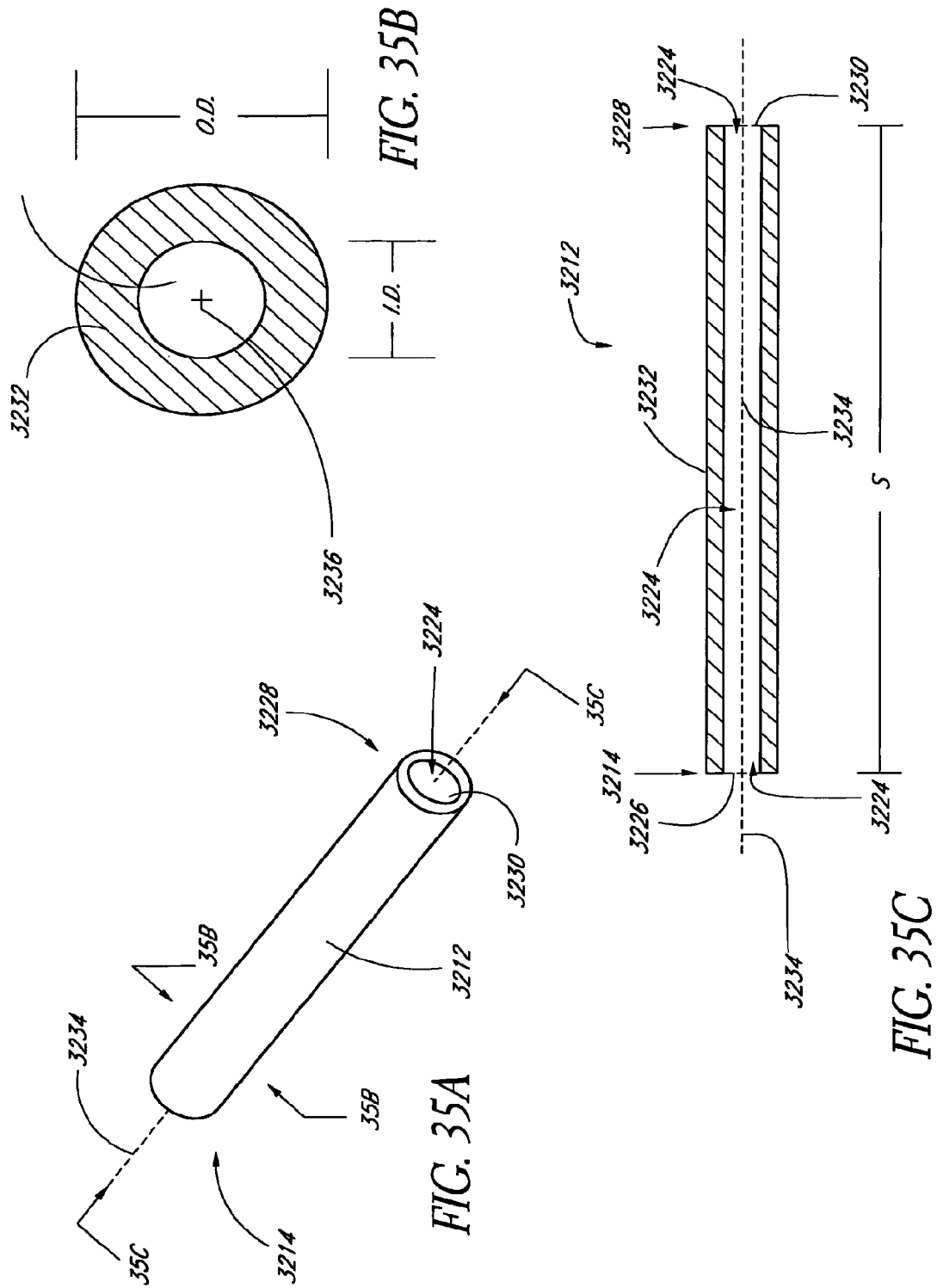
FIG. 35A-35C are perspective and cross-sectional views of the elongate tubular member showing the channel within the elongate member.

As shown in FIGS. 35A to 35C, the stainless steel tubing 3212 may comprises a rigid, straight, elongated structure having a hollow section 3224 formed therein by conventional techniques such as for example by machining, casting, and/or extruding. The proximal end 3214 of the stainless steel tube 3212 has an opening 3226 that leads to the hollow section 3224 which continues through the tubing to an end 3228, herein referred to as the distal end, having another opening 3230 therein. The two openings 3226, 3230 provide an unobstructed pathway through the hollow stainless steel tubing 3212. Light can thus freely pass from the opening 3226 at the proximal end 3214 through the hollow section 3224 to the distal end 3228 and through its respective opening 3230.

The tubing 3212 has sidewalls 3232 centered about a longitudinal axis or centerline 3234 passing through the tubing 3212. Cross-sections of the sidewall 3232 taken perpendicular to the centerline 3234 (see FIG. 35B) are circular with centers 3236 coinciding with the longitudinal axis 3234. The sidewalls 3232 are preferably sufficiently thick to provide rigidity. So designed, the tubing 3212 preferably will not flex or collapse when inserted in the mouth and pressed against structures or tissue within or in the proximity of the mouth such as the lips and cheek. The tube 3212 has a length, S, preferably so as to allow delivery of UV light deep into the mouth yet to provide ample maneuverability and control to the healthcare provider manually working the handpiece 1030 with the attachment appended thereto.

Although stainless steel is preferred, the sidewalls 3232 may comprise other materials that will not react in the moist environment within the mouth and that can be sterilized by heating to high temperature or by treating with chemicals. Other metals/metal alloys are considered possible, such as for example, aluminum. Suitable metal coatings that are resistant to oxidation or other chemical reactions when exposed to saliva, chemical and/or thermal sterilization can also be employed. Plastics and other polymer materials can be used as well. Although some plastics cannot be heated to high enough temperature and/or treated with chemicals to provide sterilization, since plastics are less expensive they can be disposed of without undue cost implications. Disposable plastic attachments 3210 may therefore take the form of rigid plastic tubes comprising substantially of plastic. A disposable plastic prophylactic 3213 (FIG. 34) can also be placed around the tubing 3212 prior to insertion into the oral cavity. This prophylactic 3213 may comprise a plastic or other polymer-based material and can be disposed of after use. Such prophylactics 3213 would be inexpensive and can be used to prevent germs from one patient from being transferred to another when the adapter 3216 is repeatedly used. In one embodiment, a removable plastic cap 3213 with an aperture 3215 therein is placed over the tubing. This aperture 3215 may comprise a hole or other region through which the light can pass. This aperture 3215 is aligned with the opening 2226, 2230 in the proximal and distal ends 3214, 3228 to allow light to pass therethrough.

When the attachment 3210 is affixed to the handpiece 1030, UV light propagating through the handpiece 1030 enters the proximal opening 3226 of the tubing 3212. This light travels through the hollow section 3224 of the tubing 3212, portions reflecting multiple times off the sidewalls 3232, and exits through the opening 3230 at the distal end 3228. The UV light can thereby be directed onto the patient's diseased mucous membranes in the mouth.

Figure 36:
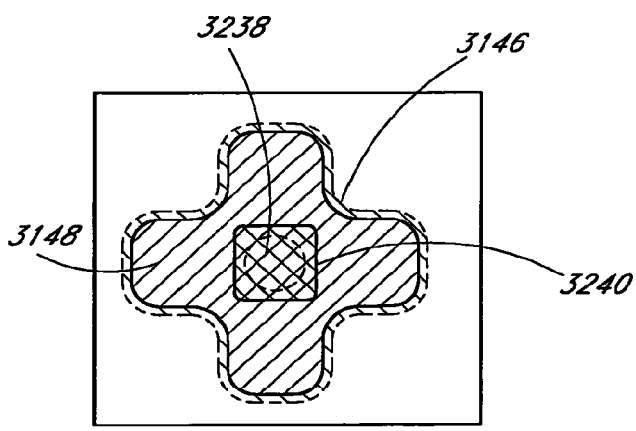
FIG. 36 depicts a cross-section of the light beam output by the rectangular conduit and received by the elongate tubular member of the attachment.

Preferably, the light entering the opening 3226 at the proximal end 3214 of the stainless steel tubing 3212 and that exits the opening 3230 at the distal end 3228 has a substantially uniform spatial intensity distribution. In one preferred embodiment, the handpiece 1030 includes a rectangular shaped conduit 3108 that provides the star shaped intensity pattern 3146 depicted in FIG. 36 at the surface 3218 of the adapter 3216 where the opening 3226 to the tubing 3212 is located. As discussed above, the central region 3238 of the star-shaped distribution 3146 has a substantially constant intensity throughout. Preferably, the opening 3226 of the tubing 3212 is centered on this substantially uniformly illuminated central region 3238 such that the light coupled into the tubing has a substantially uniform dosage, i.e. the dosage is substantially the same from the center 3236 to regions near the sidewalls 3232. An outline 3240 of the opening 3226 is shown superimposed on the star-shaped illumination pattern 3146 in FIG. 36. Light passing through the tubing 3212 will reflect multiple times off of the sidewalls 3232 adding to the uniformity of the distribution across a cross-section of the tubing taken perpendicular to the longitudinal axis or centerline 3234. Metal tubing 3212, which facilitates reflection within the hollow section 3224, is therefore preferred for providing increased uniformity. Diffusely reflecting surfaces, such as diffusely reflecting white or other UV bright surfaces, will also work well. Accordingly, roughened plastic or polymer-based material may provide a suitable surface for reflection.

Figure 37:
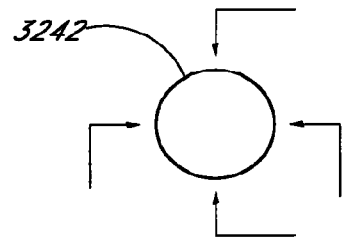
FIG. 37 depicts a cross-section of the light beam output by the elongate tubular member of the attachment.
Figure 39:
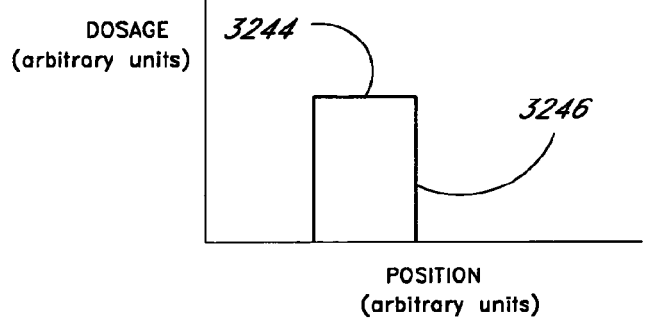
FIG. 39 is a profile of the intensity along perpendicular directions of the plot shown in FIG. 38.
Figure 38:
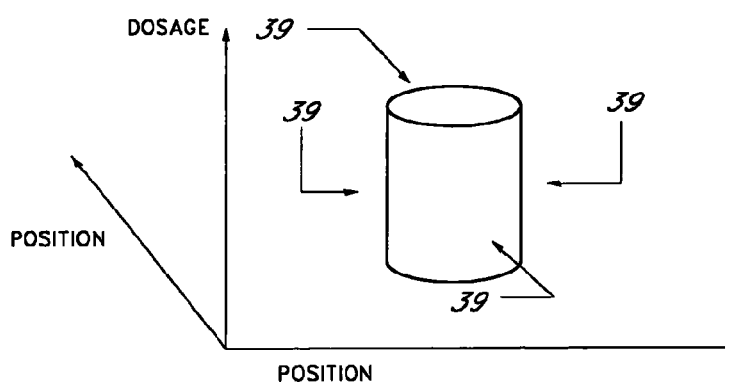
FIG. 38 is a plot of the dosage produced by the delivery device of FIG. 33 as a function of position on the target area.

The resultant distribution of light output from the tubing 3212 is illustrated in FIGS. 37-39. FIG. 37 is a cross-section 3242 taken perpendicular to the centerline or longitudinal axis 3234 showing the substantially uniform illumination of the beam at the exit orifice 3230. FIG. 38 shows a plot of the dosage level at the target area 3036 of the skin or tissue, and FIG. 39 depicts cross-sections of the plot in FIG. 38. A substantially constant region 3244 of illumination is surrounded by relatively sharp fall-offs 3246.

In the embodiment shown in FIG. 33, coupling uniform illumination into the tubing 3212 is provided by properly positioning the opening 3226 at the proximal end 3214 at the location where an image of the end 3026 of the optical fiber 3024 is formed; see FIG. 25 and discussion relating thereto. Other ways of providing a substantially uniform illumination that can be coupled into the attachment 3210 may also be suitably employed to provide uniform illumination at the output or distal end 3228 of the tubing 3212. Examples of such configurations are discussed, e.g., with regard to FIGS. 22 and 23. In other embodiments, however, non-uniform illumination is coupled into the opening 3226 at the proximal end 3214 of the tube 3212. The light output from the opening 3230 at the distal end 3228 of the tube 3212, however, preferably has a substantially uniform intensity distribution.

The attachment 3210 enables the healthcare provider to readily deliver high doses of UV light to diseased tissue within the mouth to treat disorders such as lichen planus. Since the tubing 3212 has a small outer diameter it can fit into the oral cavity and can be positioned directly over a lesion. The inner diameter is preferably sufficiently small that the dosage is limited to the affected areas of tissue. This diameter may range for example between about 1 millimeter and about 1 centimeter, however the size should not be limited to this range. Since the tubing is preferably sufficiently rigid, it will not flex against pressure imposed by the lips or cheek, which is may be pressed against. Accordingly, the physician or healthcare provider will be able to direct the beam as needed. In addition, the oral attachment 3210 can provide for treatments of multiple patients with a reduced risk of contamination. Some embodiments can be sterilized either by heating or by applying chemicals. Other embodiments are made of materials sufficiently inexpensive to allow them to be disposed of after use. Still in other embodiments, a disposable prophylactic can be placed over the tubing 3212 prior to insertion into the patient's mouth. A new prophylactic can be used with each new patient or treatment.

Although application of UV phototherapy to treat tissue within the mouth has been discussed in the context of an attachment 3210 used in conjunction with a handpiece 1030 (see FIGS. 33 and 34), various other embodiments are possible. For example, the tube or elongate member, which is inserted in the mouth to direct UV light on the target area of tissue, need not be an attachment. Also, in some cases a handpiece may not be used to manually control the application of the treatment. In other embodiments, for example, the elongated member with a channel therein is inserted in the mouth by using a mechanical system. Such a system may be automated.

In addition, the delivery device 3028 may comprise an elongate tubular member 3212 that is not a tube having a circular cross-section. For example, the cross-section may be rectangular, square, triangular, pentagonal, hexagonal, octagonal, elliptical, or irregularly shaped. Other shapes are also considered possible. Similarly, the channel 3224 or passageway through which the light travels and the distribution of light incident on the target area may have a cross-sectional shape other than circular. For example, the channel 3224 may have a cross-section perpendicular to the longitudinal axis and result in a UV illumination pattern that is rectangular, square, triangular, pentagonal, hexagonal, octagonal, elliptical, or have another shape which may or may not be irregularly shaped. As described above, the size of the cross-section and the resultant illumination pattern on the target area may range between about 1 millimeter to about 1 centimeter, but may be larger or smaller.

The elongate member 3212 may be hollow, comprising a empty cavity that provides an open passageway or channel for light to travel. Light propagating through this channel may be reflected from the sidewalls 3232 of the elongate member 3212 as described above. In other embodiments, the elongate member 3212 may comprise a material that is substantially optically transmissive to the UV light. For example, the elongate member 3212 may comprise a hollow tube filled with material substantially transparent to UV. Other embodiments wherein the channel comprises a solid or liquid material are also considered possible. In some embodiments, light propagating longitudinally through the elongate member 3212 may be reflected from sidewalls of the channel.

The elongate member 3212 itself may comprise metal, polymer, or other materials. In some embodiments, the elongate member 3212 comprises stainless steel, aluminum, or plastic but should not be limited to any particular material or material combination.

Although the range of dosage is preferably approximately 1 MED or greater, the dosage may be substantially higher or lower. For example, the dosage may be 10 or 100 times higher or lower. The dosage of UV light directed to the tissue in the mouth may range between about 1 millijoule per centimeter square ($mJ/cm^2$) to approximately several thousand millijoules per centimeter ($mJ/cm^2$), although dosages outside this range are also possible.

Additionally, although the methods and devices described may find use in treating oral lichen planus, their application should not be so limited. Rather, it may be useful to direct UV light onto tissue in the mouth to treat other conditions or for other reasons as well. Preferably, however, this UV light is limited to a narrow range of wavelengths such as described above, e.g., between about 295 nanometers to about 320 nanometers and more particularly, between about 300 and 310 nanometers, and preferably the dosage is greater than about 1 MED.

Also, although discussed in conjunction with various systems 10 for treating skin or tissue disorders described above, the oral UV photo-therapy should not be limited to any one type of system for producing or delivering the UV illumination. For example, the system 10 shown in FIG. 6, may or may not be employed. Other systems and other methods and techniques may be utilized instead. For example, cooling need not be applied and the rectangular conduit 3108 shown in FIG. 33 need not be used to provide uniform illumination at the proximal end 3214 of the elongate tube 3212.

Preferably, however, a UV source produces UV light that is optically coupled into an optical fiber and delivered to a target area of tissue using an elongate member 3212 having a channel 3224 therein through which the light propagates. This tissue may comprise tissue in the mouth wherein the elongate member is inserted in the mouth of a living being such as a human. Preferably, the elongate member can be sterilized or is disposable such that a clean sterile structure is inserted in the oral cavity of a living being with reduced risk of contamination and infection.

Those skilled in the art will appreciate that the methods and designs described above have additional applications and that the relevant applications are not limited to those specifically recited above. Also, the present invention may be embodied in other specific forms without departing from the essential characteristics as described herein. The embodiments described above are to be considered in all respects as illustrative only and not restrictive in any manner.

What is claimed is:

1. An optical apparatus for treating tissue in a body of a human being, the apparatus comprising:
   an ultraviolet light source configured to emit UV light;
   an optical fiber having a proximal end configured to receive said UV light emitted from said ultraviolet light source and a distal end configured to output said UV light to expose said tissue in said body to said UV light;
   an elongate member configured to be inserted into the body, said elongate member having a proximal end, a distal end, and an inner channel configured to direct said UV light from said proximal end of said elongate member to said distal end of said elongate member and onto a region of said tissue for exposure to said UV light; and
   a hollow prophylactic cap that fits over said elongate member, said prophylactic cap comprising an aperture configured to pass said UV light, wherein said prophylactic cap comprises a polymer-based material.

2. The optical apparatus of claim 1, wherein said ultraviolet light source comprises an excimer laser configured to emit light having a wavelength between about 300 and about 310 nanometers.

3. The optical apparatus of claim 1, wherein said elongate member comprises a tube having a shape of a right circular cylinder.

4. The optical apparatus of claim 1, wherein said inner channel is filled with a material substantially optically transmissive to said UV light.

5. The optical apparatus of claim 1, further comprising a lens positioned between said optical fiber and said elongate member, the lens configured to optically couple light from said optical fiber into said inner channel of said elongate member.

6. The optical apparatus of claim 1, further comprising a handpiece connected to said optical fiber and supporting said elongate member to permit manual application of said UV light to said tissue.

7. The optical apparatus of claim 6, wherein said elongate member is included on a detachable adapter for connection to said handpiece.

8. The optical apparatus of claim 1, wherein said optical fiber comprises a liquid filled optical guide.

9. The optical apparatus of claim 1, wherein portions of said UV light are configured to reflect multiple times off walls of the elongate member.

10. The optical apparatus of claim 1, further comprising a conduit between said optical fiber and said elongate member, wherein light exiting said optical fiber propagates longitudinally through said conduit to said elongate member.

11. The optical apparatus of claim 10, wherein said conduit comprises a cylinder having a pathway therein, said cylinder comprising four planar sidewalls that together form a region within said conduit for said light to propagate, said conduit having a rectilinear cross-section perpendicular to said longitudinal direction.

12. The optical apparatus of claim 10, wherein said conduit has planar sidewalls.

13. The optical apparatus of claim 1, wherein said polymer-based material comprises plastic.

14. The optical apparatus of claim 1, wherein said aperture comprises a hole.

15. The optical apparatus of claim 1, wherein said ultraviolet light source is configured to emit said UV light at an intensity of at least about 1 MED.

16. The optical apparatus of claim 1, wherein a beam output through said distal end of said elongate member has a substantially uniform intensity profile.

17. The optical apparatus of claim 1, wherein a beam output through said distal end of said elongate member has a substantially Gaussian intensity profile.

18. The optical apparatus of claim 1, wherein the elongate member comprises a polymer.

19. The optical apparatus of claim 1, wherein the elongate member is not sterilizable by treatment with at least one of heat and chemicals.

20. The optical apparatus of claim 1, wherein the elongate member comprises at least one of stainless steel and aluminum.

* * * * *